US011535854B2

(12) United States Patent
Jung et al.

(10) Patent No.: US 11,535,854 B2
(45) Date of Patent: Dec. 27, 2022

(54) MICROORGANISM STRAIN FOR HIGH-PERFORMANCE METABOLISM OF BIOMASS-DERIVED CARBON SOURCE

(71) Applicants: POSTECH ACADEMY-INDUSTRY FOUNDATION, Gyeongsangbuk-do (KR); SEOUL NATIONAL UNIVERSITY R&DB FOUNDATION, Seoul (KR)

(72) Inventors: Gyoo Yeol Jung, Gyeongsangbuk-do (KR); Dong Hun Kwak, Chungcheongbuk-do (KR); Sang Woo Seo, Seoul (KR); Hyun Gyu Lim, Gyeongsangbuk-do (KR)

(73) Assignees: POSTECH ACADEMY-INDUSTRY FOUNDATION, Gyeongsangbuk-Do (KR); SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 189 days.

(21) Appl. No.: 16/612,300

(22) PCT Filed: May 11, 2018

(86) PCT No.: PCT/KR2018/005437
§ 371 (c)(1),
(2) Date: Jun. 26, 2020

(87) PCT Pub. No.: WO2018/208120
PCT Pub. Date: Nov. 15, 2018

(65) Prior Publication Data
US 2020/0354755 A1 Nov. 12, 2020

(30) Foreign Application Priority Data
May 11, 2017 (KR) ........................ 10-2017-0058781

(51) Int. Cl.
| | | |
|---|---|---|
| *C12N 15/00* | (2006.01) | |
| *C12P 7/16* | (2006.01) | |
| *C12N 15/74* | (2006.01) | |
| *C12N 1/20* | (2006.01) | |
| *C12R 1/63* | (2006.01) | |

(52) U.S. Cl.
CPC ............... *C12N 15/74* (2013.01); *C12N 1/20* (2013.01); *C12P 7/16* (2013.01); *C12N 1/205* (2021.05); *C12R 2001/63* (2021.05); *C12Y 306/03001* (2013.01)

(58) Field of Classification Search
CPC .................................... C12N 15/74; C12P 7/16
See application file for complete search history.

(56) References Cited

U.S. PATENT DOCUMENTS

2014/0273128 A1 9/2014 Coleman et al.

OTHER PUBLICATIONS

Bhotra, et al. "Whole-Genome Sequence of Vibrio alginolyticus Isolated from the Mucus of the Coral *Fungia danai* in the Andaman Sea, India," American Society for Microbiology, Published May 5, 2016, 2 pp.
Lee, et al. "Recombineering in Vibrio Natriegens." BioRxiv, available at https://doi.org/10.1101/130088, last visited Feb. 7, 2022, 17 pp.
Farmer, et al. "Precursor Balancing for Metabolic Engineering of Lyopene Production in *Escherichia coli*," Biotechnol. Prog. 2001, vol. 17, pp. 57-61.
Zhang, et al. "Combining Genotype Improvement and Statistical Media Optimization for Isoprenoid Production in *E. coli*," PLOS ONE, Published Oct. 4, 2013; 11 pp.
Kim, et al. "Enchanced 2,3-Butanediol Production in Recombinant Klebsiella pneumoniae via Overexpression of Synthesis-Related Genes," Journal of Microbiology and Biotechnology, 2012, vol. 22 (9), pp. 1258-1263.
Jung Gy et al. Research report, Ministry of Science, ICT and Future Planning. (Apr. 2, 2016).
Chen, et al., "Functional characterization of an alkaline exonuclease and single strand annealing protein from the SXT genetic element of Vibrio cholerae", BMC Mol Biol., Apr. 18, 2011, 21 pages.
Doi, et al., "Identification of enzymes responsilble for extracellular alginate depolymerization and alginate metabolism in Vibrio algivorus", Appl Microbiol Biotechnol, Feb. 2017, pp. 1581-1592.
Kim, et al., "Redistribution of Carbon Flux toward 2,3-Butanediol Production in Klebsiella pneumoniae by Metabolic Engineering", PLOS One, vol. 9, Issue 10, Oct. 2014, 9 pages.
Lee, et al., "Recombineering in Vibrio natriegens", bioRxiv preprint; doi: http://dx.doi.org/10.1101/130088., Apr. 24, 2017, 17 pages.
Park, et al., "Application of the FLP/FRT system for conditional gene deletion in yeast *Saccharomyces cerevisiae*", Yeast; 28, Aug. 7, 2011, 9 pages.
PCT/KR2018/005437, International Search Report and Written Opinion with English Translation, dated Feb. 8, 2019, 28 pages.
Weinstock, et al., "Vibrio natriegens as a fast-growing host for molecular biology", Nature Methods, vol. 13, No. 10, Oct. 2016, pp. 849-851.

(Continued)

*Primary Examiner* — Yong D Pak
(74) *Attorney, Agent, or Firm* — Armstrong Teasdale LLP

(57) ABSTRACT

The present invention relates to a novel microorganism capable of metabolizing various carbon sources at high rates. A novel microorganism according to the present invention was observed to grow at a very high rate in a minimal medium/nutrient medium, etc., compared to microorganisms such as *Escherichia coli*, and shows resistance at a high initial sugar/salt concentrations as well as being able to produce lycopene and 2,3-butanediol through genetic manipulation. Therefore, the novel microorganism can be used in various production fields of high value-added compounds using microorganisms.

11 Claims, 16 Drawing Sheets

Specification includes a Sequence Listing.

(56) References Cited

OTHER PUBLICATIONS

Zhang, et al., "Combining Genotype Improvement and Statistical Media Optimization for Isoprenoid Production in *E. coli*", PLOS One vol. 8, Issue 10, Oct. 2013, 11 pages.

pACYC(Origin: p15A), chloramphenicol pUC(Origin: pMB1 derivative), ampicillin pACYC – Low copy of *Escherichia coli*
pUC – High copy of *Escherichia coli*

VDHG101: *Vibrio* sp. dhg / Ddns / pACYC_duet (Negative control)
VDHG102: *Vibrio* sp. dhg / Ddns / pACYC_idi_ispA_crtEBI
VDHG103: *Vibrio* sp. dhg / Ddns / pACYC_idi_ispA_crtEBI_dxs

SEQUENCE LISTING

```
<160> NUMBER OF SEQ ID NOS: 69

<210> SEQ ID NO 1
<211> LENGTH: 1535
<212> TYPE: DNA
<213> ORGANISM: Unknown
<220> FEATURE:
<223> OTHER INFORMATION: Vibrio sp. dhg

<400> SEQUENCE: 1
catggctcag attgaacgct ggcggcaggc ctaacacatg caagtcgagc ggaaacgagt      60
taactgaacc ttcgggggac gttaacggcg tcgagcggcg gacgggtgag taatgcctag     120
gaaattgccc tgatgtgggg gataaccatt ggaaacgatg gctaataccg catgatgcct     180
acgggccaaa gagggggacc ttcgggcctc tcgcgtcagg atatgcctag gtgggattag     240
```

```
ctagttggtg aggtaagggc tcaccaaggc gacgatccct agctggtctg agaggatgat    300
cagccacact ggaactgaga cacggtccag actcctacgg gaggcagcag tggggaatat    360
tgcacaatgg gcgcaagcct gatgcagcca taccgcgtgt gtgaagaagg ccttcgggtt    420
gtaaagcact ttcagtcgtg aggaaggtag tgtgtttaat agatgcatta tttgacgtta    480
gcgacagaag aagcaccggc taactccgtg ccagcagccg cggtaatacg gagggtgcga    540
gcgttaatcg gaattactgg gcgtaaagcg catgcaggtg gtttgttaag tcagatgtga    600
aagcccgggg ctcaacctcg aatagcatt tgaaactggc agactagagt actgtagagg    660
ggggtagaat tcaggtgta gcggtgaaat gcgtagagat ctgaaggaat accggtggcg    720
aaggcggccc cctggacaga tactgacact cagatgcgaa agcgtgggga gcaaacagga    780
ttagataccc tggtagtcca cgccgtaaac gatgtctact ggaggttgt ggccttgagc     840
cgtggctttc ggagctaacg cgttaagtag accgcctggg gagtacggtc gcaagattaa    900
aactcaaatg aattgacggg ggcccgcaca agcggtggag catgtggttt aattcgatgc    960
aacgcgaaga accttaccta ctcttgacat ccagagaact ttccagagat ggattggtgc   1020
cttcgggaac tctgagacag gtgctgcatg gctgtcgtca gctcgtgttg tgaaatgttg   1080
ggttaagtcc cgcaacgagc gcaacccctta tccttgtttg ccagcgagta atgtcggaa   1140
ctccagggag actgccggtg ataaaccgga ggaaggtggg gacgacgtca agtcatcatg   1200
gcccttacga gtagggctac acacgtgcta caatggcgca tacagagggc ggccaacttg   1260
cgaaagtgag cgaatcccaa aaagtgcgtc gtagtccgga ttggagtctg caactcgact   1320
ccatgaagtc ggaatcgcta gtaatcgtgg atcagaatgc cacggtgaat acgttcccgg   1380
gccttgtaca caccgcccgt cacaccatgg gagtgggctg caaaagaagt aggtagttta   1440
accttcgggg gacgcttacc actttgtggt tcatgactgg ggtgaagtcg taacaaggta   1500
gcgctagggg aacctggcgc tggatcacct cctta                               1535
```

<210> SEQ ID NO 2
<211> LENGTH: 272
<212> TYPE: PRT
<213> ORGANISM: Unknown
<220> FEATURE:
<223> OTHER INFORMATION: Vibrio sp. dhg

<400> SEQUENCE: 2

Met Glu Lys Pro Lys Leu Ile Gln Arg Phe Ala Glu Arg Phe Ser Val
1               5                   10                  15

Asp Pro Asn Lys Leu Phe Asp Thr Leu Lys Ala Thr Ala Phe Lys Gln
            20                  25                  30

Arg Asp Gly Ser Ala Pro Thr Asn Glu Gln Met Met Ala Leu Leu Val
        35                  40                  45

Val Ala Asp Gln Tyr Gly Leu Asn Pro Phe Thr Lys Glu Ile Phe Ala
    50                  55                  60

Phe Pro Asp Lys Gln Ala Gly Ile Ile Pro Val Gly Val Asp Gly
65                  70                  75                  80

Trp Ser Arg Ile Ile Asn Gln His Asp Gln Phe Asp Gly Met Glu Phe
                85                  90                  95

Lys Thr Ser Glu Asn Lys Val Ser Leu Asp Gly Ala Lys Glu Cys Pro
            100                 105                 110

Glu Trp Met Glu Cys Ile Ile Tyr Arg Arg Asp Arg Ser His Pro Val
        115                 120                 125

Lys Ile Thr Glu Tyr Leu Asp Glu Val Tyr Arg Pro Pro Phe Glu Gly

```
                    130                 135                 140
Asn Gly Lys Asn Gly Pro Tyr Arg Val Asp Gly Pro Trp Gln Thr His
145                 150                 155                 160

Thr Lys Arg Met Leu Arg His Lys Ser Met Ile Gln Cys Ser Arg Ile
                165                 170                 175

Ala Phe Gly Phe Val Gly Ile Phe Asp Gln Asp Glu Ala Glu Arg Ile
                180                 185                 190

Ile Glu Gly Gln Ala Thr His Val Val Glu Pro Ser Val Ile Pro Pro
            195                 200                 205

Glu Gln Val Asp Asp Arg Thr Arg Gly Leu Val Tyr Lys Leu Ile Glu
        210                 215                 220

Arg Ala Glu Ala Ser Asn Ala Trp Asn Ser Ala Leu Glu Tyr Ala Asn
225                 230                 235                 240

Glu His Phe Gln Gly Val Glu Leu Thr Phe Ala Lys Gln Glu Ile Ile
                245                 250                 255

Asn Ala Gln Gln Gln Ala Ala Lys Ala Leu Thr Gln Pro Leu Ala Ser
            260                 265                 270
```

<210> SEQ ID NO 3
<211> LENGTH: 819
<212> TYPE: DNA
<213> ORGANISM: Unknown
<220> FEATURE:
<223> OTHER INFORMATION: Vibrio sp. dhg

<400> SEQUENCE: 3

```
atggaaaaac caaagctaat tcaacgcttt gctgagcgct ttagtgtcga tccaaacaag      60
ttgttcgata ccctaaaagc aacagcattc aagcaacgtg acggtagtgc accgaccaat     120
gagcagatga tggcgctctt ggtggttgca gatcagtacg gcttgaaccc tttcaccaaa     180
gagatttttg cgttccctga taaacaagct gggattattc agtggtaggt gtcgatggaa     240
tggtctcgca tcattaatca acacgaccag tttgatggca tggagtttaa gacttcagaa     300
aacaaagtct ccctggatgg cgcgaaagaa tgcccggaat ggatggaatg catcatctat     360
cggcgcgacc gttcgcaccc agtcaaaatc actgaatacc tggatgaagt ctatcgaccg     420
cctttttgaag gtaacggcaa aaatggccct taccgggtag atggtccatg cagacgcac      480
actaagcgaa tgctaagaca taaatccatg atccagtgtt cccgcattgc gtttggcttt     540
gtgggaattt tcgatcaaga cgaagcggag cgaattatcg aaggccaagc aacacacgtt     600
gttgagccat cggtgattcc acccgagcaa gttgatgatc gaacccgagg gcttgtttac     660
aagcttatcg agcgggcgga agcttcaaac gcttggaata gtgcattgga atatgccaat     720
gaacattttc aaggtgttga actgacgttt gcgaaacaag aaataattaa tgcacagcaa     780
caagcagcca aagcgctcac acagcccttt agcttcttag                            819
```

<210> SEQ ID NO 4
<211> LENGTH: 338
<212> TYPE: PRT
<213> ORGANISM: Unknown
<220> FEATURE:
<223> OTHER INFORMATION: Vibrio sp. dhg

<400> SEQUENCE: 4

```
Met Lys Val Ile Asp Leu Ser Gln Arg Thr Pro Ala Trp His Gln Trp
1               5                  10                  15

Arg Ile Ala Gly Val Thr Ala Ser Glu Ala Pro Ile Ile Met Gly Arg
            20                  25                  30
```

```
Ser Pro Tyr Lys Thr Pro Trp Arg Leu Trp Ala Glu Lys Thr Gly Phe
        35                  40                  45

Val Leu Pro Glu Asp Leu Ser Asn Asn Pro Asn Val Leu Arg Gly Ile
 50                  55                  60

Arg Leu Glu Pro Gln Ala Arg Arg Ala Phe Glu Asn Ala His Asn Asp
 65                  70                  75                  80

Phe Leu Leu Pro Leu Cys Ala Glu Ala Asp His Asn Ala Ile Phe Arg
                85                  90                  95

Ala Ser Phe Asp Gly Ile Asn Asp Ala Gly Glu Pro Val Glu Leu Lys
               100                 105                 110

Cys Pro Cys Gln Ser Val Phe Glu Asp Val Gln Ala His Arg Glu Gln
               115                 120                 125

Ser Glu Ala Tyr Gln Leu Tyr Trp Val Gln Val Gln His Gln Ile Leu
       130                 135                 140

Val Ala Asn Ser Thr Arg Gly Trp Leu Val Phe Tyr Phe Glu Asp Gln
145                 150                 155                 160

Leu Ile Glu Phe Glu Ile Gln Arg Asp Ala Ala Phe Leu Thr Glu Leu
                165                 170                 175

Gln Glu Thr Ala Leu Gln Phe Trp Glu Leu Val Gln Thr Lys Lys Glu
               180                 185                 190

Pro Ser Lys Cys Pro Glu Gln Asp Cys Phe Val Pro Lys Gly Glu Ala
       195                 200                 205

Gln Tyr Arg Trp Thr Ser Leu Ser Arg Gln Tyr Cys Ser Ala His Ala
       210                 215                 220

Glu Val Val Arg Leu Glu Asn His Ile Lys Ser Leu Lys Glu Glu Met
225                 230                 235                 240

Arg Glu Ala Gln Ser Lys Leu Val Ala Met Met Gly Asn Tyr Ala His
                245                 250                 255

Ala Asp Tyr Ala Gly Val Lys Leu Ser Arg Tyr Met Met Ala Gly Thr
              260                 265                 270

Val Asp Tyr Lys Gln Leu Ala Thr Asp Lys Leu Gly Glu Leu Asp Glu
       275                 280                 285

Gln Val Leu Ala Ala Tyr Arg Lys Ala Pro Glu Arg Leu Arg Ile
       290                 295                 300

Ser Thr Asn Lys Pro Glu Gln Pro Val Glu Thr Pro Ile Lys Ile Ser
305                 310                 315                 320

Leu Glu Gln Glu Asn Leu Val Leu Pro Gly Asp Ser Pro Ser Ser Phe
                325                 330                 335

Tyr Phe

<210> SEQ ID NO 5
<211> LENGTH: 1017
<212> TYPE: DNA
<213> ORGANISM: Unknown
<220> FEATURE:
<223> OTHER INFORMATION: Vibrio sp. dhg

<400> SEQUENCE: 5
atgaaggtta tcgacctatc acaacgtact cctgcatggc accagtggcg cattgcaggg    60
gttacggcat ctgaagcccc aattattatg gggcgttcac cctacaaaac accttggcga   120
ttatgggcag aaaaaaccgg attcgtatta ccggaagacc tatcgaataa tccaaatgtg   180
cttcgaggta tacggttgga gcctcaagca aggcgagcat ttgagaatgc gcataatgac   240
tttcttctgc cgttatgtgc agaagccgat cataacgcaa tctttcgagc cagctttgat   300
```

```
ggcatcaacg atgcgggcga acctgttgaa ctgaaatgtc cttgccagtc agttttgag      360 gatgtgcaag ctcaccgaga acaaagtgag gcgtaccagt tgtattgggt gcaagtacag      420
caccaaatac tggtcgccaa tagcacgcgt ggttggttgg tattctattt tgaggatcaa      480
ctgattgagt ttgaaataca acgagacgcg gcgttcttaa ctgagttgca agaaacagcg      540
cttcagtttt gggagttagt acagaccaaa aagaaccgt caaaatgccc tgagcaagat      600
tgttttgttc caagggtga agcccaatac cgttggacat cgctatcacg gcagtattgc      660
tcagcacatg ccgaagtggt ccgactggaa aaccacatta aatctttgaa agaggaaatg      720
cgagaagctc agtcgaaatt ggtcgctatg atgggtaact acgctcatgc cgactatgct      780
ggggtcaaac tcagccgcta catgatggca ggtacggtgg actataagca attggccacc      840
gataagttag gcgagctgga tgaacaggtt ttagctgctt accgaaaagc gccacaagag      900
cggttgcgca ttagcaccaa taagccagag cagcccgttg aaacaccaat caaaatcagc      960
cttgagcaag agaacttggt tctgccaggt gactcgccga gctcatttta cttttaa       1017
```

<210> SEQ ID NO 6
<211> LENGTH: 417
<212> TYPE: DNA
<213> ORGANISM: Unknown
<220> FEATURE:
<223> OTHER INFORMATION: Lamda phage

<400> SEQUENCE: 6

```
atggatatta atactgaaac tgagatcaag caaaagcatt cactaacccc ctttcctgtt       60
ttcctaatca gcccggcatt tcgcgggcga tattttcaca gctatttcag gagttcagcc      120
atgaacgctt attacattca ggatcgtctt gaggctcaga gctgggcgcg tcactaccag      180
cagctcgccc gtgaagagaa agaggcagaa ctggcagacg acatggaaaa aggcctgccc      240
cagcacctgt ttgaatcgct atgcatcgat catttgcaac gccacggggc cagcaaaaaa      300
tccattaccc gtgcgtttga tgacgatgtt gagtttcagg agcgcatggc agaacacatc      360
cggtacatgg ttgaaaccat tgctcaccac caggttgata ttgattcaga ggtataa       417
```

<210> SEQ ID NO 7
<211> LENGTH: 1272
<212> TYPE: DNA
<213> ORGANISM: Saccharomyces cerevisiae

<400> SEQUENCE: 7

```
atgccacaat ttggtatatt atgtaaaaca ccacctaagg tgcttgttcg tcagtttgtg       60
gaaaggtttg aaagaccttc aggtgagaaa atagcattat gtgctgctga actaacctat      120
ttatgttgga tgattacaca taacggaaca gcaatcaaga gagccacatt catgagctat      180
aatactatca taagcaattc gctgagtttc gatattgtca ataaatcact ccagtttaaa      240
tacaagacgc aaaaagcaac aattctggaa gcctcattaa agaattgat tcctgcttgg      300 gaatttacaa ttattcctta ctatggacaa aaacatcaat ctgatatcac tgatattgta      360
agtagtttgc aattacagtt cgaatcatcg gaagaagcag ataagggaaa tagccacagt      420
aaaaaaatgc ttaaagcact tctaagtgag ggtgaaagca tctgggagat cactgagaaa      480
atactaaatt cgtttgagta tacttcgaga tttacaaaaa caaaaacttt ataccaattc      540
ctcttcctag ctactttcat caattgtgga agattcagcg atattaagaa cgttgatccg      600
aaatcattta aattagtcca aaataagtat ctggagagta taatccagtg tttagtgaca      660
```

-continued

```
gagacaaaga caagcgttag taggcacata tacttcttta gcgcaagggg taggatcgat    720
ccacttgtat atttggatga attttgagg aattctgaac cagtcctaaa acgagtaaat    780
aggaccggca attcttcaag caataaacag gaataccaat tattaaaaga taacttagtc    840
agatcgtaca ataaagcttt gaagaaaaat gcgccttatt caatctttgc tataaaaat     900 ggcccaaaat ctcacattgg aagacatttg atgacctcat ttctttcaat gaagggccta    960
acggagttga ctaatgttgt gggaaattgg agcgataagc gtgcttctgc cgtggccagg   1020
acaacgtata ctcatcagat aacagcaata cctgatcact acttcgcact agtttctcgg   1080
tactatgcat atgatccaat atcaaaggaa atgatagcat tgaaggatga gactaatcca   1140
attgaggagt ggcagcatat agaacagcta aagggtagtg ctgaaggaag catacgatac   1200
cccgcatgga atgggataat atcacaggag gtactagact accttctcatc ctacataaat   1260 agacgcatat aa                                                        1272
```

<210> SEQ ID NO 8
<211> LENGTH: 423
<212> TYPE: PRT
<213> ORGANISM: Saccharomyces cerevisiae

<400> SEQUENCE: 8

```
Met Pro Gln Phe Gly Ile Leu Cys Lys Thr Pro Pro Lys Val Leu Val
1               5                   10                  15

Arg Gln Phe Val Glu Arg Phe Glu Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
```

```
                260                 265                 270
Gln Leu Leu Lys Asp Asn Leu Val Arg Ser Tyr Asn Lys Ala Leu Lys
            275                 280                 285
Lys Asn Ala Pro Tyr Ser Ile Phe Ala Ile Lys Asn Gly Pro Lys Ser
        290                 295                 300
His Ile Gly Arg His Leu Met Thr Ser Phe Leu Ser Met Lys Gly Leu
305                 310                 315                 320
Thr Glu Leu Thr Asn Val Val Gly Asn Trp Ser Asp Lys Arg Ala Ser
                325                 330                 335
Ala Val Ala Arg Thr Thr Tyr Thr His Gln Ile Thr Ala Ile Pro Asp
            340                 345                 350
His Tyr Phe Ala Leu Val Ser Arg Tyr Tyr Ala Tyr Asp Pro Ile Ser
        355                 360                 365
Lys Glu Met Ile Ala Leu Lys Asp Glu Thr Asn Pro Ile Glu Glu Trp
370                 375                 380
Gln His Ile Glu Gln Leu Lys Gly Ser Ala Glu Gly Ser Ile Arg Tyr
385                 390                 395                 400
Pro Ala Trp Asn Gly Ile Ile Ser Gln Glu Val Leu Asp Tyr Leu Ser
                405                 410                 415
Ser Tyr Ile Asn Arg Arg Ile
            420

<210> SEQ ID NO 9
<211> LENGTH: 3333
<212> TYPE: DNA
<213> ORGANISM: Unknown
<220> FEATURE:
<223> OTHER INFORMATION: Lamprocystis purpurea

<400> SEQUENCE: 9
atggtatctg gctcaaaggc tggcgtctcg ccacatcgcg aaattgaagt gatgcgccag      60
agcattgatg atcatctggc gggcctgctg ccggaaaccg atagccagga tattgtgagc     120
ctggcgatgc gcgaaggcgt gatggcgccg gcaaacgca ttcgcccgct gctgatgctg      180
ctggcggcgc gcgatctgcg ctatcagggc agtatgccga ccctgctgga tctggcgtgc    240
gcggtggaac tgaccccatac cgcgagcctg atgctggatg atatgccgtg catggataac   300
gcggaactgc cgccgcggcca gccgaccacc cataaaaaat tggcgaaag cgtggcgatt    360
ctggcgagcg tgggcctgct gagcaaagcg tttggcctga ttgcggcgac cggcgatctg    420
ccgggcgaac cgcgcgcgca ggcggtgaac gaactgagca ccgcggtggg cgtgcagggc    480
ctggtgctgg ccagtttcg cgatctgaac gatgcggcgc tggatcgcac cccggatgcg    540
attctgagca ccaaccatct gaaaaccggc attctgttta gcgcgatgct gcagattgtg    600
gcgattgcga gcgcgagcag cccgagcacc cgcgaaaccc tgcacgcgtt tgcgctggat    660
tttggccagg cgtttcagct gctggatgat ctgcgcgatg atcatccgga aaccggcaaa    720
gatcgcaaca aagatgcggg caaaagcacc ctggtgaacc gctgggcgc ggatgcggcg    780
cgccagaaac tgcgcgaaca tattgatagc gcggataaac atctgacctt gcgtgcccg     840
cagggcggcg cgattcgcca gtttatgcat ctgtggtttg ccatcatct ggcggattgg     900
agcccggtga tgaaaattgc gtaaatgtcc caacccccct gctagacca cgcaacccag    960
acgatggcga acggcagcaa gagctttgcg accgcggcga aactgtttga tccggcgacc  1020
cgccgcagcg tgctgatgct gtatacctgg tgccgccatt gcgatgatgt gattgatgat  1080
cagacgcatg gctttgcgag cgaagcggcg gcggaagaag aagcgaccca gcgcctggcg  1140
```

```
cgcctgcgca ccctgaccct ggcggcgttt gaaggcgcgg aaatgcagga cccggcgttt      1200
gcggcgtttc aggaagtggc gctgacccac ggcattaccc cgcgcatggc gctggatcat      1260
ctggatggct ttgcgatgga tgtggcgcag acccgctatg tgacctttga agatacccty      1320
cgctattgct atcatgtggc gggcgtggtg ggcctgatga tggcgcgcgt gatgggcgtg      1380
cgcgatgaac gcgtgctgga tcgcgcgtgc gatctgggcc tggcgtttca gctgaccaac      1440
attgcgcgcg atattattga tgatgcgcg attgatcgct gctatctgcc ggcggaatgg       1500
ctgcaggatg cgggcctgac cccggaaaac tatgcggcgc gcgaaaaccg cgcggcgctg      1560
gcgcgcgtgg cggaacgcct gattgatgcg gcggaaccgt attatattag cagccaggcg      1620
ggcctgcatg atctgccgcc gcgctgcgcg tgggcgattg cgaccgcgcg cagcgtgtat      1680
cgcgaaattg gcattaaagt gaaagcggcg ggcggcagcg cgtgggatcg ccgccagcat      1740
accagcaaag gcgaaaaaat tgcgatgctg atggcggcgc cgggccaggt gattcgcgcg      1800
aaaaccaccc gcgtgacccc gcgcccggcg ggcctgtggc agcgcccggt gtaaatgaaa      1860
aaaacggttg tgatcggcgc tgggttcggc ggcctggcgc tggcgattcg cctgcaggcg      1920 gcggcattc cgaccgtgct gctggaacag cgcgataaac cgggcggccg cgcgtatgtg       1980
tggcatgatc agggctttac ctttgatgcg ggcccgaccg tgattaccga tccgaccgcg      2040
ctggaagcgc tgtttaccct ggcgggccgc cgcatggaag attatgtgcg cctgctgccg      2100
gtgaaaccgt tttatcgcct gtgctgggaa agcggcaaaa ccctggatta tgcgaacgat      2160
agcgcggaac tggaagcgca gattacccag tttaacccgc gcgatgtgga aggctatcgc      2220
cgctttctgg cgtatagcca ggcggtgttt caggaaggct atctgcgcct gggcagcgtg      2280
ccgtttctga gctttcgcga tatgctgcgc gcgggcccgc agctgctgaa actgcaggcg      2340
tggcagagcg tgtatcagag cgtgagccgc tttattgaag atgaacatct gccaggcg      2400 tttagctttc atagcctgct ggtgggcggc aacccgttta ccaccagcag catttatacc      2460
ctgattcatg cgctggaacg cgaatggggc gtgtggtttc cggaaggcgg caccggcgcg      2520
ctggtgaacg gcatggtgaa actgtttacc gatctgggcg cgaaattga actgaacgcg       2580 cgcgtggaag aactggtggt ggcggataac cgcgtgagcc aggtgcgcct ggcggatggc      2640 cgcattttg ataccgatgc ggtggcgagc aacgcggatg tggtgaacac ctataaaaaa       2700
ctgctgggcc atcatccggt gggccagaaa cgcgcggcgg cgctggaacg caaaagcatg      2760
agcaacagcc tgtttgtgct gtatttggc ctgaaccagc cgcatagcca gctggcgcat       2820
cataccattt gctttggccc cgcgctatcgc gaactgattg atgaaattt taccggcagc      2880 gcgctggcgg atgattttag cctgtatctg catagcccgt gcgtgaccga tccgagcctg      2940
gcgccgccgg gctgcgcgag ctttatgtg ctggcgccgg tgccgcatct gggcaacgcg       3000
ccgctggatt gggcgcagga aggcccgaaa ctgcgcgatc gcattttga ttatctggaa       3060 gaacgctata tgccgggcct gcgcagccag ctggtgaccc agcgcatttt taccccggcg      3120
gattttcatg ataccctgga tgcgcatctg gcagcgcgt ttagcattga accgctgctg       3180
acccagagcg cgtggtttcg cccgcataac cgcgatagcg atattgcgaa cctgtatctg      3240
gtgggcgcgg gcacccatcc gggcgcgggc attccgggcg tggtggcgag cgcgaaagcg      3300
accgcgagcc tgatgatcga agacctgcag taa                                   3333
```

<210> SEQ ID NO 10
<211> LENGTH: 549
<212> TYPE: DNA

<213> ORGANISM: Escherichia coli

<400> SEQUENCE: 10

```
atgcagaccg aacatgtgat tctgctgaac gcgcagggcg tgccgaccgg cacgctggaa      60
aaatatgcgg cgcataccgc ggatacccgc ctgcatctgg cgtttagcag ctggctgttt     120
aacgcgaaag gccagctgct ggtgacccgc cgcgcgctga gcaaaaaagc gtggccgggc     180
gtgtggacca acagcgtgtg cggccatccg cagctgggcg aaagcaacga agatgcggtg     240
attcgccgct gccgctatga actgggcgtg gaaattaccc cgccggaaag catttatccg     300
gattttcgct atcgcgcgac cgatccgagc ggcattgtgg aaaacgaagt gtgcccggtg     360
tttgcggcgc gcaccaccag cgcgctgcag attaacgatg atgaagtgat ggattatcag     420
tggtgcgatc tggcggatgt gctgcatggc attgatgcga ccccgtgggc gtttagcccg     480
tggatggtga tgcaggcgac caaccgcgaa gcgcgcaaac gcctgagcgc gtttacccag     540
ctgaaataa                                                             549
```

<210> SEQ ID NO 11
<211> LENGTH: 900
<212> TYPE: DNA
<213> ORGANISM: Escherichia coli

<400> SEQUENCE: 11

```
atggatttcc cgcagcagct ggaagcgtgt gtgaaacagg cgaaccaggc gctgagccgc      60
tttattgcgc cgctgccgtt tcagaacacc ccggtggtgg aaaccatgca gtatggcgcg     120
ctgctgggcg caaacgcct gcgcccgttt ctggtgtatg cgaccggcca catgtttggc     180
gtgagcacca cacccctgga tcgccggcg gcggcggtgg aatgcattca tgcgtatagc     240
ctgattcatg atgatctgcc ggcgatggat gatgatgatc tgcgccgcgg cctgccgacc     300
tgccatgtga atttggcga agcgaacgcg attctggcgg gcgatgcgct gcagaccctg     360
gcgtttagca ttctgagcga tgcggatatg ccggaagtga gcgatcgcga tcgcattagc     420
atgattagcg aactggcgag cgcgagcggc attgcgggca tgtgcggcgg ccaggcgctg     480
gatctggatg cggaaggcaa acatgtgccg ctggatgcgc tggaacgcat tcatcgccat     540
aaaaccggcg cgctgattcg cgcggcgtg cgcctgggcg cgctgagcgc gggcgataaa     600
ggccgccgcg cgctgccggt gctggataaa tatgcggaaa gcattggcct ggcgtttcag     660
gtgcaggatg atattctgga tgtggtgggc gataccgcga ccctgggcaa acgccagggc     720
gcggatcagc agctgggcaa aagcacctat ccggcgctgc tgggcctgga acaggcgcgc     780
aaaaaagcgc gcgatctgat tgatgatgcg cgccagagcc tgaaacagct ggcggaacag     840
agcctggata ccagcgcgct ggaagcgctg gcggattata ttattcagcg caacaaataa     900
```

<210> SEQ ID NO 12
<211> LENGTH: 1863
<212> TYPE: DNA
<213> ORGANISM: Escherichia coli

<400> SEQUENCE: 12

```
atgagttttg atattgccaa ataccccgacc ctggcactgg tcgactccac ccaggagtta     60
cgactgttgc cgaaagagag tttaccgaaa ctctgcgacg aactgcgccg ctatttactc     120
gacagcgtga gccgttccag cgggcacttc gcctccgggc tgggcacggt cgaactgacc     180
gtggcgctgc actatgtcta caacacccg tttgaccaat tgatttggga tgtggggcat     240
caggcttatc cgcataaaat tttgaccgga cgccgcgaca aaatcggcac catccgtcag     300
```

```
aaaggcggtc tgcacccgtt cccgtggcgc ggcgaaagcg aatatgacgt attaagcgtc      360
gggcattcat caacctccat cagtgccgga attggtattg cggttgctgc cgaaaaagaa      420
ggcaaaaatc gccgcaccgt ctgtgtcatt ggcgatggcg cgattaccgc aggcatggcg      480
tttgaagcga tgaatcacgc gggcgatatc cgtcctgata tgctggtgat tctcaacgac      540
aatgaaatgt cgatttccga aaatgtcggc gcgctcaaca accatctggc acagctgctt      600
tccggtaagc tttactcttc actgcgcgaa ggcgggaaaa agttttctc tggcgtgccg       660 ccaattaaag agctgctcaa cgcaccgaa gaacatatta aaggcatggt agtgcctggc       720
acgttgtttg aagagctggg ctttaactac atcggcccgg tggacggtca cgatgtgctg      780
gggcttatca ccacgctaaa gaacatgcgc gacctgaaag ccccgcagtt cctgcatatc      840
atgaccaaaa aaggtcgtgg ttatgaaccg gcagaaaaag acccgatcac tttccacgcc      900
gtgcctaaat tgatccctc cagcggttgt ttgccgaaaa gtagcggcgg tttgccgagc       960
tattcaaaaa tctttggcga ctggttgtgc gaaacggcag cgaaagacaa caagctgatg     1020
gcgattactc cggcgatgcg tgaaggttcc ggcatggtcg agttttcacg taaattcccg     1080
gatcgctact tcgacgtggc aattgccgag caacacgcgg tgacctttgc tgcgggtctg     1140
gcgattggtg ggtacaaacc cattgtcgcg atttactcca cttttcctgca acgcgcctat    1200 gatcaggtgc tgcatgacgt ggcgattcaa aagcttccgg tcctgttcgc catcgaccgc     1260
gcgggcattg ttggtgctga cggtcaaacc catcagggtg cttttgatct ctcttacctg     1320
cgctgcatac cggaaatggt cattatgacc ccgagcgatg aaaacgaatg tcgccagatg     1380
ctctataccg gctatcacta taacgatggc ccgtcagcgg tgcgctaccc gcgtggcaac     1440
gcggtcggcg tggaactgac gccgctggaa aaactaccaa ttggcaaagg cattgtgaag     1500
cgtcgtggcg agaaactggc gatccttaac tttggtacgc tgatgccaga gcggcgaaa     1560 gtcgccgaat cgctgaacgc cacgctggtc gatatgcgtt ttgtgaaacc gcttgatgaa     1620
gcgttaattc tggaaatggc cgccagccat gaagcgctgg tcaccgtaga agaaaacgcc     1680
attatgggcg gcgcaggcag cggcgtgaac gaagtgctga tggcccatcg taaaccagta    1740
cccgtgctga acattggcct gccggacttc tttattccgc aaggaactca ggaagaaatg    1800 gcgcgccgaac tcggcctcga tgccgctggt atggaagcca aaatcaaggc ctggctggca    1860
taa                                                                 1863

<210> SEQ ID NO 13
<211> LENGTH: 780
<212> TYPE: DNA
<213> ORGANISM: Enterobacter aerogenes

<400> SEQUENCE: 13
atgaatcatg cttcagattg cacctgtgaa gagagtctgt gtgaaacgct acgcgcgttt       60
tccgctcagc atcccgatag cgtgctgtat caaacttcgc tgatgagcgc cctgctcagc      120
ggcgtctacg aaggtaccac caccattgcg gacctgctga agcacggtga tttcgggctc      180
ggcactttta tgaactcga cggcgagctg atcgcgttta gcagccaggt ttatcaactg      240
cgtgccgacg gcagcgcgcg taagcgcgt ccggaacaga aaacgccgtt tgcggtgatg       300
acctggtttc agccgcagta ccgtaaaacc tttgaccatc cggtcagccg ccagcagctg      360
catgaggtta ttgaccagca aattccttcc gacaatctgt tctgcgcgct gcgaatcgat      420
ggtcatttcc gccacgccca tacccgcacc gtgcctcgtc agacgccgcc ctaccgggcg      480
```

| | |
|---|---|
| atgaccgacg tgctcgacga tcagccggtt ttccgcttta accagcgtga cggcgtactg | 540 |
| gtcggttttc gtaccccgca gcatatgcag ggaattaacg tcgccggcta tcacgaacac | 600 |
| ttcattaccg atgaccgcca gggcggcggc cacctgctgg actaccagct cgaccatggg | 660 |
| gtattgacct tcggcgaaat tcataagctg atgatcgacc ttcccgccga cagcgcgttc | 720 |
| ctgcaggcca atttgcatcc cgataatctc gatgccgcca tccgttcagt agaaagttag | 780 |

<210> SEQ ID NO 14
<211> LENGTH: 771
<212> TYPE: DNA
<213> ORGANISM: Enterobacter aerogenes

<400> SEQUENCE: 14

| | |
|---|---|
| atgaaaaaag tcgcacttgt caccggcgcc ggtcagggca ttggtaaagc tatcgcgtta | 60 |
| cgcctcgtga aggacggttt tgccgtggcg atcgccgatt acaatgacgt cacagcgaaa | 120 |
| gccgtggcgg atgaaatcaa ccagcacggc ggccgggcaa tcgcggtcaa agtcgatgtt | 180 |
| tccgaccgtg agcaggtgtt tgccgccgtc gaacaggcgc gaaaaacgct gggcggattc | 240 |
| aacgtcatcg tcaataacgc cggggtcgcg ccatcaacgc ctatcgaatc cattacgccg | 300 |
| gagattgtcg acaaggtcta caacatcaac gttaaagggg tgatctgggg gattcaggcg | 360 |
| gcagtcgagg cctttaaaaa agaggggcac ggcggcaaaa tcatcaacgc ctgttcgcag | 420 |
| gccggacacg tcgcaacccc ggaactggcg gtctacagct cgagcaaatt cgccgtacgc | 480 |
| ggtttaacgc aaaccgccgc tcgcgacctg gcgccgctgg gtattaccgt taacggctac | 540 |
| tgcccggggga ttgtgaaaac gccgatgtgg gccgagatcg atcgtcaggt atccgaagcg | 600 |
| gcgggtaaac tctctgggcta cgggacagcc gaattcgcca aacgcatcac cctcggccgc | 660 |
| ctgtctgagc cagaagatgt cgccgcctgc gtctcttatc tcgccagccc ggattccgat | 720 |
| tatatgaccg gtcaatcgct gctgatcgat ggcgggatgg tattcaatta a | 771 |

<210> SEQ ID NO 15
<211> LENGTH: 1680
<212> TYPE: DNA
<213> ORGANISM: Enterobacter aerogenes

<400> SEQUENCE: 15

| | |
|---|---|
| atggacaaac agtatccgca gcgccagtgg gcgcacggcg ccgatctggt cgtcagccaa | 60 |
| ctggaagcgc aaggcgtacg gcaggtcttc gggatccccg gcgctaaaat cgataaggtt | 120 |
| ttcgactcgt tgctggactc ctcaatccgc attattccgg tacgtcacga ggccaacgcc | 180 |
| gcctttatgg ccgccgcggt cggcgcatt accggcaaag cgggcgtcgc gctggtgacc | 240 |
| tccggacccg gttgttccaa cctgataacc gggatggcca ccgccaatag cgaaggcgac | 300 |
| ccggtggtgg cgctgggcgg cgcggtcaaa cgcgcggata aagccaaaca ggtacaccag | 360 |
| agtatggaca cggtggcgat gttcagcccg gtcaccaaat acgcggtaga agtgaccctcg | 420 |
| ccggatgcgc tggcggaagt ggtttctaac gcttttcgcg ccgccgagca gggtcgcccg | 480 |
| ggcagcgcct tcgtcagtct gccgcaggat gtggtcgatg gtccggtgac cggcaaagtc | 540 |
| ctgccccgcca gcagcgcgcc gcagatgggc gccgcgcctg acgaggcaat caatcaggtt | 600 |
| gcgaagttga ttgcccaggc gaagaatccg gtgttcctgc ttggattaat ggccagccag | 660 |
| acggaaaaca gcgccgcgct gcatcgtttg ctggaaacca gccatattcc ggtcaccagc | 720 |
| acctatcagg ccgccggggc ggtcaatcag gataacttct cgcgcttcgc cgggcgcgtc | 780 |
| gggctgtttta acaatcaggc cggtgaccgc ttattgcaac tggccgacct ggttatctgc | 840 |

```
atcggctata gcccggtgga atacgaaccg gcgatgtgga acagcggcaa cgcgacgctg    900
gtacatatcg acgtactgcc cgcctatgaa gagcgtaact acacgccgga tgtcgagctg    960
gtgggcgaca tcgccggcac gctgaacaag ctggcgcaaa atatcgatca tcggctggtg   1020
ctctcgccgc aggctgctga aatcctccac gaccgccagc atcagcggga actgcttgac   1080
cgccgcggag cgcagttgaa tcagtttgcc ctgcacccgc tgcgtatcgt tcgcgccatg   1140
caggatatcg tcaacagcga cgtcacgctg acggtcgata tggggagctt ccatatctgg   1200
atcgcccgct atctctacag cttccgcgcc cgtcaggtga tgatctccaa cggtcagcag   1260
accatgggcg tcgccctgcc gtgggccatc ggggcctggc tggtcaatcc gcagcgcaaa   1320
gtggtctcgg tctccggcga tggcggtttt ctgcaatcca gcatggagct ggaaacggcg   1380
gtccgcctga agccaacat cctgcatctt atctgggtcg ataacggcta caacatggtc   1440
gccatccagg aagagaaaaa atatcaacgc ctgtccggcg tcgagttcgg tcctatggat   1500
tttaaagcct atgccgaatc cttcggcgcg aaagggtttg cggtggaaag cgctgaggcg   1560
ctggagccga cgctacgcgc ggcgatggac gtcgacggcc cggcggtggt cgccatcccc   1620
gtggattacc gtgataaccc gctgctgatg ggccagctac acctgagtca aattctttaa   1680

<210> SEQ ID NO 16
<211> LENGTH: 873
<212> TYPE: DNA
<213> ORGANISM: Unknown
<220> FEATURE:
<223> OTHER INFORMATION: Vibrio sp. dhg

<400> SEQUENCE: 16
atggctcacg gctgcgaagt cgtctgtgca tttgttaacg atgatctgtc agaacccgtt     60
ttaaaacagc tatctcaggg cgggactaag cttatagcga tgcgttgtgc gggatttgat    120
aaggtcgacc aacaagcggc taagaagcta ggcttgcaag tagtacatgt gcccgcctat    180
tcacctgaag cggttgccga acatacggtt ggtatgatga tgtgtctaaa ccgtcgacta    240
cacaaagcct atcagcgaac ccgggatgcg aatttctctc tggaaggttt agttggcttc    300 aactttttg gtaagactgt agggtaata ggtacggaa aaatcggcat tgctgcgatg    360 agaatttta agggattagg catggaaatt cttttgccatg atccttacga aaacccactg    420
gcaatagaga tgggcgcacg ttactgctct cttgaagata tatacgccaa tgcggatatt    480
attactttgc attgcccgat gagtaaagaa aactaccacc tcctcaatgc cgactcattt    540
tcgaaaatga aagatggggt gatgatcatt aatacgagtc gtggagagct attggattct    600
gtagcagcaa tcgaagcgct aaaacaaggc agaatcggct cactaggctt ggatgtgtac    660
gacaatgaaa aagagttgtt cttccaggat aaatcaaacg acattatcgt agacgatgtt    720
ttccgccgac tgtcggcatg tcataacgtg ctgttcacgg tcatcaagc tttcttaact    780 cacgaagcgc tcaacaacat cgcgtcagtg acactaaata cgtagaagt attcttctct    840 gggcaagttt caggcaatga actgatcaac taa                                  873

<210> SEQ ID NO 17
<211> LENGTH: 1806
<212> TYPE: DNA
<213> ORGANISM: Unknown
<220> FEATURE:
<223> OTHER INFORMATION: Vibrio sp. dhg

<400> SEQUENCE: 17
```

```
gtgcaaatta tcaccacaga tatcgcagtc atcggcgctg gcggcgctgg tcttcgtact    60
gctattgcag cggcagaggc aaacccagat ttagaagtcg ctctgatttc taaagtttat   120
cctatgcgct cacacacggt cgcagcggag ggtggctcag cagcagttat caaggatgaa   180
gatagcttag ataaccactt caacgatacg gttggcggtg cgactggct atgtgaacag    240 gacgtcgttg aatattttgt agaaaacgca acccgcgaaa tgatccaaat ggaacaatgg   300
ggttgtcctt ggagccgtaa agagaacggg gaagttaacg ttcgccgctt tggcggtatg   360
aaggttgaac gaacttggtt tgcagcggat aaaaccggct tccatatgct tcacaccta    420 ttccaaactt caatgaagta cagcaacatc aaacgttttg atgagtactt tgtgttggat   480
ctgcttgttg acgatggtga agtacaaggt ctgatcgcca ttcacatgtc tgaaggtgag   540
ttggtcacca tcaaagcgaa atctgttgtg cttgcgactg gtggcgcggg acgtgtttac   600
cactgtaaca ccaatggcgg tatcgtaacg ggcgatggca tggcgatggc ttaccgtcac   660
ggtgttccgc tacgtgatat ggaatttgtt caataccacc ctactggcct accaggtact   720
ggtatcctaa tgacagaagg ttgtcgtggt gaaggtggta ttattgtcaa caaaaacggc   780
taccgctacc tacaagacta cggcatgggc cctgaaactc cagtgggtca accgaaaaac   840
aaatacatgg aactgggtcc acgtgacaaa gtttctcaag cttctctggca tgagcaacag   900 aaaggcaaca ccatcaaaca cccactgggt gacgtggtgc acctagacct tcgccacctt   960
ggtgaagagt acctacaaga acgtttacct ttcatctgtg agctagcaaa agcttacgtg  1020
aacgttgatc ctgcaaaaga accaattcca attcgtccga ccgtgcacta caccatgggc  1080
ggcatcgaaa ctgatggtgg ctgtgagact cgcgttaaag gtctattcgc agttggtgag  1140
tgtgcgtcag ttggtctgca tggtgcgaac cgtcttggct ctaactctct ggctgagttc  1200
gtggtatttg ccgagttgc gggtgaaaac gcagtgaaac gtgcagcaga attcaaaggc   1260
tggaacgaca atgctatcgc agctcaagtg aaagctgttg aagaacgcat tgccagctta   1320
atgaaccaag aaggcgatga aaactgggca gacatccgta ccgaaatggg ccacaccatg   1380
gaagcgggtt gtggcatcta ccgccaagaa gatctgatgc aagcaaccat cgataagatc   1440
acggaactta acaacgttta caaacgcatt agcatcaaag acaaaggcaa agtgttcaac   1500
actgaccttc tttacgcaat cgaagtcggt tacggcctag aagtggcaga agcgatggtt   1560
cactctgcaa tcctgcgcaa agaatctcgc ggtgcacacc aacgtctcga tgatggctgc   1620
actgaacgtg acgacgtgaa cttcctgaaa cactcacttg ctttctatca accagacgca   1680
gcgcctagca tcgactacag caatgtaacc attactaagt ctcagcctaa agcgcgtcta   1740
tacggtgaag ctgcagaaaa agccgcagca gaagaagcag cgaagaacgc agaggagcaa   1800
gcataa                                                            1806
```

<210> SEQ ID NO 18
<211> LENGTH: 747
<212> TYPE: DNA
<213> ORGANISM: Unknown
<220> FEATURE:
<223> OTHER INFORMATION: Vibrio sp. dhg

<400> SEQUENCE: 18

```
atgtcagcaa accgcatcca gaaagtagac attctgcgtt atgacccaga aaaagacgca    60
gaaccgcact acaaactttt cgaagtacca ttcgatgaaa ctatgtctgt gctcgacgcg   120
attggttaca tcaaagataa cctagacaaa gacttatctt accgttggtc ttgtcgtatg   180
gcgatctgtg gctcatgcgg catcatggtt aatggtgtgc ctaagctagc ttgtaagagc   240
```

```
ttcttacgtg actaccaaaa tggtctgaaa atcgagccat tagcgaattt cccgattgag      300
aaagacttga tcgttgatat gacgccattt atcgagcgtc ttgaagcgat caaaccttac      360
atcattggta acgaccgtaa acctgaagac ggcacaaact tgcaaacgcc agagcaaatg      420
gcgaagtaca agcagtttgc tggttgtatc aactgtggtc tgtgttacgc agcgtgtcct      480
cagttcggtc tcaacccaga gttcatcggc ccggcagcgc taacattggc gaccgttac       540 aacttagaca gtcgtgataa cggtaaagct gagcgtatga agctgattaa cggtgagaat      600
ggcgcctggg gttgtacgtt tgtaggttac tgttctgagg tttgtccaaa gagcgttgac      660
cctgcagcag cagtaaacca aggcaaagta gagtcttcta tggacttcgt aattgcgatg      720
ctgaaacctc aggaggcaga aggatga                                         747
```

<210> SEQ ID NO 19
<211> LENGTH: 384
<212> TYPE: DNA
<213> ORGANISM: Unknown
<220> FEATURE:
<223> OTHER INFORMATION: Vibrio sp. dhg

<400> SEQUENCE: 19

```
atgagtaacc gtaaacctta cgttcgtgaa gtaaaacgca cttggtggaa ggaccatcct       60
ttctaccgct tctacatgtt acgtgaagcg acggtactgc cactgattct attcaccatc      120
ttcctgactt tcggcctggg ttcactagtg aaagggcctg aagcttggca aggctggtta      180
gagttcatgg caaacccaat cgtagtcgcg atcaacatcg ttgcgctact tggaagcctg      240
ttccacgcac aaaccttctt cagcatgatg ccacaggtga tgccaattcg cctaaaaggc      300
aaacctgtgg gtaagaatat catcgtactg actcagtggg cagcggtcgc gtttatctca      360
ctgatcgttc tcatcgtggt gtaa                                             384
```

<210> SEQ ID NO 20
<211> LENGTH: 378
<212> TYPE: DNA
<213> ORGANISM: Unknown
<220> FEATURE:
<223> OTHER INFORMATION: Vibrio sp. dhg

<400> SEQUENCE: 20

```
atgaaaccaa attatagtgt aaacacagca ccaaaacgtt cagatgagcc aatctggtgg       60
ggactgtttg gtgcaggcgg tacctggttt gcgatgatca ctcctatcac cgtacttgta      120
cttggtatcc tcgttccact gggcgtgatt gatgcagacg ccatgagcta cgagcgagta      180
tctgaattcg cgaccagtat cattggtgcg ctatttatca tcggtacact agcgctgcca      240
atgtggcatg caatgcaccg tgttcaccac ggcatgcacg accttaagtt ccacactggt      300
gtggtgggaa aagtggcatg ctatgcgttc gctggcctta tcagtgcgct atcagttatc      360
tttatcttca tgatttaa                                                    378
```

<210> SEQ ID NO 21
<211> LENGTH: 2277
<212> TYPE: DNA
<213> ORGANISM: Unknown
<220> FEATURE:
<223> OTHER INFORMATION: Vibrio sp. dhg

<400> SEQUENCE: 21

```
atggcagagc aatttgctaa agcttgggaa ggttttgctg caggtgattg gcaaaacgaa       60
```

```
gtaaacgttc gtgatttcat tcagaagaac tacactccgt acgaaggcga cgaatctttc      120
ctagtttctg aaggtactga agcaacaaac aagctttggg ctaaagtaat ggaaggtatc      180
aaacaagaga acgcgactca cgctcctgtt gattttgata catctgttat ctctaccatc      240
actgctcacg atgcaggcta catcgaaaaa gatcttgaaa ctatcgtagg tctacaaact      300
gaagcgcctc taaaacgtgc gatcatccct aacggtggta ttcgcatggt tgaaggttca      360
tgcaaagcat atgaccgcga actagaccca caagttaaga aaatcttcac agaataccgt      420
aaaacacaca atgctggtgt tttcgatatc tacactcctg atatccttgc atgtcgtaag      480
tctggtgtac taactggtct tcctgacgca tacggccgtg tcgtatcat cggtgactac       540
cgtcgcgttg cgctttacgg tatcgacttc ctaatgaagg acaaactagc tcagttcact      600
tctctacaag agaaatttga gaacggcgaa gaccttcaca tgactatgca acttcgtgaa      660
gaaattgcag agcagcaccg cgctctaggt caaatcaaac aaatggctgc gaaatacggt      720
ttcgatattt ctcgccctgc tgaaactgca caagaagcta tccaatggac ttacttcggc      780
tacctagctg ctgttaagtc tcaaaacggt gctgcaatgt ctctaggtcg tacttctaca      840
ttcctagacg tgtacatcga gcgtgatatc gctgcaggta agatcactga agatcaagct      900
caagaaatga tcgaccactt cgtaatgaaa ctacgtatgg ttcgtttcct acgtactcct      960
gagtacgatg agctattctc tggcgaccca atttgggcaa cagaatcaat gggtggtatg     1020
ggtcttgacg tcgtacgct agtaacgcgt tctaacttcc gtttcctaaa cagcctatac      1080
actatgggtc cttctccaga gccaaacatc actgttcttt ggtctgaagc acttccagat     1140
ggtttcaaac gtttctgtgc aaaagtatct atcgatactt cttctatcca gtacgaaaac     1200
gacgatctga tgcgtccaga catggaatca gacgattacg ctatcgcttg ttgtgtatct     1260
ccaatggttt ttggtaagca aatgcagttc ttcggtgctc gtgcgaacct tgctaaaact     1320
atgctttaca ccatcaacgg cggtatcgat gagaagctga agatccaagt tggtcctaag     1380
atggacaaga tcgaaggtga ataccctaga tacaacgagc tatgggaaaa aatggatcac     1440
ttcatggatt ggttagctaa gcagtacgtg actgcactaa acagcatcca cttcatgcac     1500
gacaagtaca gctacgaagc gtctctaatg gctctacatg accgtgacgt taaacgtaca     1560
atggcttgtg gtatcgctgg tctatctgtt gctgctgact ctctatcagc aatcaaatac     1620
gcgaaagtta aaccagttcg tgacgaagat ggtctagcaa tcgactttga aatcgaaggc     1680
gattacccta aattcggtaa caacgacgct cgcgtagatg acatcgcttg tgaacttgtt     1740
tctgtatttta tgaacaagat ccgtgagctt aagacttacc gtgatgctat ccctactcag     1800
tctatcctga ctatcacttc aaacgtggta tacggtaaga agactggtaa cacgcctgat     1860
ggtcgtcgtg ctggtactcc atttgcgcca ggtgcaaacc caatgcacgg ccgtgatgag     1920
aaaggtgcag tagcatcatt gacttcagta gcgaaactac cgtttgctga cgctcaagat     1980
ggtatctctt acacattctc tatcgtgcca aatgcactag gtaaagaaga gactagccaa     2040
cgtgctaacc ttgcaggcct aatggatggt tacttccacc acgaagctgg catcgaaggt     2100
ggccaacacc taaacgtgaa cgtgcttaac cgcgaaactc tagaagacgc agttaaacac     2160
ccagagaaat accctcagct aactatccgt gtatcgggtt acgctgtacg tttcaactct     2220
ctgactgctg aacagcaagc tgacgttatc gctcgtacat tcactgaatc actataa      2277
```

<210> SEQ ID NO 22
<211> LENGTH: 35
<212> TYPE: DNA
<213> ORGANISM: Artificial Sequence

```
<220> FEATURE:
<223> OTHER INFORMATION: Synthetic 5' UTR
<220> FEATURE:
<221> NAME/KEY: misc_feature
<222> LOCATION: (1)..(6)
<223> OTHER INFORMATION: promoter
<220> FEATURE:
<221> NAME/KEY: misc_feature
<222> LOCATION: (26)..(29)
<223> OTHER INFORMATION: promoter

<400> SEQUENCE: 22
nnnnnngcta gctcagtcct aggkannnng ctagc                               35

<210> SEQ ID NO 23
<211> LENGTH: 35
<212> TYPE: DNA
<213> ORGANISM: Artificial Sequence
<220> FEATURE:
<223> OTHER INFORMATION: promoter

<400> SEQUENCE: 23
cttatggcta gctcagtcct agggacagtg ctagc                               35

<210> SEQ ID NO 24
<211> LENGTH: 35
<212> TYPE: DNA
<213> ORGANISM: Artificial Sequence
<220> FEATURE:
<223> OTHER INFORMATION: promoter

<400> SEQUENCE: 24
tttacggcta gctcagtcct agggatagtg ctagc                               35

<210> SEQ ID NO 25
<211> LENGTH: 35
<212> TYPE: DNA
<213> ORGANISM: Artificial Sequence
<220> FEATURE:
<223> OTHER INFORMATION: promoter

<400> SEQUENCE: 25
ctgacggcta gctcagtcct agggatagtg ctagc                               35

<210> SEQ ID NO 26
<211> LENGTH: 35
<212> TYPE: DNA
<213> ORGANISM: Artificial Sequence
<220> FEATURE:
<223> OTHER INFORMATION: promoter

<400> SEQUENCE: 26
ttgatggcta gctcagtcct agggattatg ctagc                               35

<210> SEQ ID NO 27
<211> LENGTH: 35
<212> TYPE: DNA
<213> ORGANISM: Artificial Sequence
<220> FEATURE:
<223> OTHER INFORMATION: promoter

<400> SEQUENCE: 27
ttgatggcta gctcagtcct aggtacagtg ctagc                               35

<210> SEQ ID NO 28
<211> LENGTH: 35
<212> TYPE: DNA
```

```
<213> ORGANISM: Artificial Sequence
<220> FEATURE:
<223> OTHER INFORMATION: promoter

<400> SEQUENCE: 28
ttgatggcta gctcagtcct aggtattgtg ctagc                              35

<210> SEQ ID NO 29
<211> LENGTH: 35
<212> TYPE: DNA
<213> ORGANISM: Artificial Sequence
<220> FEATURE:
<223> OTHER INFORMATION: promoter

<400> SEQUENCE: 29
ttgatggcta gctcagtcct aggtactatg ctagc                              35

<210> SEQ ID NO 30
<211> LENGTH: 35
<212> TYPE: DNA
<213> ORGANISM: Artificial Sequence
<220> FEATURE:
<223> OTHER INFORMATION: promoter

<400> SEQUENCE: 30
ttgacggcta gctcagtcct aggtactgtg ctagc                              35

<210> SEQ ID NO 31
<211> LENGTH: 35
<212> TYPE: DNA
<213> ORGANISM: Artificial Sequence
<220> FEATURE:
<223> OTHER INFORMATION: promoter

<400> SEQUENCE: 31
ttgatggcta gctcagtcct aggtacaatg ctagc                              35

<210> SEQ ID NO 32
<211> LENGTH: 35
<212> TYPE: DNA
<213> ORGANISM: Artificial Sequence
<220> FEATURE:
<223> OTHER INFORMATION: promoter

<400> SEQUENCE: 32
ttgatggcta gctcagtcct aggtatagtg ctagc                              35

<210> SEQ ID NO 33
<211> LENGTH: 35
<212> TYPE: DNA
<213> ORGANISM: Artificial Sequence
<220> FEATURE:
<223> OTHER INFORMATION: promoter

<400> SEQUENCE: 33
ttgatggcta gctcagtcct aggtacaatg ctagc                              35

<210> SEQ ID NO 34
<211> LENGTH: 35
<212> TYPE: DNA
<213> ORGANISM: Artificial Sequence
<220> FEATURE:
<223> OTHER INFORMATION: promoter

<400> SEQUENCE: 34
ttgatggcta gctcagtcct aggtataatg ctagc                              35
```

```
<210> SEQ ID NO 35
<211> LENGTH: 35
<212> TYPE: DNA
<213> ORGANISM: Artificial Sequence
<220> FEATURE:
<223> OTHER INFORMATION: promoter

<400> SEQUENCE: 35
ttgacggcta gctcagtcct aggtacagtg ctagc                    35

<210> SEQ ID NO 36
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 36
acggagawtg ctyaaksagt csttt                               25

<210> SEQ ID NO 37
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 37
acggagattg cttaagcagt cgttt                               25

<210> SEQ ID NO 38
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 38
acggagaatg cttaatcagt cgttt                               25

<210> SEQ ID NO 39
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 39
acggagattg cttaatcagt ccttt                               25

<210> SEQ ID NO 40
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 40
acggagattg cttaagcagt cgttt                               25

<210> SEQ ID NO 41
<211> LENGTH: 25
<212> TYPE: DNA
<213> ORGANISM: Artificial Sequence
<220> FEATURE:
```

<223> OTHER INFORMATION: Synthetic 5' UTR

<400> SEQUENCE: 41
acggagaatg ctcaatgagt cgttt                                          25

<210> SEQ ID NO 42
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 42
acggagattg cttaatgagt cgttt                                          25

<210> SEQ ID NO 43
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 43
acggagaatg cttaatgagt cgttt                                          25

<210> SEQ ID NO 44
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 44
acggagaatg cttaatgagt cgttt                                          25

<210> SEQ ID NO 45
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 45
acggagattg cttaatgagt cgttt                                          25

<210> SEQ ID NO 46
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 46
acggagaatg ctcaaggagt cgttt                                          25

<210> SEQ ID NO 47
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 47
acggagattg cttaaggagt cgttt                                          25

```
<210> SEQ ID NO 48
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 48
acggagattg cttaaggagt ccttt                                           25

<210> SEQ ID NO 49
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 49
acggagaatg cttaaggagt cgttt                                           25

<210> SEQ ID NO 50
<211> LENGTH: 25
<212> TYPE: DNA
<213> ORGANISM: Artificial Sequence
<220> FEATURE:
<223> OTHER INFORMATION: Synthetic 5' UTR

<400> SEQUENCE: 50
acggagattg cttaaggagt cgttt                                           25

<210> SEQ ID NO 51
<211> LENGTH: 6455
<212> TYPE: DNA
<213> ORGANISM: Artificial Sequence
<220> FEATURE:
<223> OTHER INFORMATION: pACYCA_SXT

<400> SEQUENCE: 51
gcactgatga gggtgtcagt gaagtgcttc atgtggcagg agaaaaaagg ctgcaccggt      60
gcgtcagcag aatatgtgat acaggatata ttccgcttcc tcgctcactg actcgctacg     120
ctcggtcgtt cgactgcggc gagcggaaat ggcttacgaa cggggcggag atttcctgga     180
agatgccagg aagatactta acagggaagt gagagggccg cggcaaagcc gttttttccat    240 aggctccgcc cccctgacaa gcatcacgaa atctgacgct caaatcagtg gtggcgaaac     300
ccgacaggac tataaagata ccaggcgttt ccccctggcgg ctccctcgtg cgctctcctg    360
ttcctgcgaa aggacaagtt tggtgactg cgctcctcca agccagttac ctcggttcaa      420
agagttggta gctcagagaa ccttcgaaaa accgccctgc aaggcggttt tttcgttttc     480
agagcaagag attacgcgca gaccaaaacg atctcaagaa gatcatctta ttaatcagat     540
aaaatatttc tagatttcag tgcaatttat ctcttcaaat gtagcacctg aagtcagccc     600
catacgatat aagttgtaat tctcatgtta gtcatgcccc gcgcccaccg gaaggagctg     660
actgggttga aggctctcaa ggcatcggt cgagatcccg gtgcctaatg agtgagctaa      720
cttacattaa ttgcgttgcg ctcactgccc gctttccagt cgggaaacct gtcgtgccag     780
ctgcattaat gaatcggcca acgcgcgggg agaggcggtt tgcgtattgg gcgccagggt     840
ggtttttctt ttcaccagtg agacgggcaa cagctgattg cccttcaccg cctggccctg     900
agagagttgc agcaagcggt ccacgctggt ttgccccagc aggcgaaaat cctgtttgat     960
ggtggttaac ggcgggatat aacatgagct gtcttcggta tcgtcgtatc ccactaccga    1020
```

-continued

```
gatgtccgca ccaacgcgca gcccggactc ggtaatggcg cgcattgcgc ccagcgccat    1080
ctgatcgttg gcaaccagca tcgcagtggg aacgatgccc tcattcagca tttgcatggt    1140
ttgttgaaaa ccggacatgg cactccagtc gccttcccgt tccgctatcg gctgaatttg    1200
attgcgagtg agatatttat gccagccagc cagacgcaga cgcgccgaga cagaacttaa    1260
tgggcccgct aacagcgcga tttgctggtg acccaatgcg accagatgct ccacgcccag    1320
tcgcgtaccg tcttcatggg agaaaataat actgttgatg ggtgtctggt cagagacatc    1380
aagaaataac gccggaacat tagtgcaggc agcttccaca gcaatggcat cctggtcatc    1440
cagcggatag ttaatgatca gcccactgac gcgttgcgcg agaagattgt gcaccgccgc    1500
tttacaggct tcgacgccgc ttcgttctac catcgacacc accacgctgg cacccagttg    1560
atcggcgcga gatttaatcg ccgcgacaat ttgcgacggc gcgtgcaggg ccagactgga    1620
ggtggcaacg ccaatcagca acgactgttt gcccgccagt tgttgtgcca cgcggttggg    1680
aatgtaattc agctccgcca tcgccgcttc cacttttttcc cgcgttttcg cagaaacgtg    1740
gctggcctgg ttcaccacgc gggaaacggt ctgataagag acaccggcat actctgcgac    1800
atcgtataac gttactggtt tcacattcac caccctgaat tgactctctt ccgggcgcta    1860
tcatgccata ccgcgaaagg ttttgcgcca ttcgatggtg tccgggatct cgacgctctc    1920
ccttttgaca attaatcatc ggctcgtata tgggaattg tgagcggata acaattaagg    1980
agatatgcat ggatattaat actgaaactg agatcaagca aaagcattca ctaacccccct    2040 ttcctgtttt cctaatcagc ccggcatttc gcgggcgata ttttcacagc tatttcagga    2100
gttcagccat gaacgcttat tacattcagg atcgtcttga ggctcagagc tgggcgcgtc    2160
actaccagca gctcgcccgt gaagagaaag aggcagaact ggcagacgac atggaaaaag    2220
gcctgcccca gcacctgttt gaatcgctat gcatcgatca tttgcaacgc cacggggcca    2280
gcaaaaaatc cattacccgt gcgtttgatg acgatgttga gtttcaggag cgcatggcag    2340
aacacatccg gtacatggtt gaaaccattg ctcaccacca ggttgatatt gattcagagg    2400
tataaaacga atggaaaaac caaagctaat tcaacgcttt gctgagcgct ttagtgtcga    2460
tccaaacaag ttgttcgata ccctaaaagc aacagcattc aagcaacgtg acggtagtgc    2520
accgaccaat gagcagatga tggcgctctt ggtggttgca gatcagtacg gcttgaaccc    2580
tttcaccaaa gagattttg cgttccctga taaacaagct gggattattc cagtggtagg    2640
tgtcgatgga tggtctcgca tcattaatca acacgaccag tttgatggca tggagtttaa    2700
gacttcagaa acaaagtct ccctggatgg cgcgaaagaa tgcccggaat ggatggaatg    2760
catcatctat cggcgcgacc gttcgcaccc agtcaaaatc actgaatacc tggatgaagt    2820
ctatcgaccg cctttttgaag gtaacggcaa aaatggccct taccgggtag atggtccatg    2880
gcagacgcac actaagcgaa tgctaagaca taaatccatg atccagtgtt cccgcattgc    2940
gtttggcttt gtgggaattt tcgatcaaga cgaagcggag cgaattatcg aaggccaagc    3000
aacacacgtt gttgagccat cggtgattcc acccgagcaa gttgatgatc gaacccgagg    3060
gcttgtttac aagcttatcg agcgggcgga agcttcaaac gcttggaata gtgcattgga    3120
atatgccaat gaacatttc aaggtgttga actgacgttt gcgaaacaag aaataattaa    3180
tgcacagcaa caagcagcca aagcgctcac acagcctta gcttcttagc gccacgcatt    3240
cattttacta accctggcgg gattattctc ccgtcagggg gaaggtctcg tcttttatt    3300 ggagatcttc catgactaaa tcagcctcac ttttcgctt ggtattggtt gttgcccttg    3360
tcttaggttc gattcaagcc ggtaaagcgg caattgattc ggttcaagca agtgttgttc    3420
```

```
agcaccaaac agcgttagca caagctgcaa agtaaccact taaccctgaa ggggagttct   3480
ctccttcagg ggagtctccc ttcaaaggag gcaatatgaa ggttatcgac ctatcacaac   3540
gtactcctgc atggcaccag tggcgcattg caggggttac ggcatctgaa gccccaatta   3600
ttatggggcg ttcaccctac aaaacacctt ggcgattatg ggcagaaaaa accggattcg   3660
tattaccgga agacctatcg aataatccaa atgtgcttcg aggtatacgg ttggagcctc   3720
aagcaaggcg agcatttgag aatgcgcata atgactttct tctgccgtta tgtgcagaag   3780
ccgatcataa cgcaatcttt cgagccagct tgatggcat caacgatgcg ggcgaacctg    3840
ttgaactgaa atgtccttgc cagtcagttt ttgaggatgt gcaagctcac cgagaacaaa   3900
gtgaggcgta ccagttgtat tgggtgcaag tacagcacca aatactggtc gccaatagca   3960
cgcgtggttg gttggtattc tattttgagg atcaactgat tgagtttgaa atacaacgag   4020
acgcggcgtt cttaactgag ttgcaagaaa cagcgcttca gttttgggag ttagtacaga   4080
ccaaaaaaga accgtcaaaa tgccctgagc aagattgttt tgttcccaag ggtgaagccc   4140
aataccgttg gacatcgcta tcacggcagt attgctcagc acatgccgaa gtggtccgac   4200
tggaaaacca cattaaatct ttgaaagagg aaatgcgaga agctcagtcg aaattggtcg   4260
ctatgatggg taactacgct catgccgact atgctggggt caaactcagc cgctacatga   4320
tggcaggtac ggtggactat aagcaattgg ccaccgataa gttaggcgag ctggatgaac   4380
aggttttagc tgcttaccga aaagcgccac aagagcggtt gcgcattagc accaataagc   4440
cagagcagcc cgttgaaaca ccaatcaaaa tcagccttga gcaagagaac ttggttctgc   4500
caggtgactc gccgagctca ttttactttt aacgcatcct cacgataata tccgggtagg   4560
cgcaatcact ttcgtctact ccgttacaaa gcgaggctgg gtatttcccg gcctttctgt   4620
tatccgaaat ccactgaaag cacagcggct ggctgaggag ataaataata aacgaggggc   4680
tgtatgcaca aagcatcttc tgttgagtta agaacgagta tcgagatggc acatagcctt   4740
gctcaaattg gaatcaggtt tgtgccaata ccagtagaaa cagacgaaga atcctttccg   4800
cggccgccca ccgctgagca ataactagca taacccttg gggcctctaa acgggtcttg    4860
aggggttttt tgctgaaacc tcaggcattt gagaagcaca cggtcacact gcttccggta   4920
gtcaataaac cggtaaacca gcaatagaca taagcggcta tttaacgacc ctgccctgaa   4980
ccgacgacgg tctgacgctc agtggaacga aaactcacgt taagggattt tggtcatgag   5040
attatcaaaa aggatcttca cctagatcct tttaaattaa aaatgaagtt ttaaatcaat   5100
ctaaagtata tatgagtaaa cttggtctga cagttaccaa tgcttaatca gtgaggcacc   5160
tatctcagcg atctgtctat ttcgttcatc catagttgcc tgactcccg tcgtgtagat    5220
aactacgata cgggagggct taccatctgg ccccagtgct gcaatgatac cgcgagaccc   5280
acgctcaccg gctccagatt tatcagcaat aaaccagcca gccggaaggg ccgagcgcag   5340
aagtggtcct gcaactttat ccgcctccat ccagtctatt aattgttgcc gggaagctag   5400
agtaagtagt tcgccagtta atagtttgcg caacgttgtt gccattgcta caggcatcgt   5460
ggtgtcacgc tcgtcgtttg gtatggcttc attcagctcc ggttcccaac gatcaaggcg   5520
agttacatga tcccccatgt tgtgcaaaaa agcggttagc tccttcggtc ctccgatcgt   5580
tgtcagaagt aagttggccg cagtgttatc actcatggtt atggcagcac tgcataattc   5640
tcttactgtc atgccatccg taagatgctt ttctgtgact ggtgagtact caaccaagtc   5700
attctgagaa tagtgtatgc ggcgaccgag ttgctcttgc ccggcgtcaa tacgggataa   5760
```

| | |
|---|---|
| taccgcgcca catagcagaa ctttaaaagt gctcatcatt ggaaaacgtt cttcggggcg | 5820 |
| aaaactctca aggatcttac cgctgttgag atccagttcg atgtaaccca ctcgtgcacc | 5880 |
| caactgatct tcagcatctt ttactttcac cagcgtttct gggtgagcaa aaacaggaag | 5940 |
| gcaaaatgcc gcaaaaaagg gaataagggc gacacggaaa tgttgaatac tcatactctt | 6000 |
| ccttttcaa tattattgaa gcatttatca gggttattgt ctcatgagcg gatacatatt | 6060 |
| tgaatgtatt tagaaaaata aacaaatagg ggttccgcgc acatttcccc gaaaagtgcc | 6120 |
| acctgcatta tggtgaaagt tggaacctct tacgtgccga tcaacgtctc attttcgcca | 6180 |
| aaagttggcc cagggcttcc cggtatcaac agggacacca ggatttattt attctgcgaa | 6240 |
| gtgatcttcc gtcacaggta tttattcggc gcaaagtgcg tcgggtgatg ctgccaactt | 6300 |
| actgatttag tgtatgatgg tgtttttgag gtgctccagt ggcttctgtt tctatcagct | 6360 |
| gtccctcctg ttcagctact gacggggtgg tgcgtaacgg caaaagcacc gccggacatc | 6420 |
| agcgctagcg gagtgtatac tggcttacta tgttg | 6455 |

<210> SEQ ID NO 52
<211> LENGTH: 3508
<212> TYPE: DNA
<213> ORGANISM: Artificial Sequence
<220> FEATURE:
<223> OTHER INFORMATION: pRSF_FLP

<400> SEQUENCE: 52

| | |
|---|---|
| cactcgcatc aaccaaaccg ttattcattc gtgattgcgc ctgagcgaga cgaaatacgc | 60 |
| ggtcgctgtt aaaaggacaa ttacaaacag gaatcgaatg caaccggcgc aggaacactg | 120 |
| ccagcgcatc aacaatattt tcacctgaat caggatattc ttctaatacc tggaatgctg | 180 |
| ttttcccggg gatcgcagtg gtgagtaacc atgcatcatc aggagtacgg ataaaatgct | 240 |
| tgatggtcgg aagaggcata aattccgtca gccagtttag tctgaccatc tcatctgtaa | 300 |
| catcattggc aacgctacct ttgccatgtt tcagaaacaa ctctggcgca tcgggcttcc | 360 |
| catacaatcg atagattgtc gcacctgatt gcccgacatt atcgcgagcc catttatacc | 420 |
| catataaatc agcatccatg ttggaattta atcgcggcct agagcaagac gtttcccgtt | 480 |
| gaatatggct catactcttc cttttcaat attattgaag catttatcag ggttattgtc | 540 |
| tcatgagcgg atacatattt gaatgtattt agaaaaataa acaaataggc atgcagcgct | 600 |
| cttccgcttc ctcgctcact gactcgctac gctcggtcgt tcgactgcgg cgagcggtgt | 660 |
| cagctcactc aaaagcggta atacggttat ccacagaatc aggggataaa gccggaaaga | 720 |
| acatgtgagc aaaaagcaaa gcaccggaag aagccaacgc cgcaggcgtt tttccatagg | 780 |
| ctccgccccc ctgacgagca tcacaaaaat cgacgctcaa gccagaggtg gcgaaacccg | 840 |
| acaggactat aaagatacca ggcgtttccc cctggaagct ccctcgtgcg ctctcctgtt | 900 |
| ccgaccctgc cgcttaccgg atacctgtcc gcctttctcc cttcgggaag cgtggcgctt | 960 |
| tctcatagct cacgctgttg gtatctcagt tcggtgtagg tcgttcgctc caagctgggc | 1020 |
| tgtgtgcacg aaccccccgt tcagcccgac cgctgcgcct tatccggtaa ctatcgtctt | 1080 |
| gagtccaacc cggtaagaca cgacttatcg ccactggcag cagccattgg taactgattt | 1140 |
| agaggacttt gtcttgaagt tatgcacctg ttaaggctaa actgaaagaa cagattttgg | 1200 |
| tgagtgcggt cctccaaccc acttaccttg gttcaaagag ttggtagctc agcgaacctt | 1260 |
| gagaaaacca ccgttggtag cggtggtttt tctttattta tgagatgatg aatcaatcgg | 1320 |
| tctatcaagt caacgaacag ctattccgtt actctagatt tcagtgcaat ttatctcttc | 1380 |

```
aaatgtagca cctgaagtca gccccatacg atataagttg taattctcat gttagtcatg    1440
ccccgcgccc accggaagga gctgactggg ttgaaggctc tcaagggcat cggtcgagat    1500
cccggtgcct aatgagtgag ctaacttaca ttaattgcgt tgcgcgagct cttgacggct    1560
agctcagtcc taggtacagt gctagcatct cgcaaatcga aggagcctca tatgccacaa    1620
tttggtatat tatgtaaaac accacctaag gtgcttgttc gtcagtttgt ggaaaggttt    1680
gaaagacctt caggtgagaa aatagcatta tgtgctgctg aactaaccta tttatgttgg    1740
atgattacac ataacggaac agcaatcaag agagccacat tcatgagcta taatactatc    1800
ataagcaatt cgctgagttt cgatattgtc aataaatcac tccagtttaa atacaagacg    1860
caaaaagcaa caattctgga agcctcatta agaaattga ttcctgcttg ggaatttaca    1920
attattcctt actatggaca aaacatcaa tctgatatca ctgatattgt aagtagtttg    1980
caattacagt tcgaatcatc ggaagaagca gataagggaa atagccacag taaaaaaatg    2040
cttaaagcac ttctaagtga gggtgaaagc atctgggaga tcactgagaa aatactaaat    2100
tcgtttgagt atacttcgag atttacaaaa acaaaaactt tataccaatt cctcttccta    2160
gctactttca tcaattgtgg aagattcagc gatattaaga acgttgatcc gaaatcattt    2220
aaattagtcc aaaataagta tctgggagta ataatccagt gtttagtgac agagacaaag    2280
acaagcgtta gtaggcacat atacttcttt agcgcaaggg gtaggatcga tccacttgta    2340
tatttggatg aattttttgag gaattctgaa ccagtcctaa aacgagtaaa taggaccggc    2400
aattcttcaa gcaataaaca ggaataccaa ttattaaaag ataacttagt cagatcgtac    2460
aataaagctt tgaagaaaaa tgcgccttat tcaatctttg ctataaaaaa tggcccaaaa    2520
tctcacattg gaagacattt gatgacctca tttcttcaa tgaagggcct aacggagttg    2580
actaatgttg tgggaaattg gagcgataag cgtgcttctg ccgtggccag gacaacgtat    2640
actcatcaga taacagcaat acctgatcac tacttcgcac tagtttctcg gtactatgca    2700
tatgatccaa tatcaaagga aatgatagca ttgaaggatg agactaatcc aattgaggag    2760
tggcagcata tagaacagct aaagggtagt gctgaaggaa gcatacgata ccccgcatgg    2820
aatgggataa tatcacagga ggtactagac tacctttcat cctacataaa tagacgcata    2880
taagcggccg cccaccgctg agcaataact agcataaccc cttggggcct ctaaacgggt    2940
cttgaggggt ttttgctga aacctcaggc atttgagaag cacacggtca cactgcttcc    3000
ggtagtcaat aaaccggtaa accagcaata gacataagcg gctatttaac gaccctgccc    3060
tgaaccgacg acaagctgac gaccgggtct ccgcaagtgg cacttttcgg ggaaatgtgc    3120
gcggaacccc tatttgttta tttttctaaa tacattcaaa tatgtatccg ctcatgaatt    3180
aattcttaga aaaactcatc gagcatcaaa tgaaactgca atttattcat atcaggatta    3240
tcaataccat attttttgaaa aagccgtttc tgtaatgaag gagaaaactc accgaggcag    3300
ttccatagga tggcaagatc ctggtatcgg tctgcgattc cgactcgtcc aacatcaata    3360
caacctatta atttcccctc gtcaaaaata aggttatcaa gtgagaaatc accatgagtg    3420
acgactgaat ccggtgagaa tggcaaaagt ttatgcattt ctttccagac ttgttcaaca    3480
ggccagccat tacgctcgtc atcaaaat                                        3508
```

<210> SEQ ID NO 53
<211> LENGTH: 8798
<212> TYPE: DNA
<213> ORGANISM: Artificial Sequence
<220> FEATURE:

<223> OTHER INFORMATION: pACYC_idi_ispA_crtEBI

<400> SEQUENCE: 53

```
tatagtgagt cgtattaatt tcctaatgca ggagtcgcat aagggagagc gtcgagatcc      60
cggacaccat cgaatggcgc aaaacctttc gcggtatggc atgatagcgc ccggaagaga     120
gtcaattcag ggtggtgaat gtgaaaccag taacgttata cgatgtcgca gagtatgccg     180
gtgtctctta tcagaccgtt tcccgcgtgg tgaaccaggc cagccacgtt tctgcgaaaa     240
cgcgggaaaa agtggaagcg gcgatggcgg agctgaatta cattcccaac cgcgtggcac     300
aacaactggc gggcaaacag tcgttgctga ttggcgttgc cacctccagt ctggccctgc     360
acgcgccgtc gcaaattgtc gcggcgatta atctcgcgc cgatcaactg ggtgccagcg     420
tggtggtgtc gatggtagaa cgaagcggcg tcgaagcctg taaagcggcg gtgcacaatc     480
ttctcgcgca acgcgtcagt gggctgatca ttaactatcc gctggatgac caggatgcca     540
ttgctgtgga agctgcctgc actaatgttc cggcgttatt tcttgatgtc tctgaccaga     600
cacccatcaa cagtattatt ttctcccatg aagacggtac gcgactgggc gtggagcatc     660
tggtcgcatt gggtcaccag caaatcgcgc tgttagcggg cccattaagt tctgtctcgg     720
cgcgtctgcg tctggctggc tggcataaat atctcactcg caatcaaatt cagccgatag     780
cggaacggga aggcgactgg agtgccatgt ccggtttca acaaaccatg caaatgctga     840
atgagggcat cgttcccact gcgatgctgg ttgccaacga tcagatgcgc tgggcgcaa     900
tgcgcgccat taccgagtcc gggctgcgcg ttggtgcgga catctcggta gtgggatacg     960
acgataccga agacagctca tgttatatcc gccgttaac caccatcaaa caggattttc    1020
gcctgctggg gcaaaccagc gtggaccgct tgctgcaact ctctcagggc caggcggtga    1080
agggcaatca gctgttgccc gtctcactgg tgaaaagaaa aaccaccctg gcgcccaata    1140
cgcaaaccgc ctctccccgc gcgttggccg attcattaat gcagctggca cgacaggttt    1200
cccgactgga aagcgggcag tgagcgcaac gcaattaatg taagttagct cactcattag    1260
gcaccgggat ctcgaccgat gcccttgaga gccttcaacc cagtcagctc cttccggtgg    1320
gcgcggggca tgactaacat gagaattaca acttatatcg tatggggctg acttcaggtg    1380
ctacatttga agagataaat tgcactgaaa tctagagcgg ttcagtagaa aagatcaaag    1440
gatcttcttg agatcctttt tttctgcgcg taatcttttg ccctgtaaac gaaaaaacca    1500
cctgggagg tggtttgatc gaaggttaag tcagttgggg aactgcttaa ccgtggtaac    1560
tggctttcgc agagcacagc aaccaaatct gtccttccag tgtagccgga ctttggcgca    1620
cacttcaaga gcaaccgcgt gtttagctaa acaaatcctc tgcgaactcc cagttaccaa    1680
tggctgctgc cagtggcgtt ttaccgtgct tttccgggtt ggactcaagt gaacagttac    1740
cggataaggc gcagcagtcg ggctgaacgg ggagttcttg cttacagccc agcttggagc    1800
gaacgaccta caccgagccg agataccagt gtgtgagcta tgagaaagcg ccacacttcc    1860
cgtaagggag aaaggcggaa caggtatccg gtaaacggca gggtcggaac aggagagcgc    1920
aagagggagc gacccgccgg aaacggtggg gatctttaag tcctgtcggg tttcgcccgt    1980
actgtcagat tcatggttga gcctcacggc tcccacagat gcaccggaaa agcgtctgtt    2040
tatgtgaact ctggcaggag gcggagcct atggaaaaac gccaccggcg cggccctgct    2100
gttttgcctc acatgttagt cccctgctta tccacggaat ctgtgggtaa ctttgtatgt    2160
gtccgcagcg cccgccgcag tctcacgccc ggagcgtagc gaccgagtga gctagctatt    2220
tgtttatttt tctaaataca ttcaaatatg tatccgctca tgagacaata accctgataa    2280
```

```
atgcttcaat aatattgaaa aaggaagagt atgagggaag cggtgatcgc cgaagtatcg    2340
actcaactat cagaggtagt tggcgtcatc gagcgccatc tcgaaccgac gttgctggcc    2400
gtacatttgt acggctccgc agtggatggc ggcctgaagc cacacagtga tattgatttg    2460
ctggttacgg tgaccgtaag gcttgatgaa caacgcggc gagctttgat caacgacctt    2520
ttggaaactt cggcttcccc tggagagagc gagattctcc gcgctgtaga agtcaccatt    2580
gttgtgcacg acgacatcat tccgtggcgt tatccagcta agcgcgaact gcaatttgga    2640
gaatggcagc gcaatgacat tcttgcaggt atcttcgagc cagccacgat cgacattgat    2700
ctggctatct tgctgacaaa agcaagagaa catagcgttg ccttggtagg tccagcggcg    2760
gaggaactct ttgatccggt tcctgaacag gatctatttg aggcgctaaa tgaaaccta    2820 acgctatgga actcgccgcc cgactgggct ggcgatgagc gaaatgtagt gcttacgttg    2880
tcccgcattt ggtacagcgc agtaaccggc aaaatcgcgc cgaaggatgt cgctgccgac    2940
tgggcaatgg agcgcctgcc ggcccagtat cagcccgtca tacttgaagc tagacaggct    3000
tatcttggac aagaagaaga tcgcttggcc tcgcgcgcag atcagttgga agaatttgtc    3060
cactacgtga aaggcgagat caccaaggta gtcggcaaat aatgtctaac aattcgttca    3120
agccgagggg ccgcaagatc cggccacgat gacccggtcg tcggttcagg gcagggtcgt    3180
taaatagccg cttatgtcta ttgctggttt accggtttat tgactaccgg aagcagtgtg    3240
accgtgtgct tctcaaatgc ctgaggtttc agcaaaaaac ccctcaagac ccgtttagag    3300
gccccaaggg gttatgctag ttattgctca gcggtggcag cagccaggt taattaagct    3360 gcgctagtag acgagtccat gtgctggcgt tcaaatttcg cagcagcggt ttctttacca    3420
gactcgaggg taccgacgtc agcgatcgcg tggccggccg atatccaatt gagatctttg    3480
acggctagct cagtcctagg tacagtgcta gccatcaaca aataaggagg agctacaatg    3540
cagaccgaac atgtgattct gctgaacgcg cagggcgtgc cgaccggcac cctggaaaaa    3600
tatgcggcgc ataccgcgga tacccgcctg catctggcgt ttagcagctg gctgtttaac    3660
gcgaaaggcc agctgctggt gacccgccgc gcgctgagca aaaaagcgtg gccgggcgtg    3720
tggaccaaca gcgtgtgcgg ccatccgcag ctgggcgaaa gcaacgaaga tgcggtgatt    3780
cgccgctgcc gctatgaact gggcgtggaa attacccccgc cggaaagcat ttatccggat    3840
tttcgctatc gcgcgaccga tccgagcggc attgtgaaa acgaagtgtg cccggtgttt    3900
gcggcgcgca ccaccagcgc gctgcagatt aacgatgatg aagtgatgga ttatcagtgg    3960
tgcgatctgg cggatgtgct gcatggcatt gatgcgaccc cgtgggcgtt tagcccgtgg    4020
atggtgatgc aggcgaccaa ccgcgaagcg cgcaaacgcc tgagcgcgtt tacccagctg    4080
aaataaaaaa accccgacat tgccggggt tgtgagcgcc gcaaacccg cttcggcggg    4140 gtttcgccgc agatctttga cggctagctc agtcctaggt acagtgctag ccacgaccat    4200
ataaggagga tagaagatgg atttcccgca gcagctggaa gcgtgtgtga acaggcgaa    4260 ccaggcgctg agccgcttta ttgcgccgct gccgtttcag aacaccccgg tggtggaaac    4320
catgcagtat ggcgcgctgc tgggcggcaa acgcctgcgc ccgtttctgg tgtatgcgac    4380
cggccacatg tttggcgtga gcaccaacac cctggatgcg ccggcggcgg cggtggaatg    4440
cattcatgcg tatagcctga ttcatgatga tctgccggcg atggatgatg atgatctgcg    4500
ccgcggcctg ccgacctgcc atgtgaaatt tggcgaagcg aacgcgattc tggcgggcga    4560
tgcgctgcag accctggcgt ttagcattct gagcgatgcg gatatgccgg aagtgagcga    4620
```

-continued

```
tcgcgatcgc attagcatga ttagcgaact ggcgagcgcg agcggcattg cgggcatgtg   4680
cggcggccag gcgctggatc tggatgcgga aggcaaacat gtgccgctgg atgcgctgga   4740
acgcattcat cgccataaaa ccggcgcgct gattcgcgcg gcggtgcgcc tgggcgcgct   4800
gagcgcgggc gataaaggcc gccgcgcgct gccggtgctg gataaatatg cggaaagcat   4860
tggcctggcg tttcaggtgc aggatgatat tctggatgtg gtgggcgata ccgcgaccct   4920
gggcaaacgc cagggcgcgg atcagcagct gggcaaaagc acctatccgg cgctgctggg   4980
cctggaacag gcgcgcaaaa agcgcgcgca tctgattgat gatgcgcgcc agagcctgaa   5040
acagctggcg gaacagagcc tggataccag cgcgctggaa gcgctggcgg attatattat   5100
tcagcgcaac aaataataaa caataagtat taataggccc ctgatcgccg caaacccccgc  5160
ttcggcgggg tttcgccgca agcttttgac ggctagctca gtcctaggta cagtgctagc   5220
taacaaaaca aaaggaggta atagaatggt atctggctca aaggctggcg tctcgccaca   5280
tcgcgaaatt gaagtgatgc gccagagcat tgatgatcat ctggcgggcc tgctgccgga   5340
aaccgatagc caggatattg tgagcctggc gatgcgcgaa ggcgtgatgg cgccgggcaa   5400
acgcattcgc ccgctgctga tgctgctggc ggcgcgcgat ctgcgctatc agggcagtat   5460
gccgacccctg ctggatctgg cgtgcgcggt ggaactgacc cataccgcga gcctgatgct   5520
ggatgatatg ccgtgcatgg ataacgcgga actgcgccgc ggccagccga ccacccataa   5580
aaaatttggc gaaagcgtgg cgattctggc gagcgtgggc ctgctgagca agcgtttgg    5640
cctgattgcg gcgaccggcg atctgccggg cgaacgccgc gcgcaggcgg tgaacgaact   5700
gagcaccgcg gtgggcgtgc agggcctggt gctgggccag tttcgcgatc tgaacgatgc   5760
ggcgctggat cgcacccccgg atgcgattct gagcaccaac catctgaaaa ccggcattct   5820
gtttagcgcg atgctgcaga ttgtggcgat tgcgagcgcg agcagcccga gcacccgcga   5880
aaccctgcac gcgtttgcgc tggattttgg ccaggcgttt cagctgctgg atgatctgcg   5940
cgatgatcat ccggaaaccg gcaaagatcg caacaaagat gcgggcaaaa gcaccctggt   6000
gaaccgcctg ggcgcggatg cggcgcgcca gaaactgcgc gaacatattg atagcgcgga   6060
taaacatctg accttttgcgt gcccgcaggg cggcgcgatt cgccagttta tgcatctgtg   6120
gtttggccat catctggcgg attggagccc ggtgatgaaa attgcgtaat accgcccttt   6180
tgggttcaag cagtacataa cctaatatcc taaaggagcg aaaactatgt cccaaccccc   6240
cttgctagac cacgcaaccc agacgatggc gaacggcagc aagagctttg cgaccgcggc   6300
gaaactgttt gatccggcga cccgccgcag cgtgctgatg ctgtatacct ggtgccgcca   6360
ttgcgatgat gtgattgatg atcagacgca tggctttgcg agcgaagcgg cggcggaaga   6420
agaagcgacc cagcgcctgg cgcgcctgcg caccctgacc ctggcggcgt ttgaaggcgc   6480
ggaaatgcag gacccggcgt ttgcggcgtt tcaggaagtg gcgctgaccc acggcattac   6540
cccgcgcatg gcgctggatc atctggatgg cttttgcgatg gatgtggcgc agacccgcta   6600
tgtgaccttt gaagatacccc tgcgctattg ctatcatgtg gcgggcgtgg tgggcctgat   6660
gatggcgcgc gtgatgggcg tgcgcgatga acgcgtgctg gatcgcgcgt gcgatctggg   6720
cctggcgttt cagctgacca acattgcgcg cgatattatt gatgatgcgg cgattgatcg   6780
ctgctatctg ccggcggaat ggctgcagga tgcgggcctg accccggaaa actatgcggc   6840
gcgcgaaaac cgcgcggcgc tggcgcgcgt ggcggaacgc ctgattgatg cggcggaacc   6900
gtattatatt agcagccagg cgggcctgca tgatctgccg ccgcgctgcg cgtgggcgat   6960
tgcgaccgcg cgcagcgtgt atcgcgaaat tggcattaaa gtgaaagcgg cgggcggcag   7020
```

```
cgcgtgggat cgccgccagc ataccagcaa aggcgaaaaa attgcgatgc tgatggcggc    7080
gccgggccag gtgattcgcg cgaaaaccac ccgcgtgacc ccgcgcccgg cgggcctgtg    7140
gcagcgcccg gtgtaagcgg gcggccatga cgttcacgca ggatcgatag agtcaacaag    7200
gagttattat catgaaaaaa acggttgtga tcggcgctgg gttcggcggc ctggcgctgg    7260
cgattcgcct gcaggcggcg ggcattccga ccgtgctgct ggaacagcgc gataaaccgg    7320
gcggccgcgc gtatgtgtgg catgatcagg gctttacctt tgatgcgggc ccgaccgtga    7380
ttaccgatcc gaccgcgctg gaagcgctgt ttaccctggc gggccgccgc atggaagatt    7440
atgtgcgcct gctgccggtg aaaccgtttt atcgcctgtg ctgggaaagc ggcaaaaccc    7500
tggattatgc gaacgatagc gcggaactgg aagcgcagat tacccagttt aacccgcgcg    7560
atgtggaagg ctatcgccgc tttctggcgt atagccaggg ggtgtttcag gaaggctatc    7620
tgcgcctggg cagcgtgccg tttctgagct tcgcgatat gctgcgcgcg ggcccgcagc    7680
tgctgaaact gcaggcgtgg cagagcgtgt atcagagcgt gagccgcttt attgaagatg    7740
aacatctgcg ccaggcgttt agctttcata gcctgctggt gggcggcaac ccgtttacca    7800
ccagcagcat ttatacccct gattcatgcgc tggaacgcga atgggcgtg tggtttccgg    7860 aaggcggcac cggcgcgctg gtgaacggca tggtgaaact gtttaccgat ctgggcggcg    7920
aaattgaact gaacgcgcgc gtggaagaac tggtggtggc ggataaccgc gtgagccagg    7980
tgcgcctggc ggatggccgc atttttgata ccgatgcggt ggcgagcaac gcggatgtgg    8040
tgaacaccta taaaaactg ctgggccatc atccggtggg ccagaaacgc gcggcggcgc    8100
tggaacgcaa aagcatgagc aacagcctgt tgtgctgta ttttggcctg aaccagccgc    8160
atagccagct ggcgcatcat accatttgct ttggcccgcg ctatcgcgaa ctgattgatg    8220 aaattttac cggcagcgcg ctggcggatg attttagcct gtatctgcat agcccgtgcg    8280
tgaccgatcc gagcctggcg ccgcggggct gcgcagctt ttatgtgctg gcgcggtgc    8340 cgcatctggg caacgcgccg ctggattggg cgcaggaagg cccgaaactg cgcgatcgca    8400
tttttgatta tctggaagaa cgctatatgc cgggcctgcg cagccagctg gtgacccagc    8460
gcatttttac cccggcggat tttcatgata ccctggatgc gcatctgggc agcgcgttta    8520
gcattgaacc gctgctgacc cagagcgcgt ggtttcgccc gcataaccgc gatagcgata    8580
ttgcgaacct gtatctggtg ggcgcgggca cccatccggg cgcgggcatt ccgggcgtgg    8640
tggcgagcgc gaaagcgacc gcgagcctga tgatcgaaga cctgcagtaa cgccgcaaac    8700
cccgcttcgg cggggtttcg ccgcccatgg tatatctcct tattaaagtt aaacaaaatt    8760
atttctacag gggaattgtt atccgctcac aattcccc                           8798
```

<210> SEQ ID NO 54  
<211> LENGTH: 10842  
<212> TYPE: DNA  
<213> ORGANISM: Artificial Sequence  
<220> FEATURE:  
<223> OTHER INFORMATION: pACYC_idi_ispA_crtEBI_dxs

<400> SEQUENCE: 54

```
ggggaattgt gagcggataa caattcccct gtagaaataa ttttgtttaa ctttaataag     60
gagatatacc atgggcgcca ttcgatggtg tccgggatct cgacgctctc ccttatgcga    120
ctcctgcatt aggaaattaa tacgactcac tatagggga ttgtgagcgg ataacaattc    180
ccctgtagaa ataattttgt ttaactttaa taaggagata taccattgag atctttgacg    240
```

```
gctagctcag tcctaggtac agtgctagcc atcaacaaat aaggaggagc tacaatgcag    300
accgaacatg tgattctgct gaacgcgcag ggcgtgccga ccggcaccct ggaaaaatat    360
gcggcgcata ccgcggatac ccgcctgcat ctggcgttta gcagctggct gtttaacgcg    420
aaaggccagc tgctggtgac ccgccgcgcg ctgagcaaaa aagcgtggcc gggcgtgtgg    480
accaacagcg tgtgcggcca tccgcagctg ggcgaaagca cgaagatgc ggtgattcgc     540 cgctgccgct atgaactggg cgtggaaatt accccgccgg aaagcattta tccgatttt    600 cgctatcgcg cgaccgatcc gagcggcatt gtggaaaacg aagtgtgccc ggtgtttgcg    660
gcgcgcacca ccagcgcgct gcagattaac gatgatgaag tgatggatta tcagtggtgc    720
gatctggcgg atgtgctgca tggcattgat gcgaccccgt gggcgtttag cccgtggatg    780
gtgatgcagg cgaccaaccg cgaagcgcgc aaacgcctga gcgcgtttac ccagctgaaa    840
taaaaaaacc ccgacatttg ccggggttgt gagcgccgca aaccccgctt cggcggggtt    900
tcgccgcaga tctttgacgg ctagctcagt cctaggtaca gtgctagcca cgaccatata    960
aggaggatag aagatggatt tcccgcagca gctggaagcg tgtgtgaaac aggcgaacca   1020
ggcgctgagc cgctttattg cgccgctgcc gtttcagaac accccggtgg tggaaaccat   1080
gcagtatggc gcgctgctgg gcggcaaacg cctgcgcccg tttctggtgt atgcgaccgg   1140
ccacatgttt ggcgtgagca ccaacaccct ggatgcgccg cggcggcgg tggaatgcat    1200 tcatgcgtat agcctgattc atgatgatct gccggcgatg gatgatgatg atctgcgccg   1260
cggcctgccg acctgccatg tgaaatttgg cgaagcgaac gcgattctgg cgggcgatgc   1320
gctgcagacc ctggcgttta gcattctgag cgatgcggat atgccggaag tgagcgatcg   1380
cgatcgcatt agcatgatta gcgaactggc gagcgcgagc ggcattgcgg gcatgtgcgg   1440
cggccaggcg ctggatctgg atgcggaagg caaacatgtg ccgctggatg cgctggaacg   1500
cattcatcgc cataaaaccg gcgcgctgat tcgcgcggcg gtgcgcctgg gcgcgctgag   1560
cgcgggcgat aaaggccgcc gcgcgctgcc ggtgctggaa aaatatgcgg aaagcattgg   1620
cctggcgttt caggtgcagg atgatattct ggatgtggtg ggcgataccg cgaccctggg   1680
caaacgccag ggcgcggatc agcagctggg caaaagcacc tatccggcgc tgctgggcct   1740
ggaacaggcg cgcaaaaaag cgcgcgatct gattgatgat gcgcgccaga gcctgaaaca   1800
gctggcggaa cagagcctgg ataccagcgc gctggaagcg ctggcggatt atattattca   1860
gcgcaacaaa taataaacaa taagtattaa taggcccctg atcgccgcaa accccgcttc   1920
ggcggggttt cgccgcaagc ttttgacggc tagctcagtc ctaggtacag tgctagctaa   1980
caaaacaaaa ggaggtaata gaatggtatc tggctcaaag gctggcgtct cgccacatcg   2040
cgaaattgaa gtgatgcgcc agagcattga tgatcatctg gcgggcctgc tgccggaaac   2100
cgatagccag gatattgtga gcctggcgat gcgcgaaggc gtgatggcgc cgggcaaacg   2160
cattcgcccg ctgctgatgc tgctggcggc gcgcgatctg cgctatcagg cagtatgcc    2220 gaccctgctg gatctggcgt gcgcggtgga actgacccat accgcgagcc tgatgctgga   2280
tgatatgccg tgcatggata acgcggaact gcgccgcggc cagccgacca cccataaaaa   2340
atttggcgaa agcgtggcga ttctggcgag cgtgggcctg ctgagcaaag cgtttggcct   2400
gattgcggcg accggcgatc tgccgggcga acgccgcgcg caggcggtga cgaactgag    2460 caccgcggtg ggcgtgcagg gcctggtgct gggccagttt cgcgatctga acgatgcggc   2520
gctggatcgc accccggatg cgattctgag caccaaccat ctgaaaaccg gcattctgtt   2580
tagcgcgatg ctgcagattg tggcgattgc gagcgcgagc agcccgagca cccgcgaaac   2640
```

```
cctgcacgcg tttgcgctgg attttggcca ggcgtttcag ctgctggatg atctgcgcga  2700
tgatcatccg gaaaccggca aagatcgcaa caaagatgcg ggcaaaagca ccctggtgaa  2760
ccgcctgggc gcggatgcgg cgcgccagaa actgcgcgaa catattgata gcgcggataa  2820
acatctgacc tttgcgtgcc cgcagggcgg cgcgattcgc cagtttatgc atctgtggtt  2880
tggccatcat ctggcggatt ggagcccggt gatgaaaatt gcgtaatacc gcccttttgg  2940
gttcaagcag tacataacct aatatcctaa aggagcgaaa actatgtccc aaccccccctt  3000
gctagaccac gcaacccaga cgatggcgaa cggcagcaag agctttgcga ccgcggcgaa  3060
actgtttgat ccggcgaccc gccgcagcgt gctgatgctg tatacctggt gccgccattg  3120
cgatgatgtg attgatgatc agacgcatgg ctttgcgagc gaagcggcgg cggaagaaga  3180
agcgacccag cgcctggcgc gcctgcgcac cctgaccctg gcggcgtttg aaggcgcgga  3240
aatgcaggac ccggcgtttg cggcgtttca ggaagtggcg ctgacccacg gcattacccc  3300
gcgcatggcg ctggatcatc tggatggctt tgcgatggat gtggcgcaga cccgctatgt  3360
gacctttgaa gataccctgc gctattgcta tcatgtggcg ggcgtggtgg gcctgatgat  3420
ggcgcgcgtg atgggcgtgc gcgatgaacg cgtgctggat cgcgcgtgcg atctgggcct  3480
ggcgtttcag ctgaccaaca ttgcgcgcga tattattgat gatgcggcga ttgatcgctg  3540
ctatctgccg gcgaatggc tgcaggatgc gggcctgacc ccggaaaact atgcggcgcg  3600
cgaaaaccgc gcggcgctgg cgcgcgtggc ggaacgcctg attgatgcgg cggaaccgta  3660
ttatattagc agccaggcgg gcctgcatga tctgccgccg cgctgcgcgt gggcgattgc  3720
gaccgcgcgc agcgtgtatc gcgaaattgg cattaaagtg aaagcggcgg gcggcagcgc  3780
gtgggatcgc cgccagcata ccagcaaagg cgaaaaaatt gcgatgctga tggcggcgcc  3840
gggccaggtg attcgcgcga aaaccaccg cgtgaccccg cgcccggcgg gcctgtggca  3900
gcgcccggtg taagcgggcg gccatgacgt tcacgcagga tcgatagagt caacaaggag  3960
ttattatcat gaaaaaaacg gttgtgatcg gcgctgggtt cggcggcctg gcgctggcga  4020
ttcgcctgca ggcggcgggc attccgaccg tgctgctgga acagcgcgat aaaccgggcg  4080
gccgcgcgta tgtgtggcat gatcagggct ttacctttga tgcgggcccg accgtgatta  4140
ccgatccgac cgcgctggaa gcgctgtttt ccctggcggg ccgccgcatg aagattatg   4200
tgcgcctgct gccggtgaaa ccgttttatc gcctgtgctg ggaaagcggc aaaaccctgg  4260
attatgcgaa cgatagcgcg gaactggaag cgcagattac ccagtttaac ccgcgcgatg  4320
tggaaggcta tcgccgcttt ctggcgtata gccaggcggt gtttcaggaa ggctatctgc  4380
gcctgggcag cgtgccgttt ctgagctttc gcgatatgct gcgcgcgggc ccgcagctgc  4440
tgaaactgca ggcgtggcag agcgtgtatc agagcgtgag ccgctttatt gaagatgaac  4500
atctgcgcca ggcgtttagc tttcatagcc tgctggtggg cggcaacccg tttaccacca  4560
gcagcattta accctgatt catgcgctgg aacgcgaatg gggcgtgtgg tttccggaag  4620
gcggcaccgg cgcgctggtg aacggcatgg tgaaactgtt taccgatctg gcggcgaaa   4680
ttgaactgaa cgcgcgcgtg gaagaactgg tggtggcgga taaccgcgtg agccaggtgc  4740
gcctggcgga tggccgcatt tttgataccg atgcggtggc gagcaacgcg gatgtggtga  4800
acacctataa aaaactgctg ggccatcatc cggtgggcca gaaacgcgcg cggcgctgg   4860
aacgcaaaag catgagcaac agcctgtttg tgctgtattt tggcctgaac cagccgcata  4920
gccagctggc gcatcatacc atttgctttg gcccgcgcta tcgcgaactg attgatgaaa  4980
```

```
tttttaccgg cagcgcgctg gcggatgatt ttagcctgta tctgcatagc ccgtgcgtga    5040
ccgatccgag cctggcgccg ccgggctgcg cgagctttta tgtgctggcg ccggtgccgc    5100
atctgggcaa cgcgccgctg gattgggcgc aggaaggccc gaaactgcgc gatcgcattt    5160
ttgattatct ggaagaacgc tatatgccgg gcctgcgcag ccagctggtg acccagcgca    5220
tttttacccc ggcggatttt catgataccc tggatgcgca tctgggcagc gcgtttagca    5280
ttgaaccgct gctgacccag agcgcgtggt ttcgcccgca taaccgcgat agcgatattg    5340
cgaacctgta tctggtgggc gcgggcaccc atccgggcgc gggcattccg ggcgtggtgg    5400
cgagcgcgaa agcgaccgcg agcctgatga tcgaagacct gcagtaacgc cgcaaacccc    5460
gcttcggcgg ggtttcgccg cccatgaatt ggatatcggc cggccacgcg atcgctgacg    5520
tcggtacctt gacggctagc tcagtcctag gtacagtgct agccgtctcc acataaggag    5580
cagttcacat gagttttgat attgccaaat acccgaccct ggcactggtc gactccaccc    5640
aggagttacg actgttgccg aaagagagtt taccgaaact ctgcgacgaa ctgcgccgct    5700
atttactcga cagcgtgagc cgttccgcg ggcacttcgc ctccgggctg gcacggtcg     5760
aactgaccgt ggcgctgcac tatgtctaca cacccgtt tgaccaattg atttgggatg     5820
tggggcatca ggcttatccg cataaaattt tgaccggacg ccgcgacaaa tcggcacca    5880
tccgtcagaa aggcggtctg cacccgttcc cgtggcgcgg cgaaagcgaa tatgacgtat    5940
taagcgtcgg gcattcatca acctccatca gtgccggaat tggtattgcg gttgctgccg    6000
aaaaagaagg caaaaatcgc cgcaccgtct gtgtcattgg cgatggcgcg attaccgcag    6060
gcatggcgtt tgaagcgatg aatcacgcgg gcgatatccg tcctgatatg ctggtgattc    6120
tcaacgacaa tgaaatgtcg atttccgaaa atgtcggcgc gctcaacaac catctggcac    6180
agctgctttc cggtaagctt tactcttcac tgcgcgaagg cgggaaaaaa gttttctctg    6240
gcgtgccgcc aattaaagag ctgctcaaac gcaccgaaga acatattaaa ggcatggtag    6300
tgcctggcac gttgtttgaa gagctgggct ttaactacat cggcccggtg gacggtcacg    6360
atgtgctggg gcttatcacc acgctaaaga acatgcgcga cctgaaaggc ccgcagttcc    6420
tgcatatcat gaccaaaaaa ggtcgtggtt atgaaccggc agaaaaagac ccgatcactt    6480
tccacgccgt gcctaaattt gatccctcca gcggttgttt gccgaaaagt agcggcggtt    6540
tgccgagcta ttcaaaaatc tttggcgact ggttgtgcga acggcagcg aaagacaaca    6600
agctgatggc gattactccg gcgatgcgtg aaggttccgg catggtcgag ttttcacgta    6660
aattcccgga tcgctacttc gacgtggcaa ttgccgagca cacgcggtg acctttgctg    6720
cgggtctggc gattggtggg tacaaaccca ttgtcgcgat ttactccact ttcctgcaac    6780
gcgcctatga tcaggtgctg catgacgtgg cgattcaaaa gcttccggtc ctgttcgcca    6840
tcgaccgcgc gggcattgtt ggtgctgacg gtcaaaccca tcagggtgct tttgatctct    6900
cttacctgcg ctgcataccg gaaatggtca ttatgacccc gagcgatgaa acgaatgtc    6960
gccagatgct ctataccggc tatcactata acgatggccc gtcagcggtg cgctacccgc    7020
gtggcaacgc ggtcggcgtg gaactgacgc cgctggaaaa actaccaatt ggcaaaggca    7080
ttgtgaagcg tcgtggcgag aaactggcga tccttaactt tggtacgctg atgccagaag    7140
cggcgaaagt cgccgaatcg ctgaacgcca cgctggtcga tatgcgtttt gtgaaaccgc    7200
ttgatgaagc gttaattctg gaaatggccg ccagccatga agcgctggtc accgtagaag    7260
aaaacgccat tatgggcggc gcaggcagcg gcgtgaacga agtgctgatg gcccatcgta    7320
aaccagtacc cgtgctgaac attggcctgc cggacttctt tattccgcaa ggaactcagg    7380
```

```
aagaaatgcg cgccgaactc ggcctcgatg ccgctggtat ggaagccaaa atcaaggcct   7440
ggctggcata acgccgcaaa ccccgcttcg gcggggtttc gccgcttaat taacctaggc   7500
tgctgccacc gctgagcaat aactagcata accccttggg gcctctaaac gggtcttgag   7560
gggttttttg ctgaaacctc aggcatttga gaagcacacg gtcacactgc ttccggtagt   7620
caataaaccg gtaaaccagc aatagacata agcggctatt taacgaccct gccctgaacc   7680
gacgaccggg tcatcgtggc cggatcttgc ggcccctcgg cttgaacgaa ttgttagaca   7740
ttatttgccg actaccttgg tgatctcgcc tttcacgtag tggacaaatt cttccaactg   7800
atctgcgcgc gaggccaagc gatcttcttc ttgtccaaga taagcctgtc tagcttcaag   7860
tatgacgggc tgatactggg ccggcaggcg ctccattgcc cagtcggcag cgacatcctt   7920
cggcgcgatt ttgccggtta ctgcgctgta ccaaatgcgg gacaacgtaa gcactacatt   7980
tcgctcatcg ccagcccagt cgggcggcga gttccatagc gttaaggttt catttagcgc   8040
ctcaaataga tcctgttcag gaaccggatc aaagagttcc tccgccgctg gacctaccaa   8100
ggcaacgcta tgttctcttg cttttgtcag caagatagcc agatcaatgt cgatcgtggc   8160
tggctcgaag atacctgcaa gaatgtcatt gcgctgccat tctccaaatt gcagttcgcg   8220
cttagctgga taacgccacg gaatgatgtc gtcgtgcaca acaatggtga cttctacagc   8280
gcggagaatc tcgctctctc caggggaagc cgaagtttcc aaaaggtcgt tgatcaaagc   8340
tcgccgcgtt gtttcatcaa gccttacggt caccgtaacc agcaaatcaa tatcactgtg   8400
tggcttcagg ccgccatcca ctgcggagcc gtacaaatgt acggccagca acgtcggttc   8460
gagatggcgc tcgatgacgc caactacctc tgatagttga gtcgatactt cggcgatcac   8520
cgcttccctc atactcttcc tttttcaata ttattgaagc atttatcagg gttattgtct   8580
catgagcgga tacatatttg aatgtattta gaaaaataaa caaatagcta gctcactcgg   8640
tcgctacgct ccgggcgtga gactgcggcg ggcgctgcgg acacatacaa agttacccac   8700
agattccgtg gataagcagg ggactaacat gtgaggcaaa acagcagggc cgcgccggtg   8760 gcgttttttcc ataggctccg ccctcctgcc agagttcaca taaacagacg cttttccggt   8820
gcatctgtgg gagccgtgag gctcaaccat gaatctgaca gtacgggcga aacccgacag   8880
gacttaaaga tccccaccgt ttccggcggg tcgctccctc ttgcgctctc ctgttccgac   8940
cctgccgttt accggatacc tgttccgcct ttctccctta cgggaagtgt ggcgctttct   9000
catagctcac acactggtat ctcggctcgg tgtaggtcgt tcgctccaag ctgggctgta   9060
agcaagaact cccgttcag cccgactgct gcgccttatc cggtaactgt tcacttgagt   9120
ccaacccgga aaagcacggt aaaacgccac tggcagcagc cattggtaac tgggagttcg   9180
cagaggattt gtttagctaa acacgcggtt gctcttgaag tgtgcgccaa agtccggcta   9240
cactggaagg acagatttgg ttgctgtgct ctgcgaaagc cagttaccac ggttaagcag   9300
ttccccaact gacttaacct tcgatcaaac cacctcccca ggtggttttt tcgtttacag   9360
ggcaaaagat tacgcgcaga aaaaaggat ctcaagaaga tcctttgatc ttttctactg   9420
aaccgctcta gatttcagtg caatttatct cttcaaatgt agcacctgaa gtcagcccca   9480
tacgatataa gttgtaattc tcatgttagt catgccccgc gcccaccgga aggagctgac   9540
tgggttgaag gctctcaagg gcatcggtcg agatcccggt gcctaatgag tgagctaact   9600
tacattaatt gcgttgcgct cactgcccgc tttccagtcg ggaaacctgt cgtgccagct   9660
gcattaatga atcggccaac gcgcggggag aggcggtttg cgtattgggc gccagggtgg   9720
```

| | | |
|---|---|---|
| tttttctttt caccagtgag acgggcaaca gctgattgcc cttcaccgcc tggccctgag | 9780 | |
| agagttgcag caagcggtcc acgctggttt gccccagcag gcgaaaatcc tgtttgatgg | 9840 | |
| tggttaacgg cgggatataa catgagctgt cttcggtatc gtcgtatccc actaccgaga | 9900 | |
| tgtccgcacc aacgcgcagc ccggactcgg taatggcgcg cattgcgccc agcgccatct | 9960 | |
| gatcgttggc aaccagcatc gcagtgggaa cgatgccctc attcagcatt tgcatggttt | 10020 | |
| gttgaaaacc ggacatggca ctccagtcgc ctttcccgttc cgctatcggc tgaatttgat | 10080 | |
| tgcgagtgag atatttatgc cagccagcca gacgcagacg cgccgagaca gaacttaatg | 10140 | |
| ggcccgctaa cagcgcgatt tgctggtgac ccaatgcgac cagatgctcc acgcccagtc | 10200 | |
| gcgtaccgtc ttcatgggag aaaataatac tgttgatggg tgtctggtca gagacatcaa | 10260 | |
| gaaataacgc cggaacatta gtgcaggcag cttccacagc aatggcatcc tggtcatcca | 10320 | |
| gcggatagtt aatgatcagc ccactgacgc gttgcgcgag aagattgtgc accgccgctt | 10380 | |
| tacaggcttc gacgccgctt cgttctacca tcgacaccac cacgctggca cccagttgat | 10440 | |
| cggcgcgaga tttaatcgcc gcgacaattt gcgacgcgcg gtgcagggcc agactggagg | 10500 | |
| tggcaacgcc aatcagcaac gactgtttgc ccgccagttg ttgtgccacg cggttgggaa | 10560 | |
| tgtaattcag ctccgccatc gccgcttcca ctttttcccg cgttttcgca gaaacgtggc | 10620 | |
| tggcctggtt caccacgcgg gaaacggtct gataagagac accggcatac tctgcgacat | 10680 | |
| cgtataacgt tactggtttc acattccacca ccctgaattg actctcttcc gggcgctatc | 10740 | |
| atgccatacc gcgaaaggtt ttgcgccatt cgatggtgtc cgggatctcg acgctctccc | 10800 | |
| ttatgcgact cctgcattag gaaattaata cgactcacta ta | 10842 | |

<210> SEQ ID NO 55
<211> LENGTH: 6875
<212> TYPE: DNA
<213> ORGANISM: Artificial Sequence
<220> FEATURE:
<223> OTHER INFORMATION: pACYC_BudACB

<400> SEQUENCE: 55

| | | |
|---|---|---|
| tgcacgaacc ccccgttcag tccgaccgct gcgccttatc cggtaactat cgtcttgagt | 60 | |
| ccaacccgga agacatgca aaagcaccac tggcagcagc cactggtaat tgatttagag | 120 | |
| gagttagtct tgaagtcatg cgccggttaa ggctaaactg aaaggacaag ttttggtgac | 180 | |
| tgcgctcctc caagccagtt acctcggttc aaagagttgg tagctcagag aaccttcgaa | 240 | |
| aaaccgccct gcaaggcggt ttttcgtttt tcagagcaag agattacgcg cagaccaaaa | 300 | |
| cgatctcaag aagatcatct tattaatcag ataaaatatt tctagatttc agtgcaattt | 360 | |
| atctcttcaa atgtagcacc tgaagtcagc cccatacgat ataagttgta attctcatgt | 420 | |
| tagtcatgcc ccgcgcccac cggaaggagc tgactgggtt gaaggctctc aagggcatcg | 480 | |
| gtcgagatcc cggtgcctaa tgagtgagct aacttacatt aattgcgttg cgctcactgc | 540 | |
| ccgctttcca gtcgggaaac ctgtcgtgcc agctgcatta atgaatcggc caacgcgcgg | 600 | |
| ggagaggcgg tttgcgtatt gggcgccagg gtggtttttc ttttcaccag tgagacgggc | 660 | |
| aacagctgat tgcccttcac cgcctggccc tgagagagtt gcagcaagcg gtccacgctg | 720 | |
| gtttgcccca gcaggcgaaa atcctgtttg atggtggtta acggcgggat ataacatgag | 780 | |
| ctgtcttcgg tatcgtcgta tcccactacc gagatgtccg caccaacgcg cagcccggac | 840 | |
| tcggtaatgg cgcgcattgc gcccagcgcc atctgatcgt tggcaaccag catcgcagtg | 900 | |
| ggaacgatgc cctcattcag catttgcatg gtttgttgaa aaccggacat ggcactccag | 960 | |

```
tcgccttccc gttccgctat cggctgaatt tgattgcgag tgagatattt atgccagcca    1020
gccagacgca gacgcgccga gacagaactt aatgggcccg ctaacagcgc gatttgctgg    1080
tgacccaatg cgaccagatg ctccacgccc agtcgcgtac cgtcttcatg ggagaaaata    1140
atactgttga tgggtgtctg gtcagagaca tcaagaaata cgccggaac attagtgcag     1200 gcagcttcca cagcaatggc atcctggtca tccagcggat agttaatgat cagcccactg    1260
acgcgttgcg cgagaagatt gtgcaccgcc gctttacagg cttcgacgcc gcttcgttct    1320
accatcgaca ccaccacgct ggcacccagt tgatcggcgc gagatttaat cgccgcgaca    1380
atttgcgacg cgcgtgcag ggccagactg gaggtggcaa cgccaatcag caacgactgt     1440
ttgcccgcca gttgttgtgc cacgcggttg ggaatgtaat tcagctccgc catcgccgct    1500 tccactttt cccgcgtttt cgcagaaacg tggctggcct ggttcaccac gcgggaaacg     1560
gtctgataag agacaccggc atactctgcg acatcgtata acgttactgg tttcacattc    1620
accaccctga attgactctc ttccgggcgc tatcatgcca taccgcgaaa ggttttgcgc    1680
cattcgatgg tgtccgggat ctcgacgctc tcccttacta gtttgacaat taatcatcgg    1740
ctcgtataat gtgtggaatt gtgagcggat aacaattaag gaggttccga tgaatcatgc    1800
ttcagattgc acctgtgaag agagtctgtg tgaaacgcta cgcgcgtttt ccgctcagca    1860
tcccgatagc gtgctgtatc aaacttcgct gatgagcgcc ctgctcagcg cgtctacga    1920 aggtaccacc accattgcgg acctgctgaa gcacggtgat ttcgggctcg gcacttttaa    1980
tgaactcgac ggcgagctga tcgcgtttag cagccaggtt tatcaactgc gtgccgacgg    2040
cagcgcgcgt aaagcgcgtc cggaacagaa aacgccgttt gcggtgatga cctggtttca    2100
gccgcagtac cgtaaaaacct ttgaccatcc ggtcagccgc cagcagctgc atgaggttat    2160
tgaccagcaa attccttccg acaatctgtt ctgcgcgctg cgaatcgatg gtcatttccg    2220
ccacgcccat acccgcaccg tgcctcgtca gacgccgccc taccgggcga tgaccgacgt    2280
gctcgacgat cagccggttt tccgctttaa ccagcgtgac ggcgtactgg tcggttttcg    2340
taccccgcag catatgcagg gaattaacgt cgccggctat cacgaacact tcattaccga    2400
tgaccgccag ggcggcggcc acctgctgga ctaccagctc gaccatgggg tattgacctt    2460
cggcgaaatt cataagctga tgatcgacct tcccgccgac agcgcgttcc tgcaggccaa    2520
tttgcatccc gataatctcg atgccgccat ccgttcagta gaaagttagg aggttcacat    2580
ggacaaacag tatccgcagc gccagtgggc gcacggcgcc gatctggtcg tcagccaact    2640
ggaagcgcaa ggcgtacggc aggtcttcgg gatccccggc gctaaaatcg ataaggtttt    2700
cgactcgttg ctggactcct caatccgcat tattccggta cgtcacgagg ccaacgccgc    2760
ctttatggcc gccgcggtcg ggcgcattac cggcaaagcg ggcgtcgcgc tggtgacctc    2820
cggacccggt tgttccaacc tgataaccgg gatggccacc gccaatagcg aaggcgaccc    2880
ggtggtggcc ctgggcggcg cggtcaaacg cgcggataaa gccaaacagg tacaccagag    2940
tatggacacg gtggcgatgt tcagcccggt caccaaatac gcggtagaag tgacctcgcc    3000
ggatgcgctg gcggaagtgg tttctaacgc ttttcgcgcc gccgagcagg tcgcccggg    3060 cagcgccttc gtcagtctgc cgcaggatgt ggtcgatggt ccggtgaccg gcaaagtcct    3120 gccccgccagc agcgcgccgc agatgggcgc cgcgcctgac gaggcaatca atcaggttgc    3180
gaagttgatt gccaggcga agaatccggt gttcctgctt ggattaatgg ccagccagac    3240
ggaaaacagc gccgcgctgc atcgtttgct ggaaaccagc catattccgg tcaccagcac    3300
```

```
ctatcaggcc gccggggcgg tcaatcagga taacttctcg cgcttcgccg ggcgcgtcgg      3360
gctgtttaac aatcaggccg gtgaccgctt attgcaactg gccgacctgg ttatctgcat      3420
cggctatagc ccggtggaat acgaaccggc gatgtggaac agcggcaacg cgacgctggt      3480
acatatcgac gtactgcccg cctatgaaga gcgtaactac acgccggatg tcgagctggt      3540
gggcgacatc gccggcacgc tgaacaagct ggcgcaaaat atcgatcatc ggctggtgct      3600
ctcgccgcag gctgctgaaa tcctccacga ccgccagcat cagcgggaac tgcttgaccg      3660
ccgcggagcg cagttgaatc agtttgccct gcacccgctg cgtatcgttc gcgccatgca      3720
ggatatcgtc aacagcgacg tcacgctgac ggtcgatatg gggagcttcc atatctggat      3780
cgcccgctat ctctacagct ccgcgcccg tcaggtgatg atctccaacg gtcagcagac      3840
catgggcgtc gccctgccgt gggccatcgg ggcctggctg gtcaatccgc agcgcaaagt      3900
ggtctcggtc tccggcgatg gcggttttct gcaatccagc atggagctgg aaacggcggt      3960
ccgcctgaaa gccaacatcc tgcatcttat ctgggtcgat aacggctaca acatggtcgc      4020
catccaggaa gagaaaaaat atcaacgcct gtccggcgtc gagttcggtc ctatggattt      4080
taaagcctat gccgaatcct tcggcgcgaa agggtttgcg gtggaaagcg ctgaggcgct      4140
ggagccgacg ctacgcgcgg cgatggacgt cgacggcccg gcggtggtcg ccatccccgt      4200
ggattaccgt gataacccgc tgctgatggg ccagctacac ctgagtcaaa ttctttaagt      4260
catcacaaaa ggaaatggaa atgaaaaaag tcgcacttgt caccggcgcc ggtcagggca      4320
ttggtaaagc tatcgcgtta cgcctcgtga aggacggttt tgccgtggcg atcgccgatt      4380
acaatgacgt cacagcgaaa gccgtggcgg atgaaatcaa ccagcacggc ggcccgggcaa     4440 tcgcggtcaa agtcgatgtt tccgaccgtg agcaggtgtt tgccgccgtc gaacaggcgc      4500
gaaaaacgct gggcggattc aacgtcatcg tcaataacgc cggggtcgcg ccatcaacgc      4560
ctatcgaatc cattacgccg gagattgtcg acaaggtcta caacatcaac gttaaagggg      4620
tgatctgggg gattcaggcg gcagtcgagg cctttaaaaa agaggggcac ggcggcaaaa      4680
tcatcaacgc ctgttcgcag gccggacacg tcggcaaccc ggaactggcg gtctacagct      4740
cgagcaaatt cgccgtacgc ggtttaacgc aaaccgccgc tcgcgacctg cgccgctgg       4800 gtattaccgt taacggctac tgcccggggga ttgtgaaaac gccgatgtgg gccgagatcg      4860
atcgtcaggt atccgaagcg gcgggtaaac tctgggcta cggacagcc gaattcgcca        4920 aacgcatcac cctcggccgc ctgtctgagc cagaagatgt cgccgcctgc gtctcttatc      4980
tcgccagccc ggattccgat tatatgaccg gtcaatcgct gctgatcgat ggcgggatgg      5040
tattcaatta ttaacctag gctgctgcca ccgctgagca ataactagca taacccttg        5100 gggcctctaa acgggtcttg aggggttttt tgctgaaacc tcaggcattt gagaagcaca      5160
cggtcacact gcttccggta gtcaataaac cggtaaacca gcaatagaca taagcggcta      5220
tttaacgacc ctgccctgaa ccgacgaccg ggtcgaattt gctttcgaat ttctgccatt      5280
catccgctta ttatcactta ttcaggcgta gcaccaggcg tttaagggca ccaataactg      5340
ccttaaaaaa attacgcccc gccctgccac tcatcgcagt actgttgtaa ttcattaagc      5400
attctgccga catggaagcc atcacagacg gcatgatgaa cctgaatcgc cagcggcatc      5460
agcaccttgt cgccttgcgt ataatatttg cccatagtga aaacgggggc gaagaagttg      5520
tccatattgg ccacgtttaa atcaaaactg gtgaaactca cccagggatt ggctgagacg      5580
aaaaacatat tctcaataaa ccccttaggg aaataggcca ggttttcacc gtaacacgcc      5640
acatcttgcg aatatatgtg tagaaactgc cggaaatcgt cgtggtattc actccagagc      5700
```

```
gatgaaaacg tttcagtttg ctcatggaaa acggtgtaac aagggtgaac actatcccat    5760
atcaccagct caccgtcttt cattgccata cggaactccg gatgagcatt catcaggcgg    5820
gcaagaatgt gaataaaggc cggataaaac ttgtgcttat ttttctttac ggtctttaaa    5880
aaggccgtaa tatccagctg aacgtctgg ttataggtac attgagcaac tgactgaaat     5940
gcctcaaaat gttctttacg atgccattgg gatatatcaa cggtggtata tccagtgatt    6000 ttttctcca tttagcttc cttagctcct gaaaatctcg ataactcaaa aaatacgccc      6060
ggtagtgatc ttatttcatt atggtgaaag ttggaacctc ttacgtgccg atcaacgtct    6120 catttcgcc aaaagttggc ccagggcttc ccggtatcaa cagggacacc aggatttatt     6180
tattctgcga agtgatcttc cgtcacaggt atttattcgg cgcaaagtgc gtcgggtgat    6240
gctgccaact tactgattta gtgtatgatg gtgtttttga ggtgctccag tggcttctgt    6300
ttctatcagc tgtccctcct gttcagctac tgacggggtg gtgcgtaacg gcaaaagcac    6360
cgccggacat cagcgctagc ggagtgtata ctggcttact atgttggcac tgatgagggt    6420
gtcagtgaag tgcttcatgt ggcaggagaa aaaaggctgc accggtgcgt cagcagaata    6480
tgtgatacag gatatattcc gcttcctcgc tcactgactc gctacgctcg gtcgttcgac    6540
tgcggcgagc ggaaatggct tacgaacggg gcggagattt cctggaagat gccaggaaga    6600
tacttaacag ggaagtgaga gggccgcggc aaagccgttt ttccataggc tccgcccccc    6660
tgacaagcat cacgaaatct gacgctcaaa tcagtggtgg cgaaacccga caggactata    6720
aagataccag gcgtttcccc tggcggctcc ctcgtgcgct ctcctgttcc tgcctttcgg    6780
tttaccggtg tcattccgct gttatggccg cgtttgtctc attccacgcc tgacactcag    6840
ttccgggtag gcagttcgct ccaagctgga ctgta                              6875

<210> SEQ ID NO 56
<211> LENGTH: 29
<212> TYPE: DNA
<213> ORGANISM: Artificial Sequence
<220> FEATURE:
<223> OTHER INFORMATION: Promoter_gamma

<400> SEQUENCE: 56
ttgacaatta atcatcggct cgtataatg                                       29

<210> SEQ ID NO 57
<211> LENGTH: 35
<212> TYPE: DNA
<213> ORGANISM: Artificial Sequence
<220> FEATURE:
<223> OTHER INFORMATION: Synthetic 5' UTR_gamma

<400> SEQUENCE: 57
ggaattgtga gcggataaca attaaggaga tatgc                                35

<210> SEQ ID NO 58
<211> LENGTH: 35
<212> TYPE: DNA
<213> ORGANISM: Artificial Sequence
<220> FEATURE:
<223> OTHER INFORMATION: Promoter_FLP

<400> SEQUENCE: 58
ttgacggcta gctcagtcct aggtacagtg ctagc                                35

<210> SEQ ID NO 59
```

```
<211> LENGTH: 25
<212> TYPE: DNA
<213> ORGANISM: Artificial Sequence
<220> FEATURE:
<223> OTHER INFORMATION: Synthetic 5' UTR_FLP

<400> SEQUENCE: 59
atctcgcaaa tcgaaggagc ctcat                                            25

<210> SEQ ID NO 60
<211> LENGTH: 35
<212> TYPE: DNA
<213> ORGANISM: Artificial Sequence
<220> FEATURE:
<223> OTHER INFORMATION: Promoter_crtE

<400> SEQUENCE: 60
ttgacggcta gctcagtcct aggtacagtg ctagc                                 35

<210> SEQ ID NO 61
<211> LENGTH: 25
<212> TYPE: DNA
<213> ORGANISM: Artificial Sequence
<220> FEATURE:
<223> OTHER INFORMATION: Synthetic 5' UTR_crtE

<400> SEQUENCE: 61
cacgaccata taaggaggat agaag                                            25

<210> SEQ ID NO 62
<211> LENGTH: 35
<212> TYPE: DNA
<213> ORGANISM: Artificial Sequence
<220> FEATURE:
<223> OTHER INFORMATION: Promoter_idi

<400> SEQUENCE: 62
ttgacggcta gctcagtcct aggtacagtg ctagc                                 35

<210> SEQ ID NO 63
<211> LENGTH: 25
<212> TYPE: DNA
<213> ORGANISM: Artificial Sequence
<220> FEATURE:
<223> OTHER INFORMATION: Synthetic 5' UTR_idi

<400> SEQUENCE: 63
catcaacaaa taaggaggag ctaca                                            25

<210> SEQ ID NO 64
<211> LENGTH: 35
<212> TYPE: DNA
<213> ORGANISM: Artificial Sequence
<220> FEATURE:
<223> OTHER INFORMATION: Promoter_ispA

<400> SEQUENCE: 64
ttgacggcta gctcagtcct aggtacagtg ctagc                                 35

<210> SEQ ID NO 65
<211> LENGTH: 25
<212> TYPE: DNA
<213> ORGANISM: Artificial Sequence
<220> FEATURE:
<223> OTHER INFORMATION: Synthetic 5' UTR_ispA

<400> SEQUENCE: 65
```

```
cacgaccata taaggaggat agaag                                          25

<210> SEQ ID NO 66
<211> LENGTH: 35
<212> TYPE: DNA
<213> ORGANISM: Artificial Sequence
<220> FEATURE:
<223> OTHER INFORMATION: Promoter_dxs

<400> SEQUENCE: 66
ttgacggcta gctcagtcct aggtacagtg ctagc                               35

<210> SEQ ID NO 67
<211> LENGTH: 25
<212> TYPE: DNA
<213> ORGANISM: Artificial Sequence
<220> FEATURE:
<223> OTHER INFORMATION: Synthetic 5' UTR_dxs

<400> SEQUENCE: 67
cgtctccaca taaggagcag ttcac                                          25

<210> SEQ ID NO 68
<211> LENGTH: 29
<212> TYPE: DNA
<213> ORGANISM: Artificial Sequence
<220> FEATURE:
<223> OTHER INFORMATION: Promoter_BudA

<400> SEQUENCE: 68
ttgacaatta atcatcggct cgtataatg                                      29

<210> SEQ ID NO 69
<211> LENGTH: 38
<212> TYPE: DNA
<213> ORGANISM: Artificial Sequence
<220> FEATURE:
<223> OTHER INFORMATION: Synthetic 5' UTR_BudA

<400> SEQUENCE: 69
tgtggaattg tgagcggata acaattaagg aggttccg                            38
```

MICROORGANISM STRAIN FOR HIGH-PERFORMANCE METABOLISM OF BIOMASS-DERIVED CARBON SOURCE

CROSS-REFERENCE TO RELATED APPLICATIONS

This application is a United States National Phase entry of International Appl. No. PCT/KR2018/005437, filed May 11, 2018, which claims priority from Korean Patent Application No. 10-2018-0054287, filed on May 11, 2018, with the Korean Intellectual Property Office, the disclosure of both of which are incorporated herein in their entirety by reference.

TECHNICAL FIELD

The present disclosure relates to a novel microorganism capable of metabolizing various carbon sources at high rates.

BACKGROUND

Due to various environmental problems such as depletion of petroleum resources and generation of greenhouse gases, there is a need for a technology for sustainable and eco-friendly production of many compounds previously produced from petrochemical processes. Biomass has been modified over time to fossil fuels as basis of a conventional industry. In order to replace the fossil fuels, the biomass as a carbon source must be converted efficiently.

In order to convert the biomass to a target compound, sugar contained in the biomass must be converted into a desired metabolite through a fermentation process of a microorganism. Until now, glucose obtained from starch crops such as corn and sugar cane has been used in the fermentation process. However, in a near future, when a demand for bio compound is soaring, it is expected that many problems will be caused by soaring grain prices. For this reason, efforts have been made to replace the raw materials needed for bioprocessing with natural-rich land and marine plants.

In particular, among various biomass existing in nature, brown macroalgae (*Saccharina japonica*, etc.) is attracting attention as a next-generation raw material. Brown microalgae have a higher carbon dioxide fixation rate than conventional land plants and have a fast growth rate to secure a large amount of biomass. Further, the fermentation process is not inhibited because there is no lignin, and an expensive pre-treatment process is not necessary. However, carbon source rich in the brown microalgae is alginic acid (a homopolymer of α-L-guluronate and β-D-mannuronate). In this connection, industrial microbes do not contain alginic acid metabolic pathway and thus cannot carry out metabolism.

Therefore, it is necessary to secure microorganisms which are capable of metabolizing various carbon sources containing alginic acid at high rates. There is also a need for a technology that may convert the carbon source to high value compounds via appropriate genetic engineering improvements. Securing and developing the strains will greatly contribute to the sustainable production of various materials such as biofuels, platform compounds and pharmaceuticals from the various biomasses.

SUMMARY

The present inventors have completed the present disclosure by developing microorganisms that may quickly metabolize various carbon sources in order to produce compounds environmentally friendly that have been produced by conventional petrochemical processes.

The present disclosure has been made in an effort to provide a *Vibrio* sp. DHG strain having an accession number of KCTC13239BP with high capabilities to utilize various carbon sources.

The present disclosure has been made in an effort to provide a transformed *Vibrio* sp. DHG strain in which a gene encoding a gamma protein represented by a nucleotide sequence of SEQ ID NO: 6 is introduced into the DHG strain.

The present disclosure has been made in an effort to provide a transformed strain for lycopene production, in which a crtEBI gene represented by a nucleotide sequence of SEQ ID NO: 9 is introduced into the transformed DHG strain.

The present disclosure has been made in an effort to provide a transformed strain for producing 2,3-butanediol, in which one or more genes selected from the group consisting of a budA gene represented by a nucleotide sequence of SEQ ID NO: 13, a budB gene represented by a nucleotide sequence of SEQ ID NO: 14 and a budC gene represented by a nucleotide sequence of SEQ ID NO: 15 are introduced into the transformed DHG strain.

The present disclosure has been made in an effort to provide a method for producing lycopene, the method comprising culturing the transformed strain for lycopene production.

The present disclosure has been made in an effort to provide a method for producing 2,3-butanediol, the method comprising culturing the transformed strain for producing the 2,3-butanediol.

The present disclosure has been made in an effort to provide an SXT recombinant system expression cassette comprising a synthetic 5' UTR (untranslated region), a promoter and a target gene, a flippase gene expression cassette, a crtEBI gene expression cassette or a budACB operon expression cassette.

The present disclosure has been made in an effort to provide a recombinant vector comprising the SXT recombination system expression cassette, flippase gene expression cassette, crtEBI gene expression cassette or budACB operon expression cassette.

An exemplary embodiment of the present disclosure provides a *Vibrio* sp. DHG strain having an accession number of KCTC13239BP with a carbon source high-performance metabolic pathway.

Another exemplary embodiment of the present disclosure provides a transformed *Vibrio* sp. DHG strain in which a gene encoding a gamma protein represented by a nucleotide sequence of SEQ ID NO: 6 is introduced into the DHG strain.

Yet another exemplary embodiment of the present disclosure provides a transformed strain for lycopene production, in which a crtEBI gene represented by a nucleotide sequence of SEQ ID NO: 9 is introduced into the transformed DHG strain.

Yet another exemplary embodiment of the present disclosure provides a transformed strain for producing 2,3-butanediol, in which one or more genes selected from the group consisting of a budA gene represented by a nucleotide sequence of SEQ ID NO: 13, a budB gene represented by a nucleotide sequence of SEQ ID NO: 14 and a budC gene represented by a nucleotide sequence of SEQ ID NO: 15 are introduced into the transformed DHG strain.

Yet another exemplary embodiment of the present disclosure provides a method for producing lycopene, the method comprising culturing the transformed strain for lycopene production.

Yet another exemplary embodiment of the present disclosure provides a method for producing 2,3-butanediol, the method comprising culturing the transformed strain for producing the 2,3-butanediol.

Yet another exemplary embodiment of the present disclosure provides an SXT recombinant system expression cassette comprising a synthetic 5' UTR (untranslated region), a promoter represented by one or more nucleotide sequences selected from the group consisting of SEQ ID NOs: 22 to 35 and 56, and one or more genes selected from the group consisting of genes encoding beta, exo and gamma proteins.

Yet another exemplary embodiment of the present disclosure provides a recombinant vector comprising the SXT recombinant system expression cassette.

Yet another exemplary embodiment of the present disclosure provides a flippase gene expression cassette comprising a synthetic 5' UTR (untranslated region), a promoter represented by one or more nucleotide sequences selected from the group consisting of SEQ ID NOs: 22 to 35 and 58, and a gene coding flippase.

Yet another exemplary embodiment of the present disclosure provides a recombinant vector comprising the flippase gene expression cassette.

Yet another exemplary embodiment of the present disclosure provides a crtEBI gene expression cassette comprising a synthetic 5' UTR (untranslated region), a promoter represented by one or more nucleotide sequences selected from the group consisting of SEQ ID NOs: 22 to 35 and 60, and a crtEBI gene.

Yet another exemplary embodiment of the present disclosure provides a recombinant vector comprising the crtEBI gene expression cassette.

Yet another exemplary embodiment of the present disclosure provides a budACB operon expression cassette comprising a synthetic 5' UTR (untranslated region), a promoter represented by one or more nucleotide sequences selected from the group consisting of SEQ ID NOs: 22 to 35 and 68, and at least one gene selected from the group consisting of genes coding BudA, BudC and BudB proteins.

Yet another exemplary embodiment of the present disclosure provides a recombinant vector comprising the BudACB operon expression cassette.

According to the exemplary embodiments of the present disclosure, the *Vibrio* sp. DHG strain according to the present invention was observed to grow at a very high rate in a minimal medium/nutrient medium, etc., compared to microorganisms such as *Escherichia coli*, and shows resistance at a high initial sugar/salt concentrations as well as being able to produce lycopene and 2,3-butanediol through genetic manipulation. Therefore, the *Vibrio* sp. DHG strain can be used in various production fields of high value-added compounds using microorganisms.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
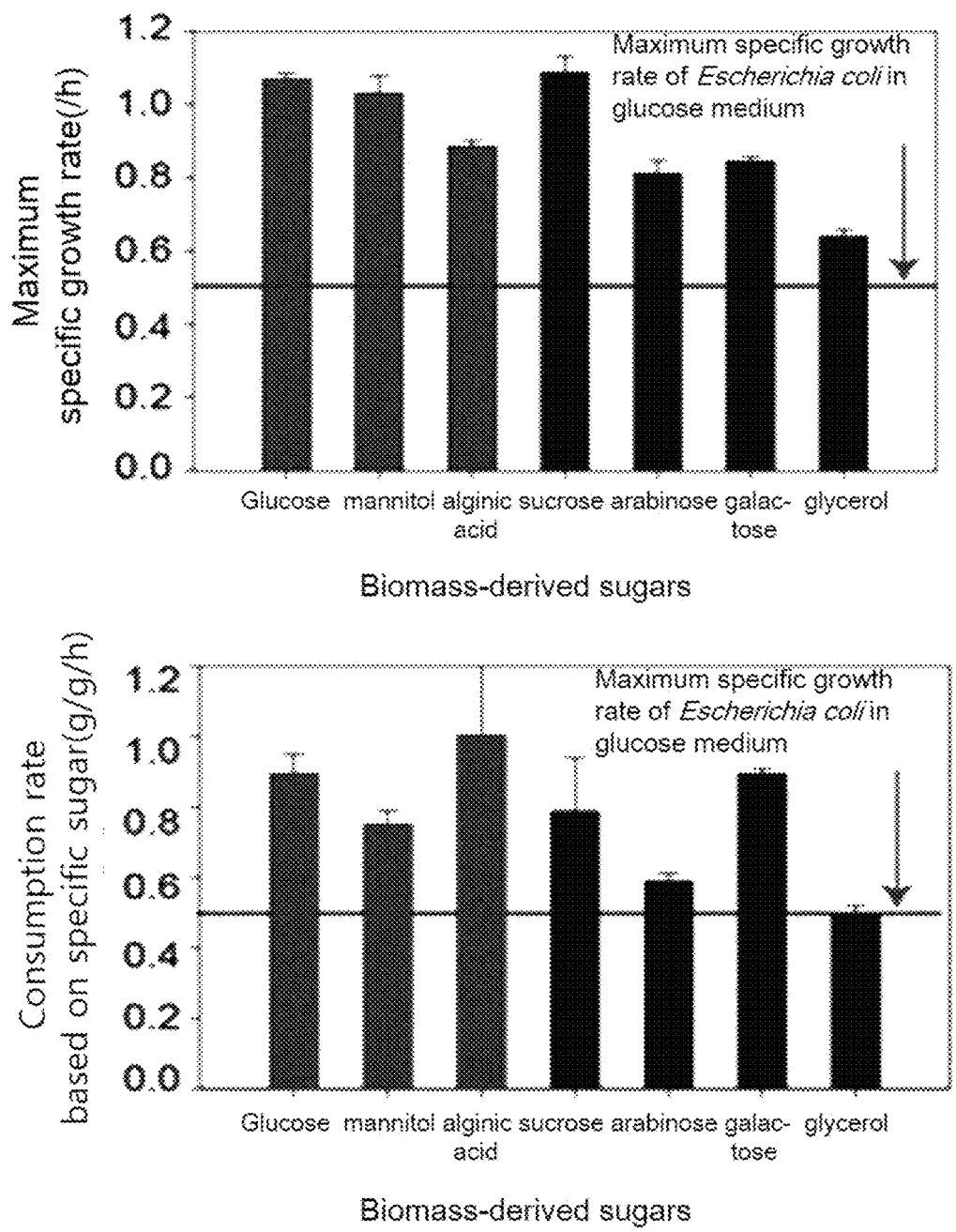
FIG. 1 shows a growth rate of a *Vibrio* sp. DHG strain based on a carbon source according to the present disclosure.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in detail.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

According to an aspect of the present disclosure, the present disclosure provides a *Vibrio* sp. DHG strain having an accession number of KCTC13239BP with a carbon source high-performance metabolic pathway.

As used herein, the term "carbon source" refers to a carbon compound that is assimilated by a living body and used as a bio-constituent carbon. In culturing strains, carbon sources are used to identify physiological relationships between nutrients and the strains such that isolation and growth characteristics of the strains are identified.

The carbon source may be sugar or sugar alcohol. More specifically, the carbon source may include one or more selected from the group consisting of glucose, mannitol, sucrose, arabinose, galactose, glycerol, xylose, mannose, fructose, lactose, maltose, sucrose, alginic acid, cellulose, dextrin, glycogen, hyaluronic acid, lentinan, Zymosan, chitosan, glucan, lignin, and pectin. Preferably, the carbon source may include one or more selected from the group consisting of glucose, mannitol, alginic acid, sucrose, arabinose, galactose and glycerol, but is not limited thereto.

As used herein, the term "carbon source high-performance metabolic pathway" refers to a metabolic pathway containing enzymes that may metabolize various sugars or sugar alcohols. Microorganisms having the carbon source high-performance metabolic pathway may use a mixed sugar containing one or more sugars or sugar alcohols as the carbon source.

In one embodiment of the present disclosure, the strain includes a 16S rDNA gene represented by a nucleotide sequence of a SEQ ID NO: 1.

As used herein, the term "gene" should be considered in the broadest sense, and may encode a structural or regulatory protein. In this connection, the regulatory protein includes a transcription factor, a heat shock protein or a protein involved in DNA/RNA replication, transcription and/or translation. In the present disclosure, a target gene that is subject to expression inhibition may be present as an extra-chromosomal component.

In another embodiment of the present disclosure, the strain comprises an SXT recombination system. More specifically, the strain may comprise a beta gene represented by a nucleotide sequence of SEQ ID NO: 3 or a beta protein represented by an amino acid sequence of SEQ ID NO: 2 and an exo gene represented by a nucleotide sequence of SEQ ID NO: 5 or an exo protein represented by an amino acid sequence of SEQ ID NO: 4. Further, the strain may comprise functional equivalents of the genes or proteins described above. The term "functional equivalent" means polynucleotides having at least 70%, preferably at least 80%, more preferably at least 90%, more preferably at least 95% sequence homology with the nucleotide sequence of the beta or exo gene via deletion, substitution or insertion of the nucleotide. The functional equivalent refers to a polynucleotide that exhibits substantially homogeneous physiological activity with the genes described above. The "% sequence homology" of the polynucleotide is identified by comparing a comparison region with two optimally arranged sequences. A portion of the polynucleotide sequence in the comparison region may include an addition or deletion (that is, gap) compared to a reference sequence (not including an additions or deletion) for the optimal alignment of the two sequences.

Further, the functional equivalents have at least 80% or more, preferably 90%, more preferably 95% or more sequence homology (i.e., identity) with the beta or exo proteins described above via the addition, substitution or deletion of amino acids. More preferably, the functional equivalents have, for example, 80%, 81%, 82%, 83%, 84%, 85%, 86%, 87%, 88%, 89%, 90%, 91%, 92%, 93%, 94%, 95%, 96%, 97%, 98%, 99%, 100% sequence homology with the beta or exo proteins via the addition, substitution or deletion of amino acids. The functional equivalents refer to a peptide that exhibits substantially the same physiological activity as the protein described above. As used herein, sequence homology and homogeneity are defined as the percentage of amino acid residues in the candidate sequence relative to the amino acid sequence of the aforementioned protein after aligning the amino acid sequence and the candidate sequence of the aforementioned protein and introducing gaps. If necessary, conservative substitutions as part of sequence homogeneity are not considered in order to obtain maximum percentage sequence homogeneity. N-terminal, C-terminal or internal elongation, deletion or insertion of the amino acid sequence of the aforementioned protein is not to be construed as a sequence affecting sequence homology or homology. Further, the sequence homogeneity may be determined by common standard methods used to compare similar portions of the amino acid sequences of two polypeptides. Computer programs such as BLAST or FASTA align the two polypeptides so that their respective amino acids are optimally matched with each other (in accordance with the full length sequence of one or two sequences or the predicted portion of one or two sequences). The program provides a default opening penalty and default gap penalty, and provides scoring metrics such as PAM250 (Standard Scoring Matrix; Dayhoff et al., in Atlas of Protein Sequence and Structure, vol 5, supp. 3, 1978) as used in conjunction with a computer program. For example, the percentage homogeneity may be calculated as follows: The total number of identical matches is multiplied by 100 and then the result is divided by the sum of the length of the longer sequence in the matched span and the number of gaps introduced into the longer sequence to align the two sequences.

The present inventors isolated and identified the *Vibrio* sp. DHG strain from sea microalgae sludge and deposited the *Vibrio* sp. DHG strain with the Korea Institute of Biotechnology and Biotechnology Center on Apr. 6, 2017 and received the accession number KCTC13239BP. The *Vibrio* sp. DHG strain has a very high growth rate in the minimum medium and nutrient medium compared to microorganisms such as *Escherichia coli* and is resistant to high initial sugar/salt concentrations.

Another aspect of the present disclosure provides a transformed *Vibrio* sp. DHG strain in which a gene encoding a gamma protein represented by a nucleotide sequence of SEQ ID NO: 6 is introduced into the *Vibrio* sp. DHG strain.

Figure 9:
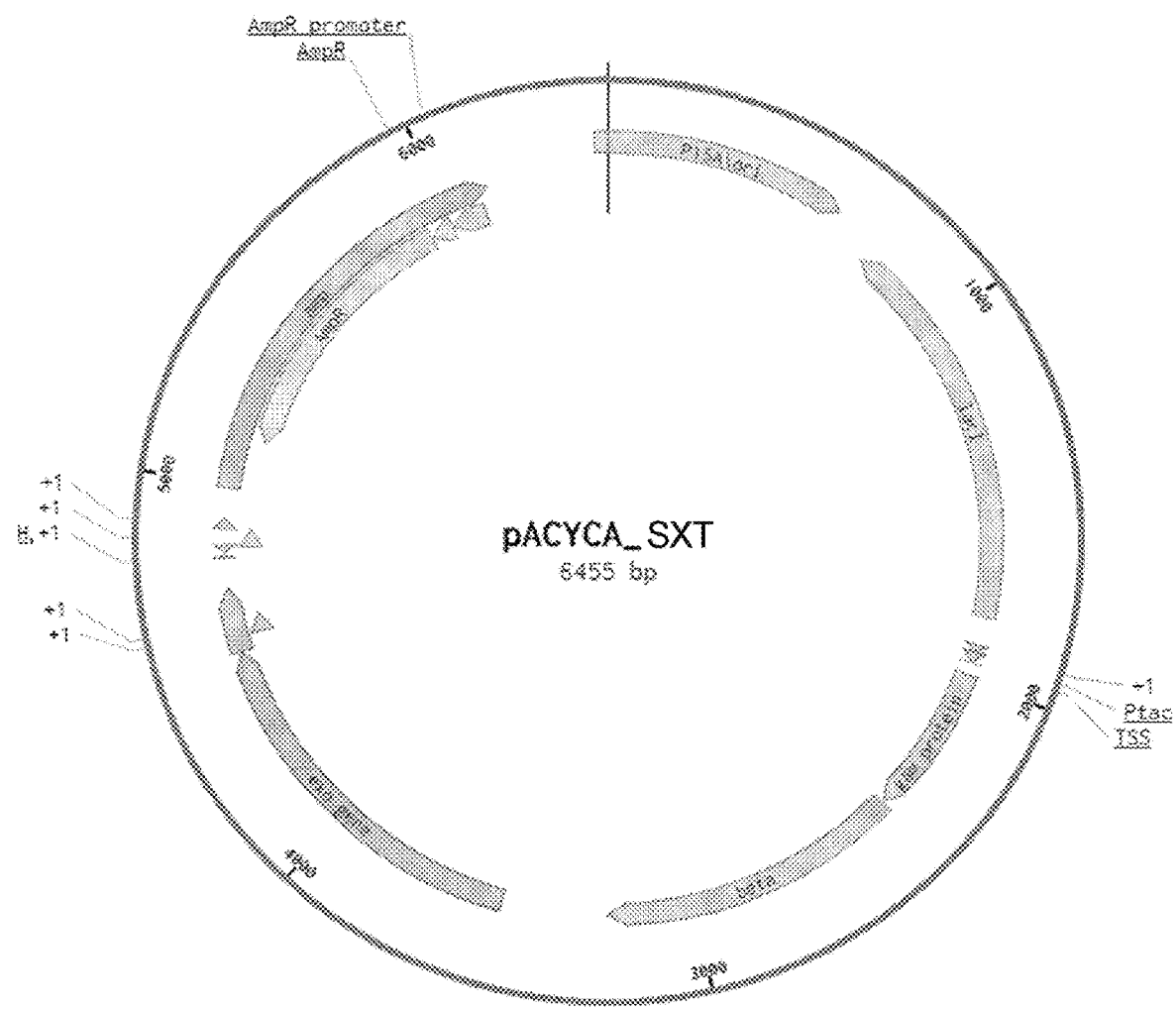
FIG. 9 shows a cleavage map of a plasmid pACYCA_SXT according to the present disclosure for gamma protein expression.

In a preferred embodiment of the present disclosure, the gamma gene is preferably introduced into the *Vibrio* sp. DHG strain using the vector pACYCA_SXT shown in FIG. 9.

Since the transformed DHG strain in accordance with the present disclosure comprises the SXT recombination system, the strain may be transformed using a plasmid as it is for improving *E. coli*, which has been conventionally used. Through the transformation, the strain can be produced capable of producing the high value-added compounds.

Yet another aspect of the present disclosure provides a transformed strain for lycopene production, in which a crtEBI gene represented by a nucleotide sequence of SEQ ID NO: 9 is introduced into the transformed DHG strain.

In one embodiment of the present disclosure, the transformed strain for lycopene production may be obtained by additionally introducing the idi gene represented by the nucleotide sequence of SEQ ID NO: 10 into the transformed DHG strain. In addition, the transformed strain for lycopene production may be obtained by additionally introducing the ispA gene represented by the nucleotide sequence of SEQ ID NO: 11 into the transformed DHG strain. The idi and ispA genes may be introduced simultaneously with the crtEBI gene or may be introduced sequentially therewith. In one embodiment of the present disclosure, the crtEBI, idi and ispA genes were introduced into the transformed DHG strain using the vector pACYC_idi_ispA_crtEBI described in FIG. 17.

In another embodiment of the present disclosure, the transformed strain for lycopene production may be obtained by additionally introducing the dxs gene represented by the nucleotide sequence of SEQ ID NO: 12 into the transformed DHG strain. Further, the dxs gene may be introduced simultaneously or sequentially with the crtEBI gene. The idi and/or ispA genes may be introduced simultaneously or sequentially with the crtEBI gene. However, the present disclosure is not limited thereto.

Figure 18:
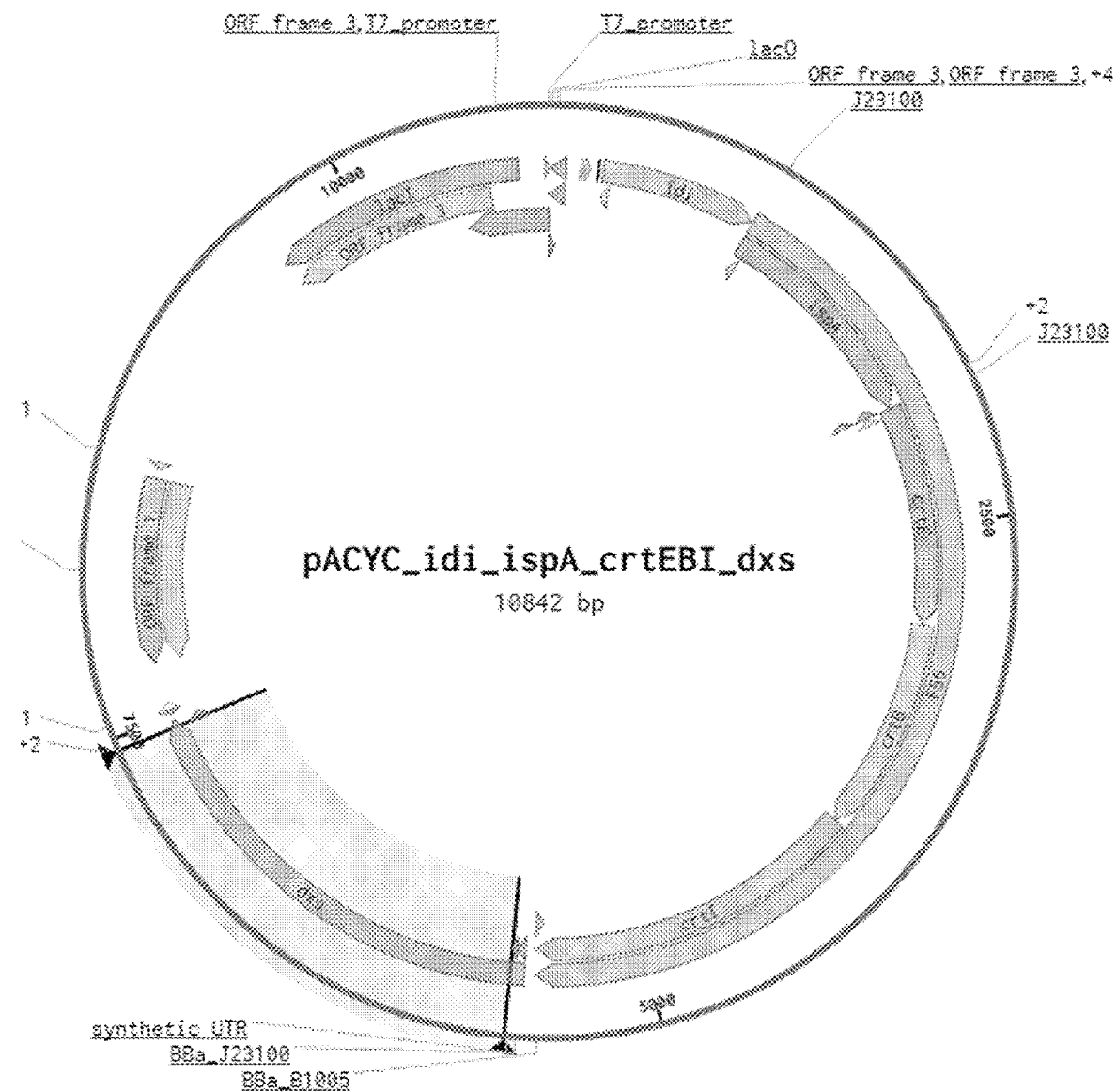
FIG. 18 shows a map of a plasmid pACYC_idi_isopA_crtEBI_dxs for lycopene production according to the present disclosure.

In one embodiment of the present disclosure, the crtEBI, dxs, idi and ispA genes were introduced simultaneously into the transformed DHG strain. The genes were introduced into the transformed DHG strain using the vector pACYC_idi_ispA_crtEBI_dxs represented by the cleavage map shown in FIG. 18.

Yet another aspect of the present disclosure provides a transformed strain for producing 2,3-butanediol, in which one or more genes selected from the group consisting of a budA gene represented by a nucleotide sequence of SEQ ID NO: 13, a budB gene represented by a nucleotide sequence of SEQ ID NO: 14 and a budC gene represented by a nucleotide sequence of SEQ ID NO: 15 are introduced into the transformed DHG strain.

Figure 14:
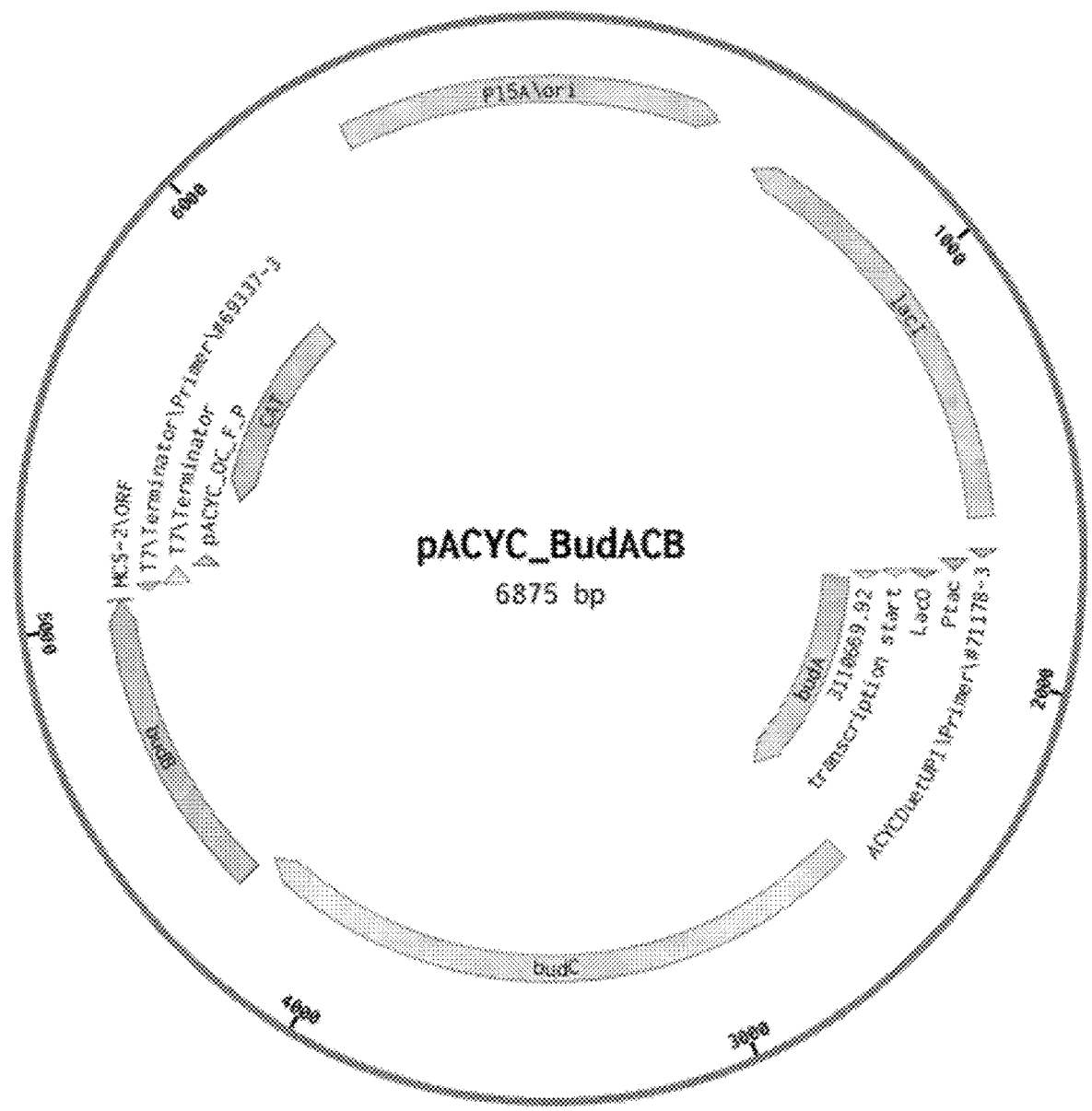
FIG. 14 shows a map of a plasmid pACYC_BudACB for 2,3-butanediol production according to the present disclosure.

In one embodiment of the present disclosure, a budACB operon composed of the budA, budB and budC genes was introduced into the transformed DHG strain using a vector pACYC_BudACB represented by the cleavage map shown in FIG. 14.

Figure 10:
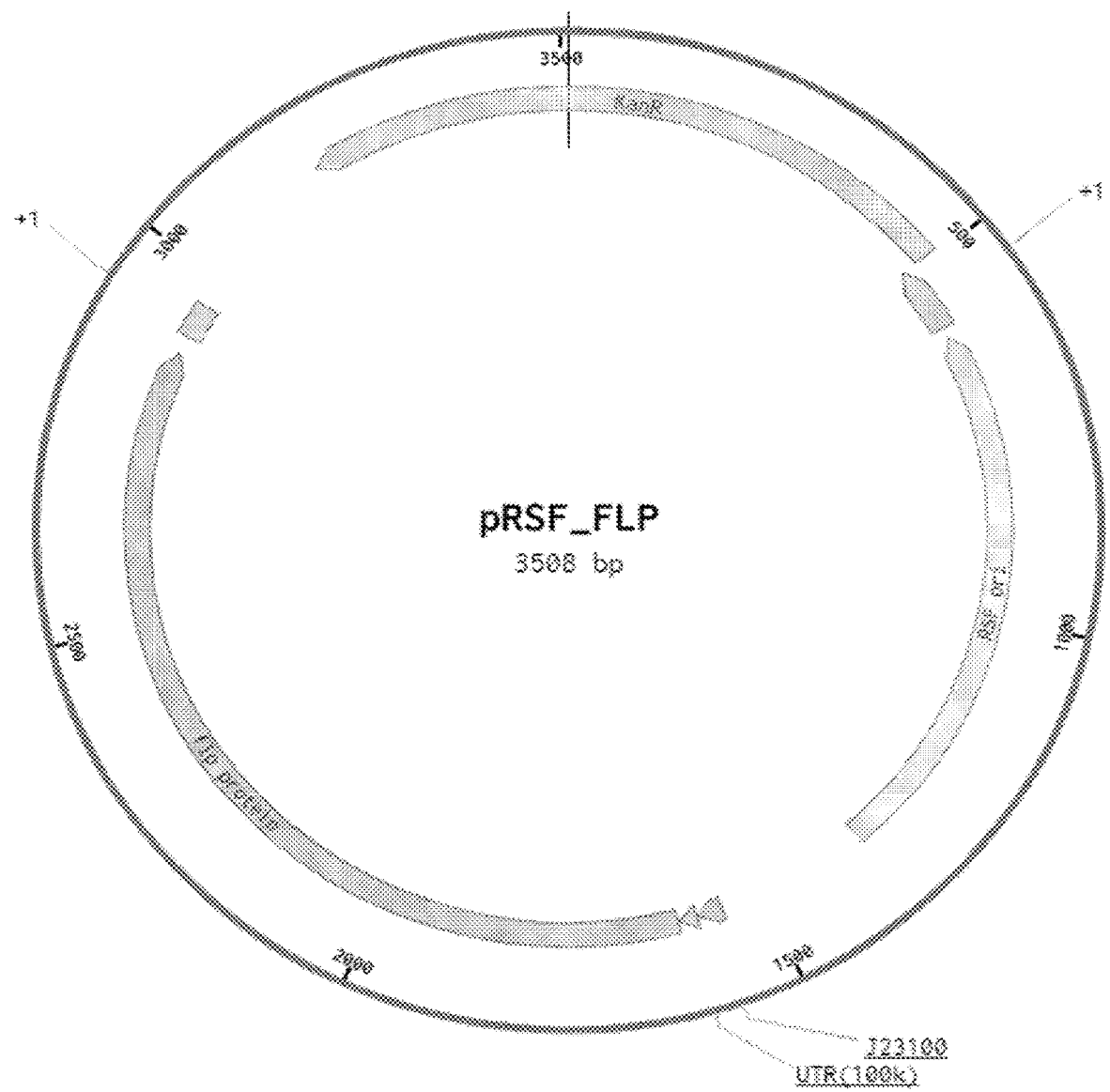
FIG. 10 shows a cleavage map of a plasmid pRSF_FLP comprising an antibiotic resistance gene according to the present disclosure.

In another embodiment of the present disclosure, in order to improve the productivity and yield of 2,3-butanediol, the transformed strain for producing 2,3-butanediol may be obtained by deleting one or more genes selected from the group consisting of the ldhA gene encoding the enzyme producing lactic acid, frdABCD operon encoding enzymes producing succinic acid and pflB gene encoding an enzyme converting pyruvate to acetyl-CoA from the *Vibrio* sp. DHG strain. More specifically, the transformed strain for producing 2,3-butanediol may be obtained by deleting one or more genes selected from the group consisting of ldhA gene represented by the nucleotide sequence of SEQ ID NO: 16, frdA gene represented by the nucleotide sequence of SEQ ID NO: 17, frdB gene represented by the nucleotide sequence of SEQ ID NO: 18, frdC gene represented by the nucleotide sequence of SEQ ID NO: 19, frdD gene represented by the nucleotide sequence of SEQ ID NO: 20, and pflB gene represented by the nucleotide sequence of SEQ ID NO: 21 from the DHG strain. The gene deletion may use pRSF_FLP as a vector represented by the cleavage map shown in FIG. 10. The present disclosure is not limited thereto.

Yet another aspect of the present disclosure provides a method for producing lycopene, the method comprising culturing the transformed strain for lycopene production.

Yet another aspect of the present disclosure provides a method for producing 2,3-butanediol, the method comprising culturing the transformed strain for producing the 2,3-butanediol.

The medium and other culture conditions used for the cultivation of the microorganisms in accordance with the present disclosure may be any medium used for the cultivation of microorganisms of the *Vibrio* sp. DHG. However, the requirements of the microorganisms in accordance with the present disclosure should be satisfactorily met. Preferably, the microorganism in accordance with the present disclosure may be incubated in a conventional medium containing a suitable carbon source, nitrogen source, amino acids, vitamins and the like under aerobic conditions while controlling the temperature, pH and the like.

In a preferred embodiment of the present disclosure, the medium may contain sugar or sugar alcohol as a carbon source. More specifically, the medium may contain at least one selected from the group consisting of glucose, mannitol, sucrose, arabinose, galactose, glycerol, xylose, mannose, fructose, lactose, maltose, sucrose, alginic acid, cellulose, dextrin, glycogen, hyaluronic acid, lentinan, Zymosan, chitosan, glucan, lignin and pectin. Preferably, the medium may contain at least one selected from the group consisting of glucose, mannitol, alginic acid, sucrose, arabinose, galactose and glycerol. However, the present disclosure is not limited thereto. The inorganic compound in the medium may include sodium chloride, calcium chloride, iron chloride, magnesium sulfate, iron sulfate, manganese sulfate and calcium carbonate. In addition, amino acids, vitamins and appropriate precursors may be contained in the medium. These media or precursors may be added batchwise or continuously to the culture.

During the culture, compounds such as ammonium hydroxide, potassium hydroxide, ammonia, phosphoric acid and sulfuric acid may be added to the culture in an appropriate manner to adjust the pH of the culture. Further, during culturing, antifoaming agents such as fatty acid polyglycol esters may be used to inhibit bubble generation. Further, in order to maintain the aerobic state of the culture, oxygen or oxygen containing gas may be injected into the culture, and in order to maintain anaerobic and aerobic states, gas may not be injected or nitrogen, hydrogen or carbon dioxide gas may be injected.

The temperature of the culture may usually be set to 27° C. to 37° C., preferably 30° C. to 35° C. The incubation period may continue until the desired amount of useful substance is obtained. Preferably, the cell may be incubated for 10 to 100 hours.

The compound produced at the culturing stage in accordance with the present disclosure (lycopene or 2,3-butanediol) may be further subjected to a purification or obtaining step. A method for obtaining itaconic acid from microorganisms or cultures may be used by methods known in the art, such as centrifugation, filtration, anion exchange chromatography, crystallization and HPLC, but are not limited to these examples.

The obtaining step may include a purification process. Those skilled in the art may select and utilize one as needed from a variety of known purification processes.

Yet another aspect of the present disclosure provides provide an expression cassette comprising a synthetic 5' UTR (untranslated region), a promoter and a target gene.

One embodiment of the present disclosure provides an SXT recombinant system expression cassette comprising a synthetic 5' UTR (untranslated region), a promoter and a target gene, a flippase gene expression cassette, a crtEBI gene expression cassette or a budACB operon expression cassette.

One embodiment of the present disclosure provides an SXT recombinant system expression cassette comprising a synthetic 5' UTR (untranslated region), a promoter represented by one or more nucleotide sequences selected from the group consisting of SEQ ID NOs: 22 to 35 and 56, and one or more genes selected from the group consisting of genes encoding beta, exo and gamma proteins. More specifically, the synthetic 5' UTR is preferably represented by the nucleotide sequence of SEQ ID NO: 57.

One embodiment of the present disclosure provides a flippase gene expression cassette comprising a synthetic 5' UTR (untranslated region), a promoter represented by one or more nucleotide sequences selected from the group consisting of SEQ ID NOs: 22 to 35 and 58, and a gene encoding flippase. More specifically, the synthetic 5' UTR is preferably represented by a nucleotide sequence of SEQ ID NO: 59. Further, the flippase gene expression cassette may further comprise an idi gene expression cassette or an ispA gene expression cassette. The idi gene expression cassette preferably comprises a synthetic 5' UTR represented by the nucleotide sequence of SEQ ID NO: 65, a promoter represented by one or more nucleotide sequences selected from the group consisting of SEQ ID NOs: 22 to 35 and 64, and an ispA gene. Further, the ispA gene expression cassette may preferably comprise a synthetic 5' UTR represented by the nucleotide sequence of SEQ ID NO: 67, a promoter represented by one or more nucleotide sequences selected from the group consisting of SEQ ID NOs: 22 to 35 and 66, and a dxs gene.

One embodiment of the present disclosure provides a crtEBI gene expression cassette comprising a synthetic 5' UTR (untranslated region), a promoter represented by one or more nucleotide sequences selected from the group consisting of SEQ ID NOs: 22 to 35 and 60, and a crtEBI gene. In this connection, the synthetic 5' UTR is preferably represented by the nucleotide sequence of SEQ ID NO: 61.

One embodiment of the present disclosure provides a budACB operon expression cassette comprising a synthetic 5' UTR (untranslated region), a promoter represented by one or more nucleotide sequences selected from the group consisting of SEQ ID NOs: 22 to 35 and 68, and at least one gene selected from the group consisting of genes coding BudA, BudC and BudB proteins.

As used herein, the term "5' UTR (untranslated region)" refers to an untranslated region at a 5' terminal and 3' terminal of the mRNA. Typically, the 5' untranslated region (5' UTR) performs several functions in the gene expression process, the most important of which involves in the regulation of mRNA translation efficiency. The nucleotide sequence of the 5' UTR at an adjacent upper portion of the translation initiation codon has been reported to affect the efficiency of the translation step. The 5' UTR is composed of nucleotide of 100 bases or more in length. The 3' UTR has a length of a few kilo bases longer than the 5' UTR. Further, the results of studies reported that eukaryotes have a ribosome binding site sequence as a sequence belonging to the 5' UTR which is not a fixed position such as the Shine-Dalgarno sequence which is known as a ribosome binding site sequence located in the 5' UTR in prokaryotes.

As used herein, the term "expression cassette" refers to a unit cassette that contains a promoter and a gene encoding a target protein and may be expressed to produce a target protein operably linked to a downstream of the promoter. Inside or outside of the expression cassette, a variety of factors that may help the efficient production of the protein of interest may be contained. In the target protein expression cassette, a gene encoding the target protein may be specifically operably linked to a downstream of the promoter sequence.

The "operably linked" means that the gene sequence and the promoter sequence are functionally linked to each other so that the nucleic acid sequence having the promoter activity according to the present disclosure initiates and mediates the transcription of the gene encoding the protein of interest. The operable linkages may be made using genetic recombination techniques known in the art. Site-specific DNA cleavage and ligation may be made using, but are not limited to, cleavage and ligation enzymes in the art.

As used herein, the term "target protein" refers to a protein to be expressed from a microorganism. Specifically, the target protein may include any protein to be expressed from a recombinant microorganism without restriction. Examples thereof include, but are not limited to, proteins, flippase, lycopene producing enzyme, and BudACB constituting the SXT recombination system.

The recombinant gene expression cassette may be inserted into chromosome of a host cell to prepare recombinant microorganisms. For those skilled in the art to which the present disclosure belongs, it is obvious that the insertion of the recombinant gene expression cassette into the genomic chromosome of the host cell will have the same effect from the introduction of the recombinant vector into the host cell.

The recombinant gene expression cassette may be inserted into chromosome of a host cell to prepare recombinant microorganisms. For those skilled in the art to which the present disclosure belongs, it is obvious that the insertion of the recombinant gene expression cassette into the genomic chromosome of the host cell will have the same effect from the introduction of the recombinant vector into the host cell.

A method of inserting the recombinant gene expression cassette into a chromosome of a host cell may include a commonly known gene engineering method. One example thereof is a method using a retroviral vector, adenovirus vector, adeno-associated virus vector, herpes simplex virus vector, poxvirus vector, lentiviral vector or non-viral vector.

As used herein, the term "promoter" refers to a non-translated nucleic acid sequence of an upstream of a coding region, containing a binding site to polymerase and having transcription initiation activity of a promoter downstream gene to mRNA, that is, a DNA region that binds to polymerase to allow initiation of transcription of a gene. The promoter may be located at a 5' site of the mRNA transcription initiation site.

The promoter nucleic acid molecule according to the present disclosure may be isolated or prepared using standard molecular biology techniques. For example, the promoter nucleic acid molecule according to the present disclosure may be prepared using standard synthesis techniques using an automated DNA synthesizer. However, the present disclosure is not limited thereto.

In accordance with the present disclosure, the promoters may result in expression of a target gene operably linked to a nucleic acid molecule having the promoter activity in a desired microorganism.

Further, the promoter sequence according to the present disclosure may be easily modified by those skilled in the art by conventionally known mutagenesis, such as directional evolution and site-specific mutagenesis. Thus, the promoter may include nucleotide sequences having homology of at least 70%, specifically at least 80%, more specifically at least 90%, more specifically at least 95%, even more specifically at least 98%, and most specifically, at least 99% with the nucleotide sequence of the SEQ ID NOs: 22 to 35, without any limitation. Further, any nucleotide sequence obtained by deletion, modification, substitution, or addition of a portion of the nucleotide sequence having the above ranged homology and having the promoter activity should be interpreted to fall within the scope of the present disclosure.

As used herein, the term "homology" refers to a percentage of identity between two polynucleotide or polypeptide moieties. Homology between sequences from one moiety to another may be determined by known techniques. For example, the homology may be determined by directly aligning sequence information between two polynucleotide molecules or two polypeptide molecules, such as parameters including scores, identities, and similarities, or aligning the sequence information using a computer program readily available (e.g., BLAST 2.0). Further, the homology between polynucleotides may be determined by hybridization of polynucleotides under conditions of stable double stranding between homologous regions, followed by decomposition thereof with single-strand-specific nucleases to determine a size of the decomposed fragment.

According to another aspect according to the present disclosure, there is provided a recombinant vector comprising the SXT recombinant system expression cassette, flippase gene expression cassette, crtEBI gene expression cassette or BudACB operon expression cassette.

As used herein, the term "vector" refers to a DNA preparation containing a DNA sequence operably linked to a suitable regulatory sequence capable of expressing DNA in a suitable host. The vector may be plasmids, phage particles or simply potential genomic inserts. Once the vector has been transformed into a suitable host, the vector may replicate and function independently of the host genome, or in some cases may be integrated into the genome itself. Since plasmids are the most commonly currently used form of the vector, the "plasmid" and "vector" are sometimes used interchangeably in the present disclosure. For purposes of the present disclosure, it is preferable to use a plasmid vector. Typical plasmid vectors that may be used for this purpose may have a structure including (a) a replication initiation point that allows for efficient replication to contain several to several hundred plasmid vectors per host cell, (b) an antibiotic resistance gene that allows selection of a host cell transformed with a plasmid vector, and (c) a restriction enzyme cleavage site into which foreign DNA fragments may be inserted. Although no suitable restriction enzyme cleavage site is present, synthetic oligonucleotide adapters or linkers according to conventional methods may be used to facilitate ligation of the vector and foreign DNA. After the ligation, the vector should be transformed into the appropriate host cell. The transformation may be easily accomplished using calcium chloride method or electroporation or the like.

As is well known in the art, in order to raise the expression level of a transfected gene in a host cell, the gene must be operably linked to transcriptional and translational expression control sequences that function in the selected expression host. Preferably, the expression control sequence and the corresponding gene are contained in one recombinant vector containing the bacterial selection marker and the replication start point.

As used herein, the "recombinant vector" refers to a recombinant DNA molecule containing the desired coding sequence and the appropriate nucleic acid sequence necessary to express the coding sequence operably linked in a specific host organism. The recombinant vectors may preferably contain one or more selectable markers. The marker is typically a nucleic acid sequence having properties that may be selected by chemical methods, such as all genes that may distinguish transformed cells from non-transformed cells. Examples thereof include, but are not limited to, antibiotic resistance genes such as ampicillin, kanamycin, G418, bleomycin, hygromycin, chloramphenicol, and the like. The present disclosure may not be limited thereto. The maker may be suitably selected by those skilled in the art.

[Best Mode]

Hereinafter, the present disclosure will be described in more detail with examples. These examples are intended only to illustrate the present disclosure. It will be apparent to those of ordinary skill in the art that the scope of the present disclosure is not to be construed as being limited by these examples.

Example 1. Isolation and Identification of *Vibrio* sp. DHG Strain from Sea Microalgae Sludge In order to secure microorganisms that may grow rapidly in high concentration salts, samples were taken from seashore microalgae sludge and cultured in a laboratory.

In this connection, a composition of the medium as used is as follows.

NaCl 30 g/L
$(NH_4)_2SO_4$ 5 g/L
$K_2HPO_4$ 2 g/L
$MgSO_4 7H_2O$ 0.5 g/L
Alginate 10 g/L
ATCC Trace mineral solution 2 ml/L It was identified that the incubation of the samples in the medium leads to rapid growth thereof. Then, a single colony was separated.

16S rDNA sequence (SEQ ID NO: 1) was analyzed to determine the species specificity of the isolated microorganism, and found to belong to *Vibrio* sp.

The present inventors named the microorganism as the *Vibrio* sp. DHG, and then deposited at the Korea Institute of Bioscience and Biotechnology on Apr. 6, 2017. The accession number KCTC13239BP was allocated thereto.

Example 2. Metabolic Carbon Source Analysis of *Vibrio* sp. DHG and Measurement of Growth Rate Thereof

*Vibrio* sp. DHG was cultured in a minimal medium with various carbon sources as the only carbon source in order to determine the type of a carbon source that the *Vibrio* sp. DHG can metabolize and the corresponding growth rate thereof (30° C., 250 rpm).

A detailed medium composition for culturing the microorganism is as follows.

NaCl 30 g/L
$(NH_4)_2SO_4$ 5 g/L
$K_2HPO_4$ 2 g/L
$MgSO_4 7H_2O$ 0.5 g/L
Carbon source 10 g/L
ATCC Trace mineral solution 2 ml/L The specific growth rate of the *Vibrio* sp. DHG strain is shown in FIG. 1.

As shown in FIG. 1, it may be identified that when considering that the glucose metabolism rate by *E. coli* is 0.5 to 0.6, the *Vibrio* sp. DHG strain is able to use all the carbon sources in the comparative bacteria as the only carbon source and grows at a high rate (>0.8 $h^{-1}$). In addition, the carbon source metabolism per cell of the *Vibrio* sp. DHG strain was similar to or higher than the metabolism of glucose by *E. coli*. The result indicates that the strain can convert carbon sources quickly in biorefinery processes.

Example 3. Resistance Test to Initial Sugar (Substrate) Concentration

Figure 2:
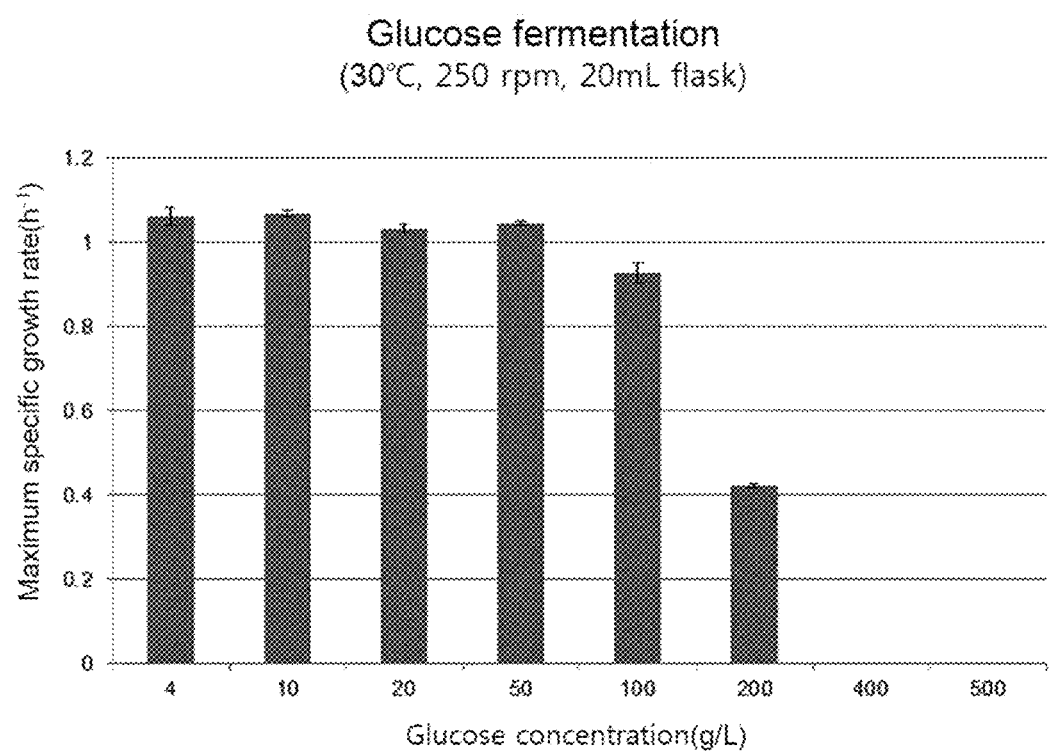
FIG. 2 shows a resistance of a *Vibrio* sp. DHG strain to an initial sugar concentration according to the present disclosure.

In order to identify the growth rate according to the initial sugar concentration in the incubator, we tried to test the resistance to glucose which exhibited the highest growth rate in the previous experiment. To do this, we added 20 mL of medium with different initial concentrations to the flask of a 350 mL, and added the *Vibrio* sp. DHG thereto at $OD_{600}$ of 0.05. Then, the initial growth rates thereof were compared with each other. FIG. 2 shows a result of identifying the growth rate based on the initial sugar concentration.

As shown in FIG. 2, the *Vibrio* sp. DHG maintained a high growth rate at an initial substrate concentration of about 100 g/L.

Example 4. Resistance Test to Salt Concentration in Medium

To test the resistance of the *Vibrio* sp. DHG to salts in the medium, we compared the growth rates based on concentrations of salts that may be contained during fermentation. To do this, we added 20 mL of the medium with different initial concentrations to the flask of a 350 mL and added the *Vibrio* sp. DHG thereto at $OD_{600}$ of 0.05. Then, the initial growth rates thereof were compared with each other. The result is shown in FIG. 3.

Figure 3:
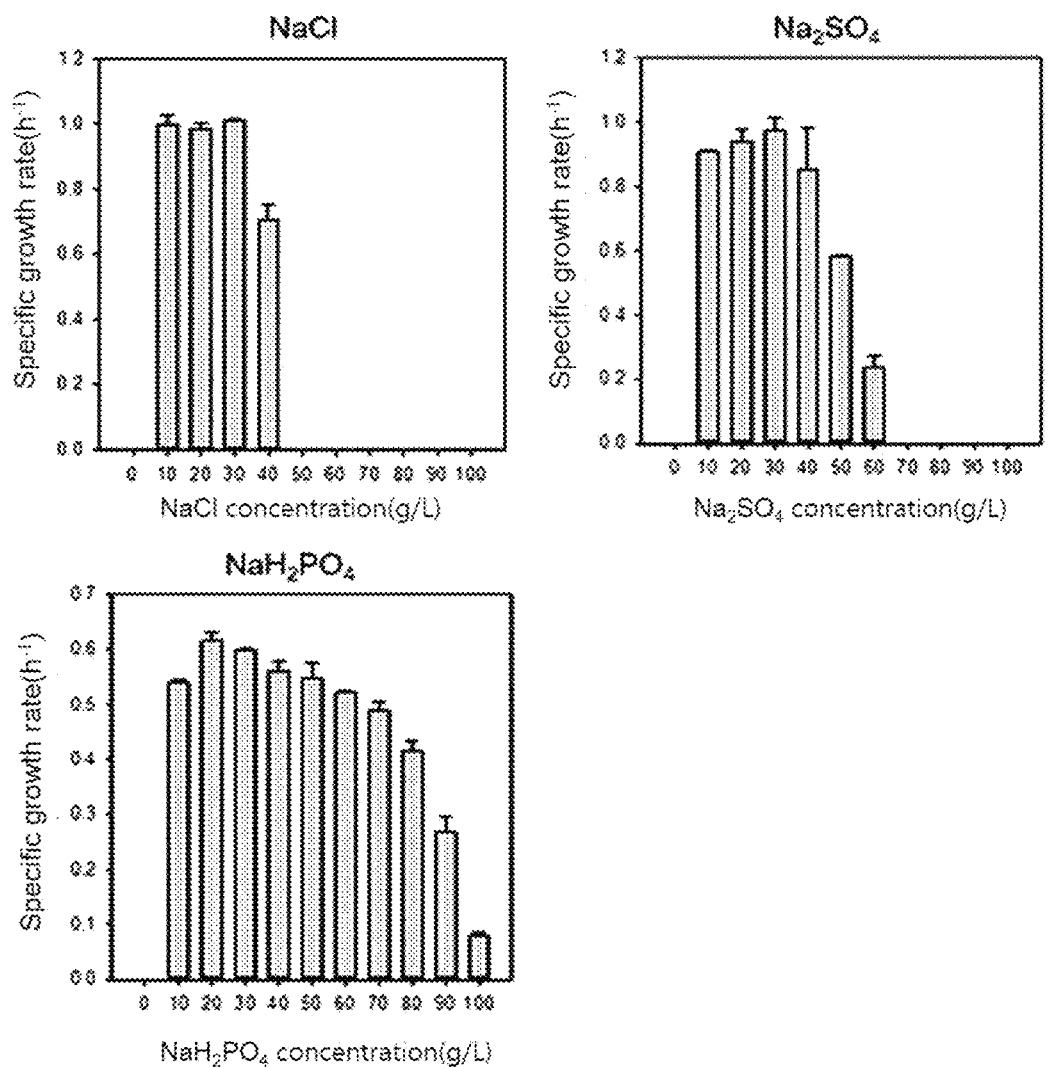
FIG. 3 shows a resistance of a *Vibrio* sp. DHG strain to a salt concentration in the medium to according to the present disclosure.

As shown in FIG. 3, the *Vibrio* sp. DHG was identified to grow in the presence of 10 to 40 g/L NaCl, 10 to 60 g/L $Na_2SO_4$ and about 10 to 100 g/L $NaH_2PO_4$. In conclusion, the *Vibrio* sp. DHG was identified to have high resistance to the salt.

Example 5. Plasmid Introduction for Transformation of *Vibrio* sp. DHG Strain

In general, the most basic method for transforming microorganisms is to introduce plasmids thereto. For efficient transformation, it is important to introduce plasmids commonly used in microorganisms such as *E. coli*.

In order to identify that the plasmid is introduced into the *Vibrio* sp. DHG strain, the following experiment was performed with reference to the transforming method of *Vibrio natriegens*.

(1) First, a seed cultured overnight in a brain heat infusion (BD) medium was inoculated to a fresh medium at a ratio of 1/100, and then incubated at 37° C. at 200 rpm until the OD reaches 0.6.

(2) When the OD reached 0.6, the flask was placed on ice for 20 minutes and centrifuged at 4500 rpm for about 15 minutes to collect cells.

(3) After the cells were collected, 10 mL of sterile electroporation buffer (680 mM sucrose, 7 mM $K_2HPO_4$, pH 7) was added thereto, and then the cell pellet was resuspended, washed, and centrifuged again at 4500 rpm.

(4) This process was repeated four times.

(5) Finally, an appropriate amount of electroporation buffer was added thereto to resuspend the cells to adjust the OD to 16.

(6) After adding 500 ng or more of the plasmid to be used for transformation thereto, electroporation was performed with an electric shock of 0.8 kV.

In order to identify the transformation of the cells, we overnight cultured the cells in a plate containing an appropriate amount of antibiotics, and performed colony PCR to identify the presence of the plasmid in the microorganisms. The results are shown in FIG. 4.

Figure 4:
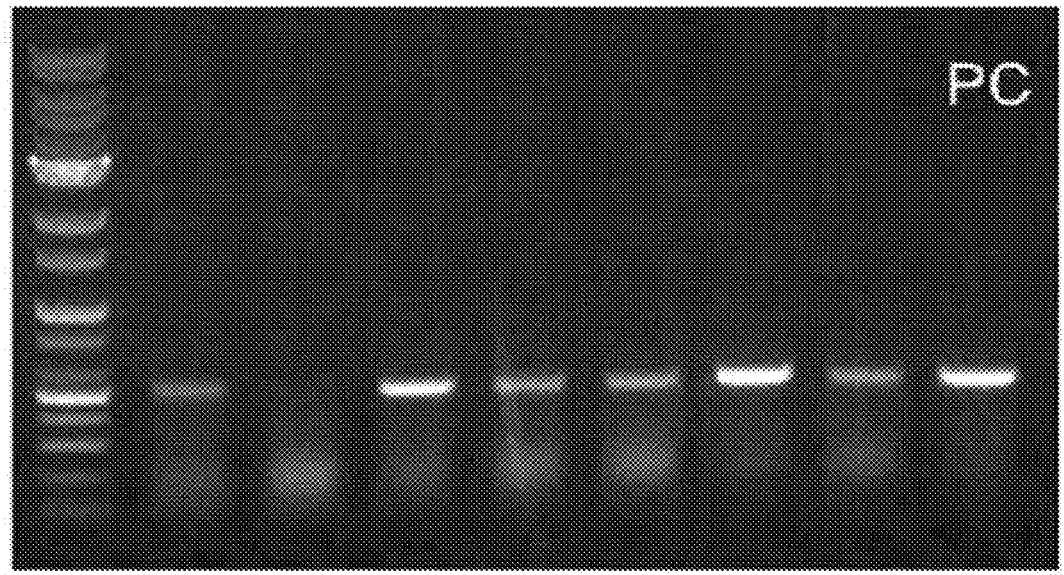
FIG. 4 shows a result of checking whether plasmid pACYC or pUC are introduced into a *Vibrio* sp. DHG strain via colony PCR according to the present disclosure.
Figure 4:
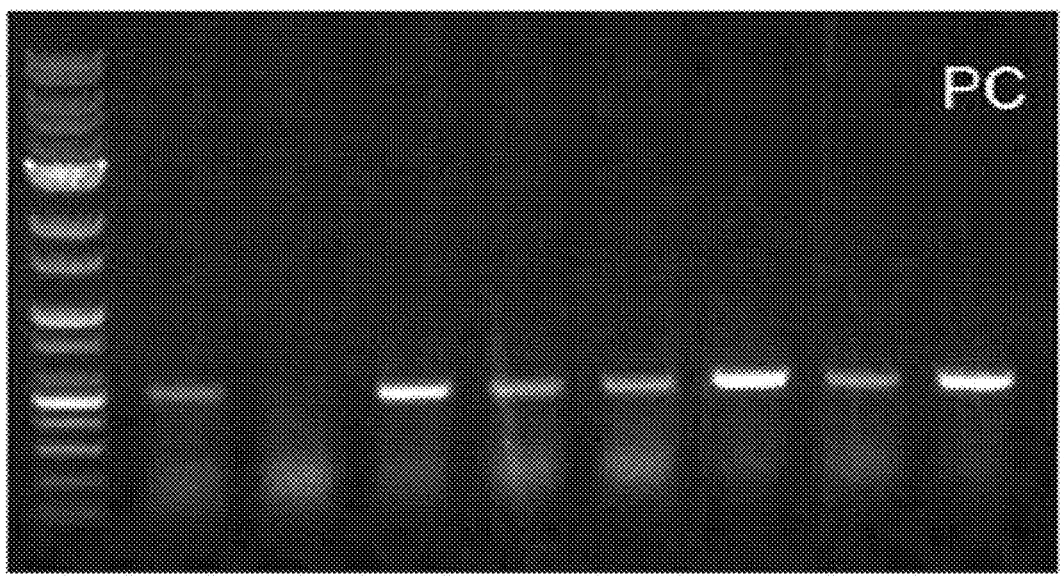

As shown in FIG. 4, it was confirmed that plasmids pACYC and pUC were introduced thereto respectively.

Figure 5:
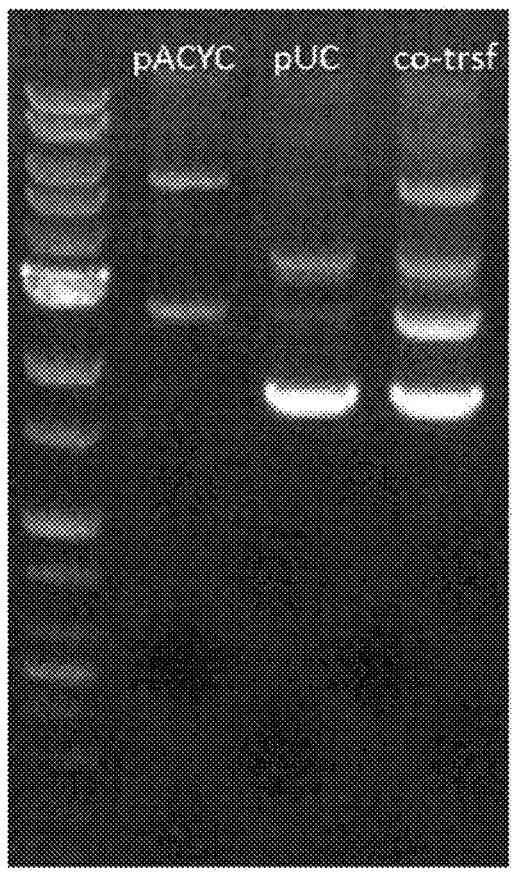
FIG. 5 shows a result of checking whether plasmid pACYC or pUC are introduced into a *Vibrio* sp. DHG strain via colony PCR according to the present disclosure.

Further, to further identify that two or more plasmids may be introduced into the microorganism in the same manner, the plasmids pACYC and pUC were transformed sequentially. As shown in FIG. 5, it was identified that, after liquid culturing the plasmid in a BHI medium and then purifying the plasmid, the two plasmids coexist and are secured when being electrophoresed.

Example 6. Heterologous Protein Expression in *Vibrio* sp. DHG Strain

The fast growth rate of the *Vibrio* sp. DHG suggests that the desired protein can be produced at a high speed. To this end, we identified the expression of heterologous proteins in the *Vibrio* sp. DHG strain.

Specifically, using the transforming method of Example 5, plasmids capable of expressing heterologous proteins were respectively introduced thereto. The plasmid capable of expressing the heterologous protein is designed such that the fluorescent protein GFP may be expressed under different promoters (PJ23100, Plac, Ptac, PT7, Ptet, Para). The experimental group transformed with each plasmid was cultured in nutrient medium (LBv2). Then, we identified whether the fluorescent protein GFP was produced by the experimental group. The results of identifying the heterologous protein production by the *Vibrio* sp. DHG strain are shown in FIG. 6.

Figure 6:
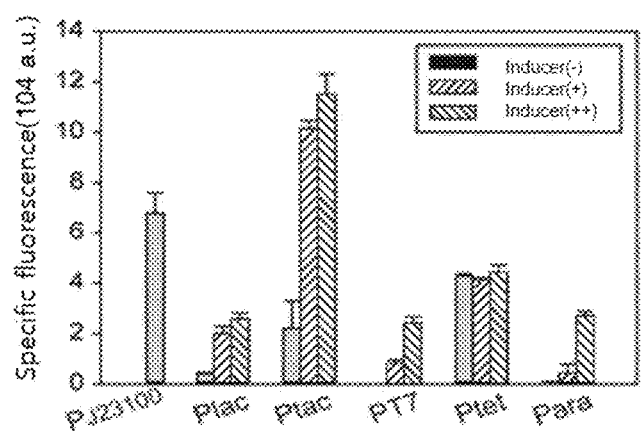
FIG. 6 shows a result of checking a fluorescent expression when transforming the *Vibrio* sp. DHG strain according to the present disclosure with a fluorescent protein expression plasmid as a heterologous protein.
Figure 6:
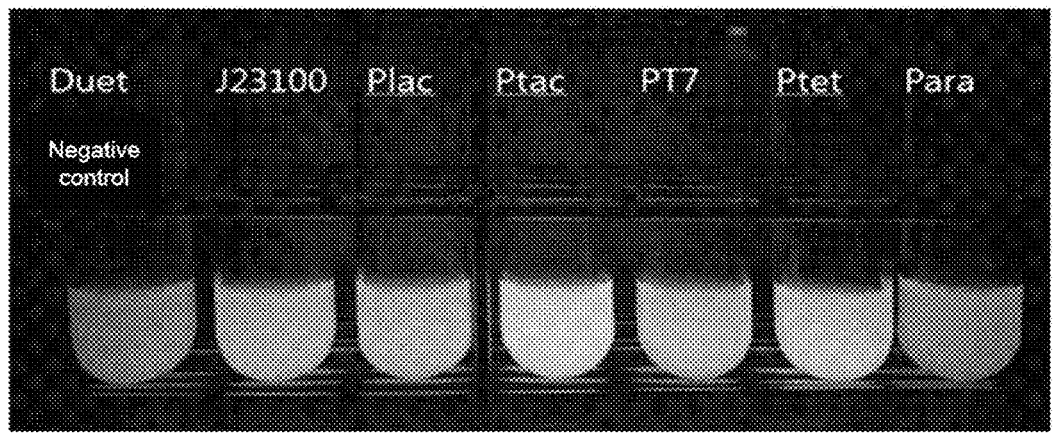

As shown in FIG. 6, the *Vibrio* sp. DHG strain was able to produce heterologous proteins under various promoters.

Example 7. Quantitative Regulation of Transcription Through Constant Promoter Sequences For the redesign of microorganisms, it is very important to quantitatively control the expression level of genes. This may be effectively applied to increasing of biochemical production, such as expansion of metabolic pathways through efficient overexpression of genes, and optimization of carbon flow through optimal expression. In general, such expression control has been largely performed in the transcription and translation stages of gene expression. The amount of expression in the transcription step depends on the sequence of the promoter that determines the affinity with the RNA polymerase. The sequence of −35 and −10 regions among the promoter sequences is known to be very important.

In order to regulate transcription in the *Vibrio* sp. DHG strain, the sequence of the promoter was randomly changed and then the expression level of sGFP was measured to identify the change in the transcription level. Specifically, a random sequence was placed in the −35 and −10 regions using the constant promoter J23100 provided from Parts-registry as a template. After linking the random sequence thereto to express the GFP gene, the plasmids having various sequence libraries were prepared. The promoters using the promoter J23100 as the template are shown in Table 1.

Example 8. Quantitative Control of Translation by Changing 5' UTR Sequence

In the regulation of gene expression in the translation stage, the affinity between the mRNA to be translated and the ribosome responsible for the translation is very important. The most decisive factor to determine this affinity is the 5' UTR sequence, which determines the overall translation efficiency. According to the study of *Escherichia coli*, it was possible to quantitatively control an amount of a target protein by changing the 5' UTR sequence. Conversely, 5' UTR may be designed to produce the amount of the target protein. This method is provided as a web-based tool.

Likewise, in order to regulate translation in the *Vibrio* sp. DHG strain, the 5' UTR sequence linked to the sGFP gene was changed. In this connection, a UTR Library designer (10.1016/j.ymben.2012.10.006, 10.1038/srep04515) program was used to build an unbiased library. The constructed 5' UTR library is shown in Table 2.

TABLE 1

| Samples | Sequence(5'->3') | Standardized relative intensity | SEQ ID NO |
|---|---|---|---|
| Templates | NNNNNNGCTAGCTCAGTCCTAGGKANNNNGCTAGC | | SEQ ID NO: 22 |
| 1 | CTTATGGCTAGCTCAGTCCTAGGGACAGTGCTAGC | 0.053 | SEQ ID NO: 23 |
| 2 | TTTACGGCTAGCTCAGTCCTAGGGATAGTGCTAGC | 0.098 | SEQ ID NO: 24 |
| 3 | CTGACGGCTAGCTCAGTCCTAGGGATAGTGCTAGC | 0.143 | SEQ ID NO: 25 |
| 4 | TTGATGGCTAGCTCAGTCCTAGGGATTATGCTAGC | 0.171 | SEQ ID NO: 26 |
| 5 | TTGATGGCTAGCTCAGTCCTAGGTACAGTGCTAGC | 0.254 | SEQ ID NO: 27 |
| 6 | TTGATGGCTAGCTCAGTCCTAGGTATTGTGCTAGC | 0.288 | SEQ ID NO: 28 |
| 7 | TTGATGGCTAGCTCAGTCCTAGGTACTATGCTAGC | 0.322 | SEQ ID NO: 29 |
| 8 | TTGACGGCTAGCTCAGTCCTAGGTACTGTGCTAGC | 0.420 | SEQ ID NO: 30 |
| 9 | TTGATGGCTAGCTCAGTCCTAGGTACAATGCTAGC | 0.514 | SEQ ID NO: 31 |
| 10 | TTGATGGCTAGCTCAGTCCTAGGTATAGTGCTAGC | 0.579 | SEQ ID NO: 32 |
| 11 | TTGACGGCTAGCTCAGTCCTAGGTATTGTGCTAGC | 0.651 | SEQ ID NO: 33 |
| 12 | TTGATGGCTAGCTCAGTCCTAGGTATAATGCTAGC | 0.813 | SEQ ID NO: 34 |
| 13 | TTGACGGCTAGCTCAGTCCTAGGTACAGTGCTAGC | 1.000 | SEQ ID NO: 35 |

The prepared plasmids were introduced into the *Vibrio* sp. DHG strain, and then, colonies were randomly selected, and cultured in a minimal medium. Fluorescence per cell of the strains as cultured were compared with each other. The results are shown in FIG. 7.

Figure 7:
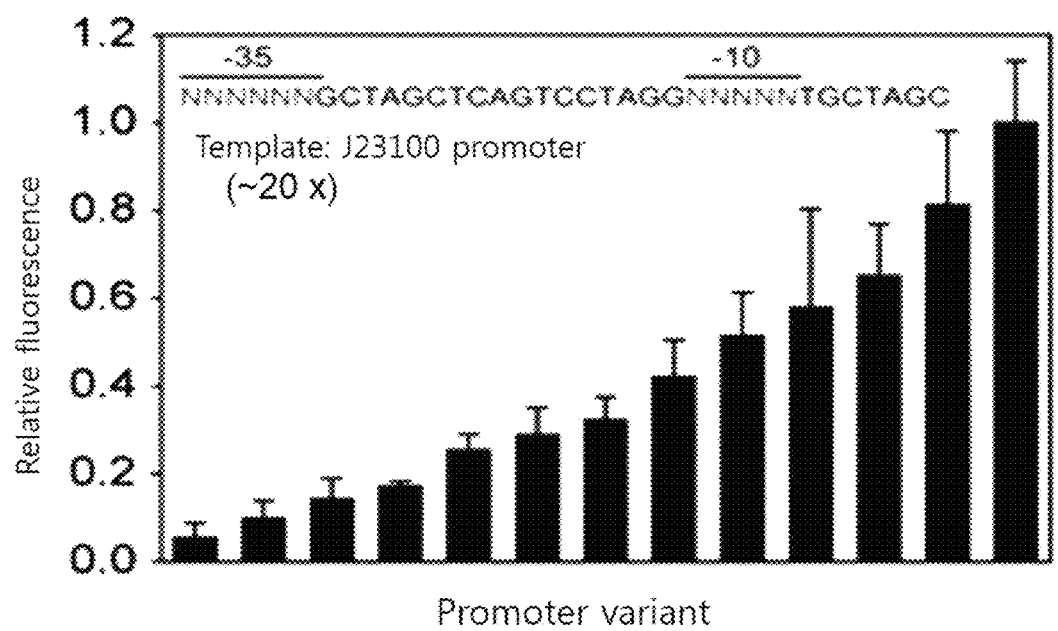
FIG. 7 shows a result of checking a degree of fluorescence expression of the transformed strain based on a synthetic promoter sequence.

As shown in FIG. 7, it was identified that the fluorescence changes by about 20 times depending on the promoter sequence. Thus, it is expected that the promoter may be used to regulate the expression level of the target gene required for bio compound production.

TABLE 2

| Samples | Sequence (5'->3') | ΔG$_{UTR}$ | Measured flourescence intensity | SEQ ID NO: |
|---|---|---|---|---|
| Template | ACGGAGAWTGCTYAAKSAGTCSTTT | | | SEQ ID NO: 36 |
| 1 | ACGGAGATTGCTTAAGCAGTCGTTT | 0.28 | 0.02 | SEQ ID NO: 37 |
| 2 | ACGGAGAATGCTTAATCAGTCGTTT | 1.13 | 0.03 | SEQ ID NO: 38 |
| 3 | ACGGAGATTGCTTAATCAGTCCTTT | 5.98 | 0.04 | SEQ ID NO: 39 |
| 4 | ACGGAGATTGCTTAAGCAGTCGTTT | 0.28 | 0.04 | SEQ ID NO: 40 |
| 5 | ACGGAGAATGCTCAATGAGTCGTTT | -1.22 | 0.12 | SEQ ID NO: 41 |
| 6 | ACGGAGATTGCTTAATGAGTCGTTT | -2.07 | 0.17 | SEQ ID NO: 42 |
| 7 | ACGGAGAATGCTTAATGAGTCGTTT | -2.17 | 0.18 | SEQ ID NO: 43 |
| 8 | ACGGAGAATGCTTAATGAGTCGTTT | -2.17 | 0.21 | SEQ ID NO: 44 |
| 9 | ACGGAGATTGCTTAATGAGTCGTTT | -2.07 | 0.24 | SEQ ID NO: 45 |
| 10 | ACGGAGAATGCTCAAGGAGTCGTTT | -7.22 | 0.69 | SEQ ID NO: 46 |
| 11 | ACGGAGAATGCTTAAGGAGTCGTTT | -8.67 | 0.85 | SEQ ID NO: 47 |
| 12 | ACGGAGATTGCTTAAGGAGTCCTTT | -4.27 | 0.87 | SEQ ID NO: 48 |
| 13 | ACGGAGAATGCTTAAGGAGTCGTTT | -8.67 | 0.98 | SEQ ID NO: 49 |
| 14 | ACGGAGATTGCTTAAGGAGTCGTTT | -8.57 | 1.00 | SEQ ID NO: 50 |

After transforming the sgfp expression plasmid designed to control 5' UTR shown in Table 2 to the *Vibrio* sp. DHG strain, colonies were randomly selected and cultured in minimal medium. Fluorescence per cell of the strains cultured was compared with each other. The results are shown in FIG. 8.

Figure 8:
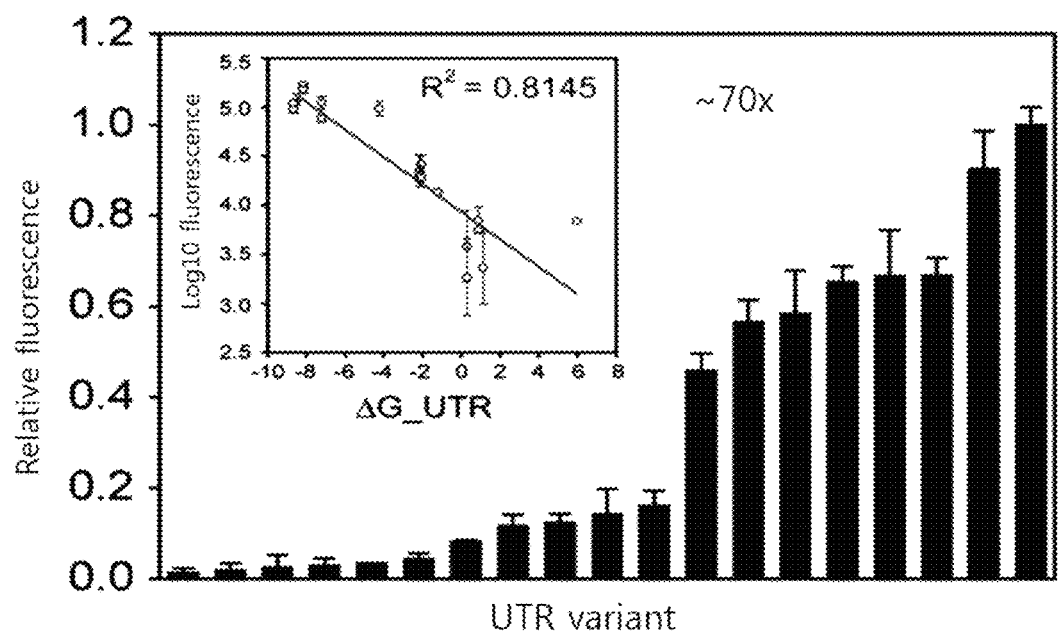
FIG. 8 shows a result of checking a degree of fluorescence expression of the transformed strain based on a 5' UTR sequence.

As shown in FIG. 8, the fluorescence increased by about 70 times based on the 5' UTR sequences. Further, from a result of identifying the 5' UTR sequence, it was identified that the fluorescence per cell had a very high correlation ($R^2$=0.8145) with the predicted expression value based on the UTR sequence. The results indicate that translational regulation of the *Vibrio* sp. DHG strain may be used to optimize various compound production circuits.

Example 9. Genome Engineering of *Vibrio* sp. DHG Strain 9-1. Genome Analysis of *Vibrio* sp. DHG Strain In general, microorganisms do not produce only the target compound, but produce by-products (acetate, lactate, succinate, formate) for several purposes (such as achieving ATP and NAD/NADH balance). However, in order to maximize the production of the desired compound, it is necessary to prevent the production of such by-products. The most representative method for suppressing the production of by-products is to delete the gene from the genome of the microorganism.

The genome engineering of *Vibrio* may be achieved using single-stranded DNA oligos when expressing SXT recombinase in the genome (doi: 10.1101/130088). To this end, the presence or absence of SXT recombinase in the *Vibrio* sp. DHG strain was analyzed based on the decoded genome sequence.

Thus, it was confirmed that the beta and exo proteins constituting the SXT recombinase were present in the *Vibrio* sp. DHG strain. The beta protein is represented by the amino acid sequence of SEQ ID NO: 2, and the gene encoding the beta protein is represented by the nucleotide sequence of SEQ ID NO: 3. Further, the exo protein is represented by the amino acid sequence of SEQ ID NO: 4. The gene encoding the exo protein is represented by the nucleotide sequence of SEQ ID NO: 5.

9-2. Plasmid Construction for Gamma Protein Expression

The SXT recombinase requires the help of gamma proteins in addition to the beta and exo proteins. As a result of analyzing the genome of the *Vibrio* sp. DHG strain, it was identified that there was no gamma protein in the *Vibrio* sp. DHG strain. Thus, a gene encoding a gamma protein derived from lambda phage was introduced into the *Vibrio* sp. DHG strain. The gene encoding the gamma protein is represented by the nucleotide sequence of SEQ ID NO: 6. Specifically, in order to efficiently express these genes, the recombinant enzyme was expressed in the tac promoter showing high transcription efficiency in the *Vibrio* sp. DHG strain. Synthetic 5' UTR was designed to have maximum translation efficiency. As a result, plasmid pACYCA_SXT was constructed. The plasmid pACYCA_SXT is represented by the cleavage map shown in FIG. 9. The sequence is represented by the nucleotide sequence of SEQ ID NO: 51.

9-3. Construction of Plasmids Containing Antibiotic Resistance Gene and flp Flippase Gene To selectively isolate the recombinant cells, antibiotic resistance genes were inserted thereto upon gene deletion and introduction. The antibiotic resistance gene should be easily re-deleted for further genome engineering. Gene deletion method was configured to express the flp flippase derived from *Saccharomyces cerevisiae* as represented by SEQ ID NO: 7 or 8 to recognize the FRT sequences on either side of the selection marker so that the deletion occurs. In *Escherichia coli*, generally, a plasmid called pCP20 is used. Since the plasmid is not transformed into the *Vibrio* sp. DHG strain, thus a new plasmid pRSF_FLP was constructed. The plasmid pRSF_FLP was designed to continuously express flp flippase for rapid FRT sequence recognition and deletion of selectable markers and therefore, was designed to be expressed under the constant promoter J23100. Further, the plasmid pRSF_FLP designed a synthetic 5' UTR with high translation efficiency to facilitate protein expression. The prepared plasmid pRSF_FLP is represented by the cleavage map shown in FIG. 10. The entire sequence is represented by the nucleotide sequence of SEQ ID NO: 52.

9-4. Genome Engineering of *Vibrio* sp. DHG Strain

Figure 11:
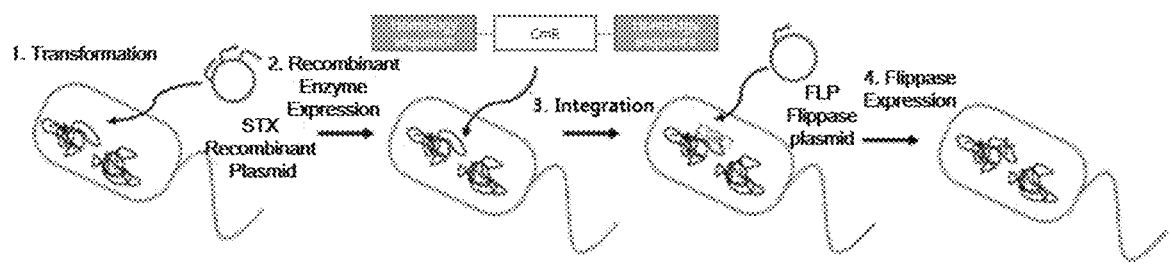
FIG. 11 shows a schematic diagram of a genetic manipulation method of a *Vibrio* sp. DHG strain according to the present disclosure.

A schematic diagram of the genome engineering method for the *Vibrio* sp. DHG strain is shown in FIG. 11.

Figure 12:
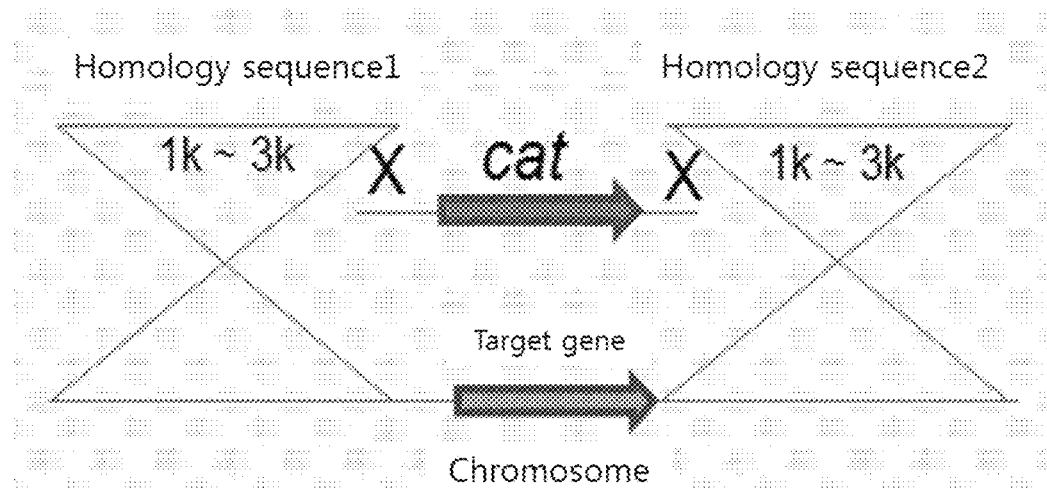
FIG. 12 shows a structure and targeting site of a double stranded DNA used for genetic manipulation of a *Vibrio* sp. DHG strain according to the present disclosure.

Specifically, the plasmid pACYCA_SXT prepared in Example 9-2 was transformed into the *Vibrio* sp. DHG strain to be genome engineered which was cultured. The cultured *Vibrio* sp. DHG strain was inoculated into a liquid LBv2+ ampicillin (100 ug/mL) medium and then incubated overnight. Further, the strain was inoculated at a 1/100 dilution ratio into a fresh medium to which 1 mM IPTG was added for additional cultivation. When the OD of the cultured *Vibrio* sp. DHG strain reached 0.7 to 0.8, the medium was cooled for 10 minutes using ice or the like. We centrifuged the cooled *Vibrio* sp. DHG strain to obtain only cells which were washed twice with an electroporation buffer. A double stranded DNA was introduced into the washed *Vibrio* sp. DHG strain by electroporation (0.8 kV). In the double stranded DNA, a homology of 1 to 3 kb around the targeted gene is placed next to both sides of the selection marker (preferably the cat gene) (FIG. 12). 1 mL of BHI recovery medium was added to the transformed *Vibrio* sp. DHG strain which was incubated at 37° C. for 3 hours therein.

The cultured strains were plated on plates containing antibiotics corresponding to selection markers and incubated for 6 hours. Colony PCR checked whether the genome engineering occurred in cells that showed antibiotic resistance. The selection marker was removed by introducing the pRSF_FLP as a plasmid for expression of the gamma protein into cells being subjected to the genome engineering. Colony PCR was finally used to identify whether the selection marker was deleted therefrom. In this connection, the cell lacking the selection marker is a *Vibrio* sp. DHG strain transformed with a gene encoding a gamma protein and an antibiotic resistance gene. The strain expresses the SXT recombinase, thereby allowing genome engineering using the single-stranded DNA oligos.

Example 10. Alginic Acid Metabolizing Enzyme Screening by Genomic Analysis of *Vibrio* sp. DHG Strain The possibility of metabolism of the alginic acid in the sea microalgae means that the alginic acid metabolic pathway is present in the *Vibrio* sp. DHG strain. Alginic acid is known to be converted into pyruvate and G3P through metabolism.

In order to search for enzymes related to alginic acid metabolism, genome sequence analysis was performed on the *Vibrio* sp. DHG strain. It was confirmed that in the *Vibrio* sp. DHG strain, enzymes essential for alginic acid metabolism as follows are present.

Alginate lyase 1 to 5
DEHU reductase (2-hydroxy-3-oxopropionate reductase) 1
2-dehydro-3-deoxygluconate kinase 1 to 2

Example 11. Preparation of Transformed Strain for Lycopene Production Using *Vibrio* sp. DHG Strain As the *Vibrio* sp. DHG strain may metabolize alginic acid as identified in Example 10, a plasmid containing an enzyme gene of biosynthesis of lycopene is introduced into the *Vibrio* sp. DHG strain which may be genome engineered in Example 9-4, thereby producing a transformed strain for the lycopene production.

Figure 17:
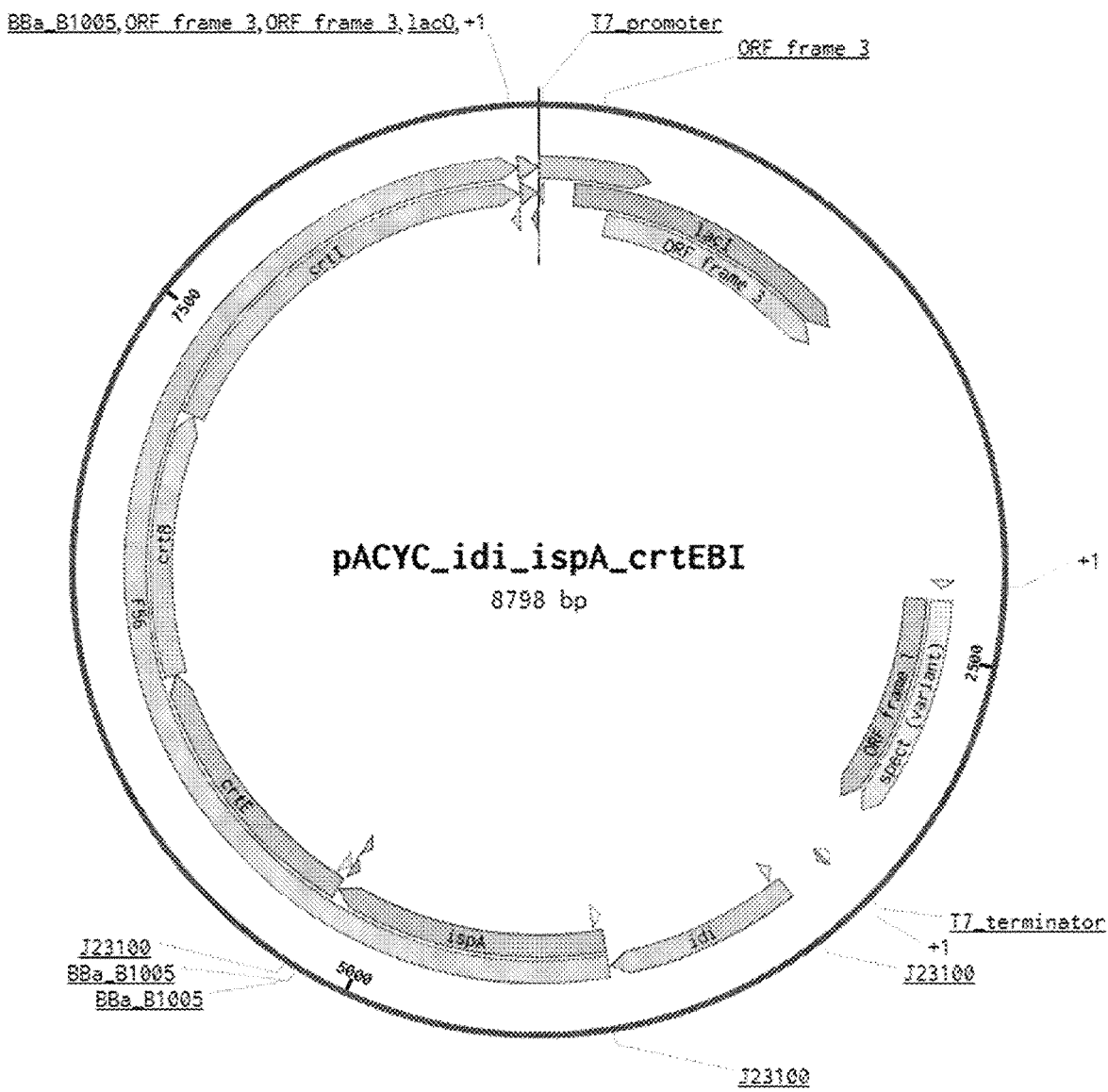
FIG. 17 shows a map of a plasmid pACYC_idi_isopA_crtEBI for lycopene production according to the present disclosure.

Specifically, the plasmid containing the lycopene biosynthetic enzyme gene used (i) a plasmid pACYC_idi_ispA_crtEBI (FIG. 17; SEQ ID NO: 53) which is improved based on the plasmid (pCDF_idi_ispA_crtEBI, doi: 10.1016/j.ymben.2016.10.003) developed to produce lycopene in *E. coli*, or (ii) a plasmid pACYC_idi_ispA_crtEBI_dxs (FIG. 18, SEQ ID NO: 54) which is newly constructed to further express the dxs gene derived from *E. coli*. The crtEBI gene (SEQ ID NO: 9) contained in the plasmid is derived from *Lamprocystis purpurea*. The idi (SEQ ID NO: 10), ispA (SEQ ID NO: 11) and dxs gene (SEQ ID NO: 12) are derived from *E. coli*. K-12 W3110. Further, the genes are designed to increase the gene expression thereof by the J23100 promoter as a constant promoter, and the synthetic 5' UTR with a high translation efficiency.

The transformed strain VDHG102 for lycopene production was prepared by transforming the *Vibrio* sp. DHG strain from which the dns gene was deleted using the plasmid pACYC_idi_ispA_crtEBI by the method of Example 5. After incubating the produced lycopene production strain and alginic acid for 9 hours, a lycopene production amount was measured. The composition of the medium used for the culture is as follows.

NaCl 30 g/L
$(NH_4)2SO_4$ 5 g/L
$K_2HPO_4$ 2 g/L
$MgSO_4 7H_2O$ 0.5 g/L
Alginate 10 g/L
ATCC Trace mineral solution 2 ml/L
Chloramphenicol 10 ug/mL Experimental group VDHG103 was achieved by transforming the *Vibrio* sp. DHG strain from which the dns gene is deleted using the plasmid pACYC_idi_ispA_crtEBI_dxs and corresponds to the lycopene production strain in which the dxs gene derived from *E. coli* is further expressed. Experimental group VDHG103 (Alg 20) was achieved by incubating the VDHG103 strain while the alginic acid was additionally supplied to the medium during the culture. Lycopene production by the transformed strain for lycopene production is shown in FIG. 13.

Figure 13:
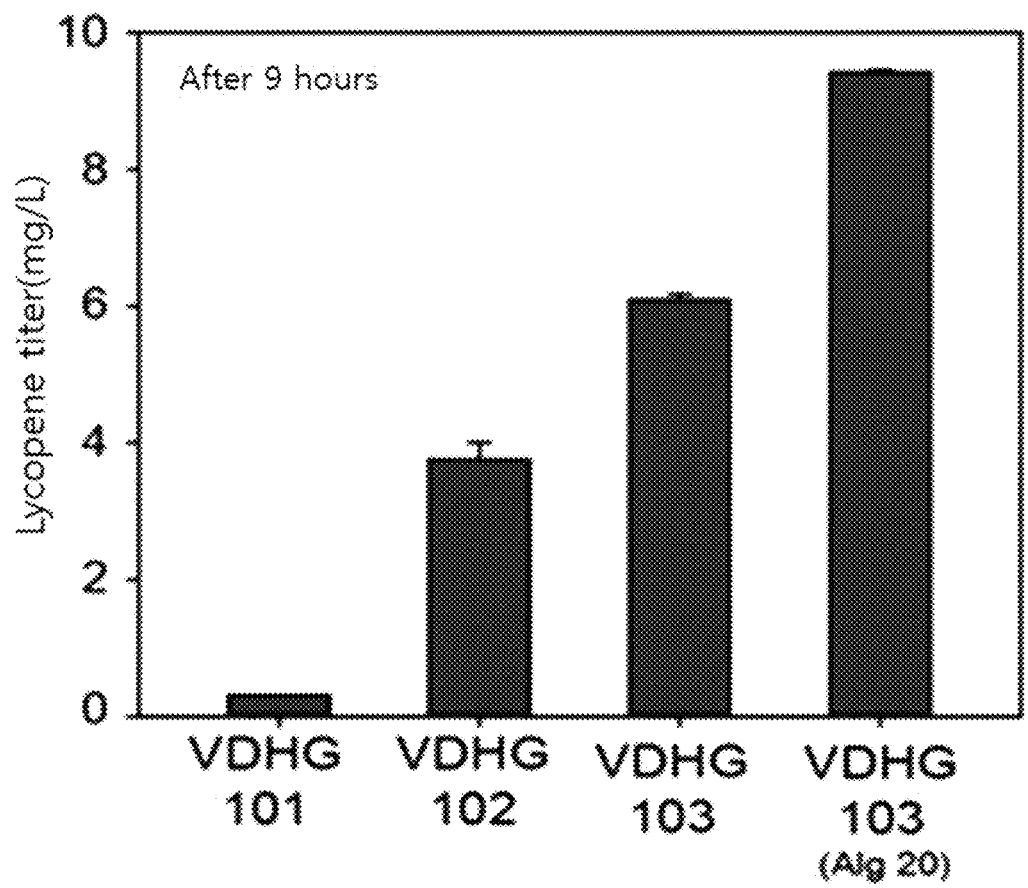
FIG. 13 shows a result of measuring a lycopene production amount by the transformed strain for lycopene production obtained by transforming the *Vibrio* sp. DHG strain according to the present disclosure.

As shown in FIG. 13, it is identified that the experimental group VDHG102 has 3.74 mg/L of lycopene production. Experimental group VDHG103 additionally expressing the dxs gene derived from *E. coli* has 6 mg/L of lycopene production. The experimental group VDHG103 (Alg 20) in which an additional supply of the alginic acid occurred has about 9.4 mg/L of lycopene production. The results suggest that the *Vibrio* sp. DHG strain can be used universally in the production of high value-added compounds such as lycopene.

Example 12. Preparation of Transformed Strain for Producing 2,3-Butanediol Using *Vibrio* sp. DHG Strain 2,3-butanediol is an industrially effective compound used in plastic synthesis, antifreeze, and pesticides. 2,3-butanediol is subjected to chemical conversion for being widely used for fuel additives and rubber synthesis. It is known that 2,3-butanediol may be produced by introducing and expressing operon (budACB) composed of budA, budB and budC derived from *Klebsiella pneumoniae*.

Thus, the budACB operon composed of budA (SEQ ID NO: 13), budB (SEQ ID NO: 14), and budC gene (SEQ ID NO: 15) was introduced into the *Vibrio* sp. DHG strain as prepared in Example 9-2. Thus, a 2,3-butanediol production strain was produced. Specifically, a tac promoter and the 5' UTR with a high translation efficiency were designed for efficient expression of the budACB operon. The plasmid pACYC_BudACB was designed using the tac promoter and the 5' UTR. The plasmid pACYC_BudACB is represented by the cleavage map shown in FIG. 14. The entire sequence is represented by the nucleotide sequence of SEQ ID NO: 55. The plasmid pACYC_BudACB was introduced into the *Vibrio* sp. DHG strain prepared in Example 9-2 to transform the latter to prepare a 2,3-butanediol production strain (Experimental Group 1).

Also, in order to increase the productivity and yield of the 2,3-butanediol, the genome engineering method of Example 9 may be used to sequentially delete the metabolite producing genes ldhA (lactic acid), frdABCD operon (succinate production) and pflB (conversion of pyruvate to Acetyl-CoA) from the *Vibrio* sp. DHG strain having the budACB operon introduced thereto, by using the plasmid comprising the flp flippase gene of Example 9-2 having a competing relationship with 2,3-butanediol production. Thus, the 2,3-butanediol production strain with increased production efficiency was prepared (Experimental group 2). The ldhA gene is represented by the nucleotide sequence of SEQ ID NO: 16. The genes constituting the frdABCD operon may be represented by nucleotide sequences of SEQ ID NOs: 17 to 20 respectively. The pflB gene is represented by the nucleotide sequence of SEQ ID NO: 21. Colony PCR was performed to identify the gene deletion result in the 2,3-butanediol production strain with increased production efficiency. The results are shown in FIG. 15.

Figure 15:
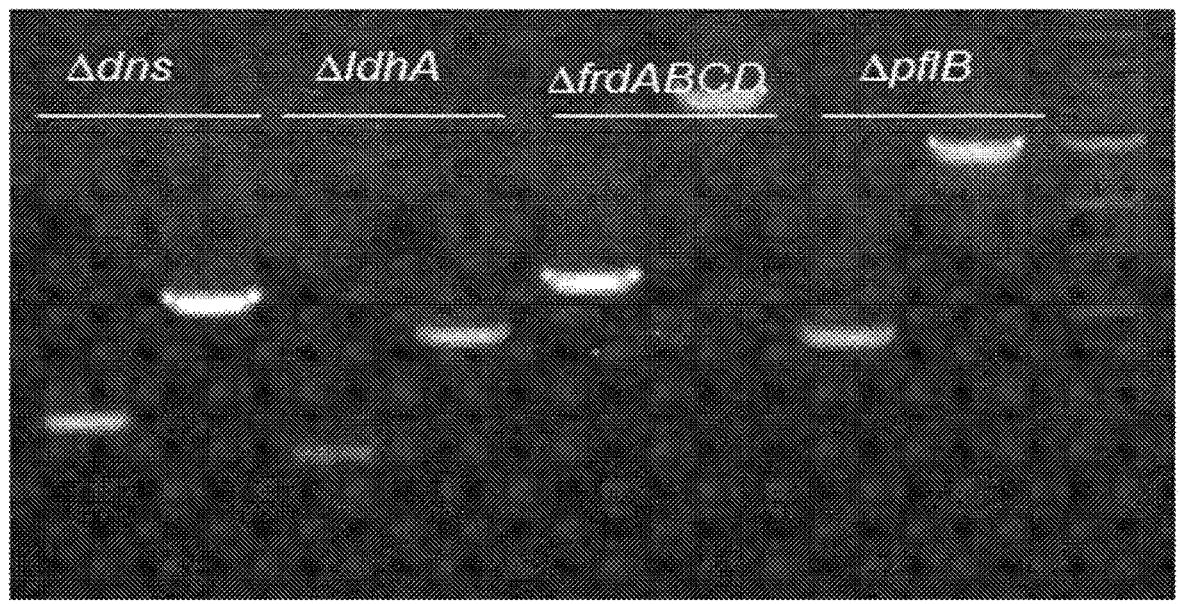
FIG. 15 shows a result of identifying gene deletion of the transformed strain for producing 2,3-butanediol according to the present disclosure through colony PCR.

As shown in FIG. 15, in the 2,3-butanediol production transformed strain with increased production efficiency, the metabolite producing genes ldhA, frdABCD operon and pflB having a competing relationship with 2,3-butanediol production are deleted.

Figure 16:
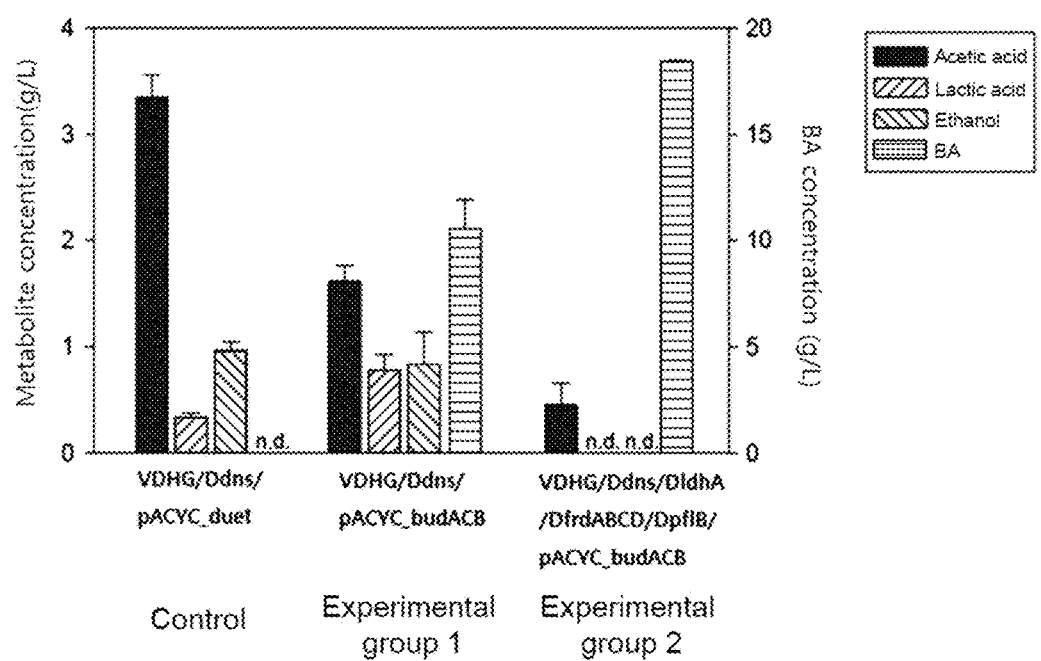
FIG. 16 shows a result of a metabolite of the transformed strain for 2,3-butanediol production according to the present disclosure and measuring a 2,3-butanediol production amount by the transformed strain.

Strains of Experimental Groups 1 and 2 were incubated at 30° C. and 250 rpm using media having following compositions, respectively. After the end of the culture, metabolites and the production of 2,3-butanediol were measured. The results are shown in FIG. 16. The control is a *Vibrio* sp. DHG strain prepared in Example 9-2 and is free of the plasmid pACYC_BudACB.

The composition of the medium is as follows. Compositions of alginic acid, mannitol, and glucose as obtained from the brown microalgae were used. The alginic acid, mannitol, and glucose were mixed with each other to obtain the carbon source. The total amount thereof was set to 50 g/L.

NaCl 10 g/L
$(NH_4)2SO_4$ 5 g/L
Potassium buffer 100 mM (pH 7)
Yeast extracts 5 g/L
$MgSO_4 \cdot 7H_2O$ 0.5 g/L
Carbon source 50 g/L
DSMZ Trace element solution 2 ml/L As shown in FIG. 16, it is identified that the control without the introduction of the plasmid pACYC_BudACB has no 2,3-butanediol production. On the other hand, Experimental Group 1 as a strain to which the plasmid pACYC_BudACB was introduced, produced 2,3-butanediol. Experimental group 2 as a strain from which the enzymes having competitive metabolic pathways are deleted shows the production of 2,3-butanediol as significantly increased. The results suggest that the *Vibrio* sp. DHG strain may be used universally in the production of high value-added compounds such as 2,3-butanediol.

Overall, the present inventors have isolated the *Vibrio* sp. DHG strains from seawater. The strain grows much faster in the minimal medium and nutrient-rich medium than microorganisms such as *Escherichia coli*. The strain is resistant to high initial sugar/salt concentrations. Further, the strain may be transformed using a conventional plasmid system for improving *E. coli*. Thus, the genome engineering of the *Vibrio* sp. DHG strain results in producing the lycopene and 2,3-butanediol. The *Vibrio* sp. DHG strain according to the present disclosure may be used in various production fields high value-added compounds using microorganisms.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

[Accession Number]
Depositary: Korea Research Institute of Bioscience and Biotechnology
Accession number: KCTC13239BP
Deposit Date: 2017 Apr. 6

---

What is claimed is:

1. A transformed *Vibrio* sp. DHG strain with improved metabolic efficiency for carbon sources,
    wherein the transformed *Vibrio* sp. DHG strain is obtained by introducing a SXT recombination system expression cassette into a *Vibrio* sp. DHG strain having accession number KCTC13239BP;
    wherein the *Vibrio* sp. DHG strain having accession number KCTC13239BP comprises a 16S rDNA gene consisting of the nucleotide sequence of SEQ ID NO: 1;
    wherein the SXT recombination system expression cassette comprises a synthetic 5' UTR (untranslated region) consisting of the nucleotide sequence of SEQ ID NO: 57; a promoter consisting of the nucleotide sequence selected from the group consisting of SEQ ID NOs: 22 to 35 and 56; and a gamma gene consisting of the nucleotide sequence of SEQ ID NO: 6; and
    wherein the carbon source comprises at least one selected from the group consisting of glucose, mannitol, sucrose, arabinose, galactose, glycerol and alginic acid.

2. The transformed *Vibrio* sp. DHG strain of claim 1, wherein the *Vibrio* sp. DHG strain having accession number KCTC13239BP comprises a beta gene consisting of the nucleotide sequence of SEQ ID NO: 3 or a beta protein consisting of the amino acid sequence of SEQ ID NO: 2.

3. The transformed *Vibrio* sp. DHG strain of claim 1, wherein the *Vibrio* sp. DHG strain having accession number KCTC13239BP comprises an exo gene consisting of the nucleotide sequence of SEQ ID NO: 5 or an exo protein consisting of the amino acid sequence of SEQ ID NO: 4.

4. A transformed strain for lycopene production,
    wherein a crtEBI gene consisting of the nucleotide sequence of SEQ ID NO: 9 is further introduced to the transformed *Vibrio* sp. DHG strain of claim 1.

5. The transformed strain for lycopene production of claim 4, wherein an idi gene consisting of the nucleotide sequence of SEQ ID NO: 10 is further introduced thereinto.

6. The transformed strain for lycopene production of claim 4, wherein an ispA gene consisting of the nucleotide sequence of SEQ ID NO: 11 is further introduced thereinto.

7. The transformed strain for lycopene production of claim 4, wherein a dxs gene consisting of the nucleotide sequence of SEQ ID NO: 12 is further introduced thereinto.

8. A transformed strain for producing 2,3-butanediol, wherein the transformed strain is obtained by introducing, into the transformed *Vibrio* sp. DHG strain of claim 1, at least one gene selected from the group consisting of:
- a budA gene consisting of the nucleotide sequence of SEQ ID NO: 13;
- a budB gene consisting of the nucleotide sequence of SEQ ID NO: 14; and
- a budC gene consisting of the nucleotide sequence of SEQ ID NO: 15.

9. The transformed strain for producing 2,3-butanediol of claim 8, wherein the transformed strain is obtained by deleting, from the transformed *Vibrio* sp. DHG strain, at least one gene selected from the group consisting of:
- a IdhA gene consisting of the nucleotide sequence of SEQ ID NO: 16;
- a frdA gene consisting of the nucleotide sequence of SEQ ID NO: 17;
- a frdB gene consisting of the nucleotide sequence of SEQ ID NO: 18;
- a frdC gene consisting of the nucleotide sequence of SEQ ID NO: 19;
- a frdD gene consisting of the nucleotide sequence of SEQ ID NO: 20;
- a pflB gene consisting of the nucleotide sequence of SEQ ID NO: 21.

10. A method of producing lycopene, the method comprising culturing the transformed strain for lycopene production of claim 4.

11. A method for producing 2,3-butanediol, the method comprising culturing the transformed strain for producing 2,3-butanediol of claim 8.

* * * * *